(12) United States Patent
Omoto et al.

(10) Patent No.: US 8,952,008 B2
(45) Date of Patent: Feb. 10, 2015

(54) CHEMICAL COMPOUNDS

(71) Applicant: Pfizer Limited, Sandwich (GB)

(72) Inventors: Kiyoyuki Omoto, Great Abington (GB); Robert McKenzie Owen, Great Abington (GB); David Cameron Pryde, Great Abington (GB); Christine Ann Louise Watson, Sandwich (GB); Mifune Takeuchi, Sandwich (GB)

(73) Assignee: Pfizer Limited, Sandwich (GB)

( * ) Notice: Subject to any disclaimer, the term of this patent is extended or adjusted under 35 U.S.C. 154(b) by 0 days.

(21) Appl. No.: 14/103,960

(22) Filed: Dec. 12, 2013

(65) Prior Publication Data

US 2014/0171435 A1    Jun. 19, 2014

Related U.S. Application Data

(60) Provisional application No. 61/737,157, filed on Dec. 14, 2012.

(51) Int. Cl.
*A01N 43/58* (2006.01)
*A61K 31/495* (2006.01)
*C07D 487/00* (2006.01)

(52) U.S. Cl.
USPC ............................ 514/248; 514/250; 544/236

(58) Field of Classification Search
USPC ................................... 514/248, 250; 544/236
See application file for complete search history.

(56) References Cited

FOREIGN PATENT DOCUMENTS

| WO | 0001697 A1 | 1/2000 |
|----|------------|--------|
| WO | 0238568 A1 | 5/2002 |
| WO | 03008418 A1 | 1/2003 |
| WO | 2005080355 A1 | 9/2005 |
| WO | 2012004714 A2 | 1/2012 |

OTHER PUBLICATIONS

PCT Search Report and Written Opinion from International Searching Authority for PCT/IB2013/060631 dated Jan. 30, 2014.

*Primary Examiner* — Paul V. Ward
(74) *Attorney, Agent, or Firm* — J. Michael Dixon

(57) ABSTRACT

The present invention relates to imidazopyridazine derivatives. More particularly, it relates to 4-(biphenyl-3-yl)-7H-imidazo[4,5-c]pyridazine derivatives of formula (I):

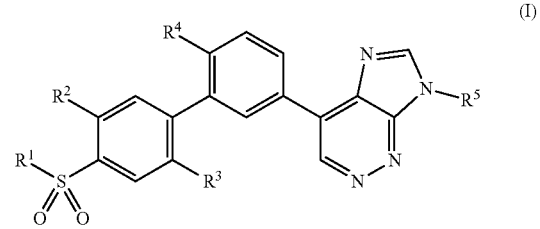

and pharmaceutically acceptable salts thereof, wherein $R^1$, $R^2$, $R^3$, $R^4$ and $R^5$ are as defined in the description. The imidazopyridazine derivatives of the present invention modulate the activity of the $GABA_A$ receptor. They are useful in the treatment of a number of conditions, including pain.

19 Claims, No Drawings

CHEMICAL COMPOUNDS

This application claims priority from U.S. Provisional Application No. 61/737,157 filed on Dec. 14, 2012.

FIELD OF THE INVENTION

The present invention relates to imidazopyridazine derivatives. More particularly, it relates to 4-(biphenyl-3-yl)-7H-imidazo[4,5-c]pyridazine derivatives. The imidazopyridazine derivatives of the present invention modulate the activity of the $GABA_A$ receptor. They are useful in the treatment of a number of conditions, including pain.

BACKGROUND

Gamma-aminobutyric acid (GABA) has been identified as a major inhibitory neurotransmitter, and agents that modulate GABAergic neurotransmission are used extensively in the treatment of conditions such as epilepsy, anxiety and depression. Two families of GABA receptor have been described, termed $GABA_A$ and $GABA_B$.

The $GABA_A$ receptor is a member of the ligand-gated ion channel superfamily. The functional receptor generally comprises a number of subunits. At least 16 such subunits have been characterized, including 6 alpha subunits ($\alpha_{1-6}$), 3 beta subunits ($\beta_{1-3}$), 3 gamma subunits ($\gamma_{1-3}$), and delta, epsilon, pi and theta subunits ($\delta$, $\epsilon$, $\pi$, $\theta$). Most $GABA_A$ receptors are made up of 2 alpha, 2 beta and one gamma subunit. Several drug binding sites have been described. These include the binding site for the endogenous ligand (GABA), and allosteric binding sites. Drugs that bind at the allosteric binding sites may be positive allosteric modulators, which increase responsiveness, negative allosteric modulators, which decrease receptor responsiveness, or neutral, which term refers to compounds that bind to the allosteric binding sites without modulating the activity of the receptor. Recent evidence has suggested that $GABA_A$ receptors comprising either the $\alpha_2$ or $\alpha_3$ subunit (herein termed $GABA_A$ $\alpha_{2/3}$ receptors) may be involved in certain pain states, and that positive allosteric modulators of these receptors may be useful analgesics (Mirza, N. R. and Munro, G., *Drug News and Perspectives*, 2010, 23(6), 351-360).

4-(Biphenyl-3-yl)-7H-imidazo[4,5-c]pyridazine derivatives have not been reported as having an interaction with $GABA_A$ $\alpha_{2/3}$ receptors. International patent applications PCT/GB01/04948 (published as WO2002/038568) and PCT/GB02/03114 (published as WO2003/008418) disclose 7-phenylimidazo[1,2-b][1,2,4]triazine derivatives that have affinity for the $\alpha_2$, $\alpha_3$ and/or $\alpha_5$ subunits. International patent application PCT/US99/14935 (published as WO2000/001697) discloses inter alia 4-phenyl-7H-imidazo[4,5-c]pyridazine derivatives which are corticotrophin releasing factor antagonists.

There is a continuing interest in finding new compounds that interact with $GABA_A$ receptors, and particularly for compounds that have a reduced propensity for causing the adverse events such as drowsiness that are associated with the currently available $GABA_A$ modulators such as benzodiazepines. It is thought that these adverse effects are a result of modulation of $\alpha_1$ subunit-containing receptors, and so preferred compounds will have a high affinity for the $\alpha_{2/3}$ subunit-containing receptors with good efficacy as positive allosteric modulators, while having low efficacy at receptors with other $\alpha$ subunits, particularly the $\alpha_1$ subunit-containing receptors.

These drug candidates should additionally have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile. They should be non-toxic and demonstrate few side-effects. Ideal drug candidates should exist in a physical form that is stable, non-hygroscopic and easily formulated.

SUMMARY OF THE INVENTION

In a first aspect, the present invention provides a compound of formula (I)

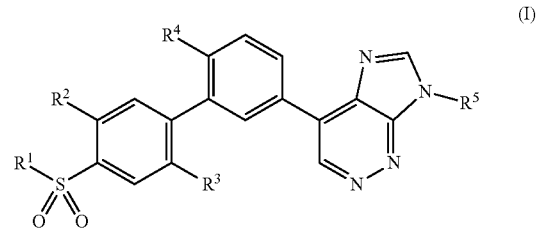

or a pharmaceutically acceptable salt thereof, wherein:
$R^1$ is selected from $(C_1-C_4)$alkyl, $(C_3-C_4)$cycloalkyl, $NH_2$, and $NH(C_1-C_4)$alkyl and $R^2$ is H; or
$R^1$ and $R^2$ together are —$CH_2$—$CH_2$— or —$N(CH_3)$—$CH_2$—;
$R^3$ is selected from H, F, $CHF_2$, $OCH_3$ and CN;
$R^4$ is selected from H, F, Cl, OH, $OCH_3$ and CN; and
$R^5$ is selected from $(C_2-C_4)$alkyl, $(C_3-C_5)$cycloalkyl and methyl-substituted $(C_3-C_5)$cycloalkyl, The compounds of formula (I) and their pharmaceutically acceptable salts are referred to herein as "the compounds of the invention". The definition above is referred to herein as embodiment E1 of this aspect. Further embodiments of this aspect of the invention are described in detail below.

In another aspect, the invention provides for a compound of formula (I) as described above, or in any one of the preferred embodiments, or a pharmaceutically acceptable salt thereof, for use as a medicament. In an embodiment according to this aspect the compound of formula (I), or a pharmaceutically acceptable salt thereof, is for use in the treatment of pain.

In another aspect, the invention provides for a pharmaceutical composition comprising a compound of formula (I) as described above, or in any one of the preferred embodiments, or a pharmaceutically acceptable salt thereof, and a pharmaceutically acceptable excipient.

In another aspect, the invention provides for a method of treating pain comprising administering a therapeutically effective amount of a compound of formula (I) as described above, or in any one of the preferred embodiments, or a pharmaceutically acceptable salt thereof, to an individual in need of such treatment.

In another aspect, the invention provides for the use of a compound of formula (I) as described above, or in any one of the preferred embodiments, or a pharmaceutically acceptable salt thereof, for the manufacture of a medicament for treating pain.

In another aspect, the invention provides for the use of a compound of formula (I) as described above, or in any one of the preferred embodiments, or a pharmaceutically acceptable salt thereof, for the treatment of pain.

In another aspect, the invention provides for a combination comprising a compound of formula (I) as described above, or in any one of the preferred embodiments, or a pharmaceutically acceptable salt thereof, and a second pharmaceutically active agent.

DETAILED DESCRIPTION OF THE INVENTION

Alkyl groups, containing the requisite number of carbon atoms, can be unbranched or branched. $(C_1-C_4)$Alkyl includes methyl, ethyl, n-propyl (1-propyl) and isopropyl (2-propyl, 1-methylethyl), n-butyl (1-butyl), sec-butyl (2-butyl, 1-methylpropyl), isobutyl (2-methylpropyl), and tert-butyl (1,1-dimethylethyl).

$(C_3-C_5)$Cycloalkyl includes cyclopropyl, cyclobutyl and cyclopentyl. Methyl-substituted $(C_3-C_5)$cycloalkyl includes 1-methylcyclopropyl, 2-methylcyclopropyl, 1-methylcyclobutyl, 2-methylcyclobutyl, 3-methylcyclobutyl, 1-methylcyclopentyl, 2-methylcyclopentyl and 3-methylcyclopentyl.

In compounds of formula (I) wherein $R^1$ and $R^2$ together are —N(CH$_3$)—CH$_2$—, it should be understood that the nitrogen atom corresponds to "$R^1$" and the methylene carbon atom corresponds to "$R^2$", so providing a compound of formula ($I^4$).

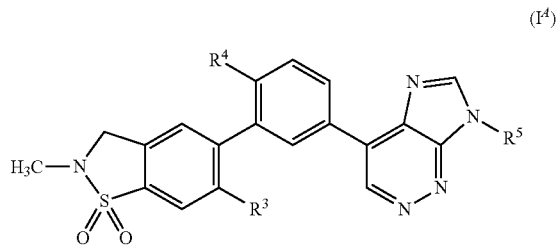

($I^4$)

Further specific embodiments of the compounds of the invention are as follows.

In embodiment E2, there is provided a compound according to embodiment E1 or a pharmaceutically acceptable salt thereof, wherein $R^1$ is $(C_2-C_4)$alkyl and $R^2$ is H In embodiment E3, there is provided a compound according to embodiment E1 or E2, or a pharmaceutically acceptable salt thereof, wherein $R^3$ is selected from F and OCH$_3$.

In embodiment E4, there is provided a compound according to any one of embodiments E1, E2 or E3 or a pharmaceutically acceptable salt thereof, wherein $R^4$ is selected from H and F.

In embodiment E5, there is provided a compound according to any one of embodiments E1, E2, E3 or E4, or a pharmaceutically acceptable salt thereof, wherein $R^5$ is $(C_2-C_4)$alkyl.

Preferred compounds of the invention include:
7-ethyl-4-(6-fluoro-4'-((1-methylethyl)sulfonyl)biphenyl-3-yl)-7H-imidazo[4,5-c]pyridazine;
4-(4'-ethanesulfonyl-6-fluoro-2'-methoxybiphenyl-3-yl)-7-ethyl-7H-imidazo[4,5-c]pyridazine;
7-cyclopropyl-4-(4'-ethylsulfonyl-6-fluorobiphenyl-3-yl)-7H-imidazo[4,5-c]pyridazine; and
4-(4'-ethanesulfonyl-2',6-difluorobiphenyl-3-yl)-7-(1-methylethyl)-7H-imidazo[4,5-c]pyridazine.

A particularly preferred compound of the invention is 4-(4'-ethanesulfonyl-6-fluoro-2'-methoxybiphenyl-3-yl)-7-ethyl-7H-imidazo[4,5-c]pyridazine.

Certain compounds of formula (I) include one or more stereogenic centers and so may exist as optical isomers, such as enantiomers and diastereomers. All such isomers and mixtures thereof are included within the scope of the present invention.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Hemisalts of acids and bases may also be formed, for example, hemisulphate salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. D$_2$O, d$_6$-acetone and d$_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994).

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

Where ratios of solvents are given, the ratios are by volume.

In the Schemes that follow, X is Cl, Br or I, and M is a boronic ester or boronic acid.

According to a first process, compounds of formula (I) may be prepared by the process illustrated in Scheme 1.

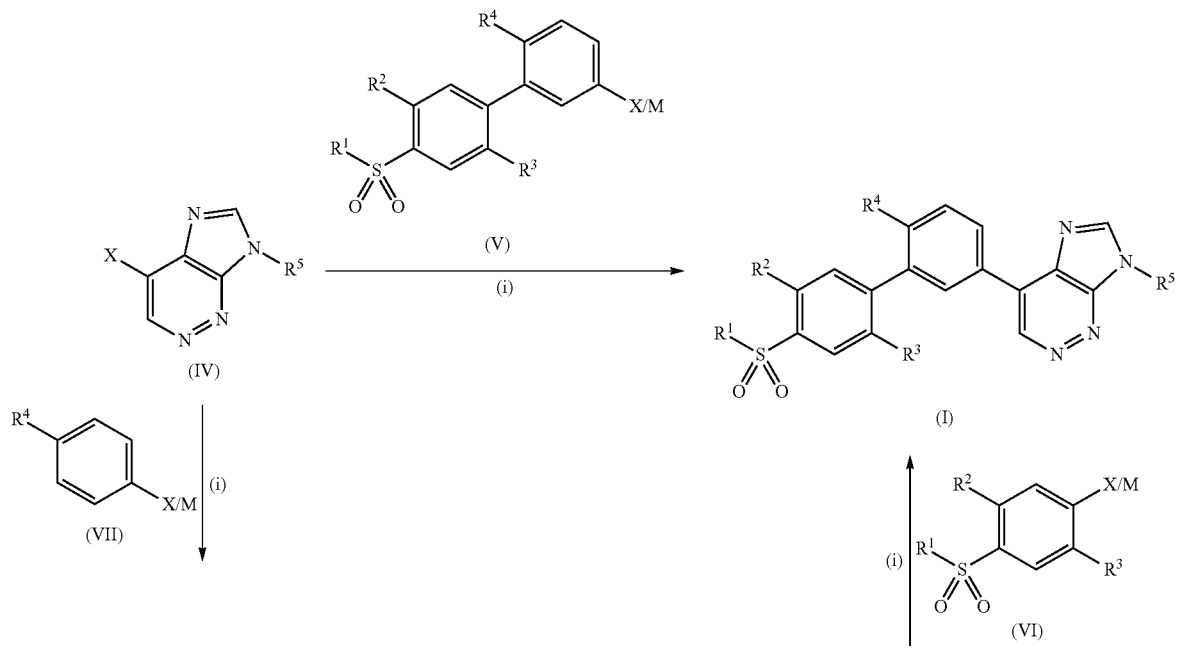

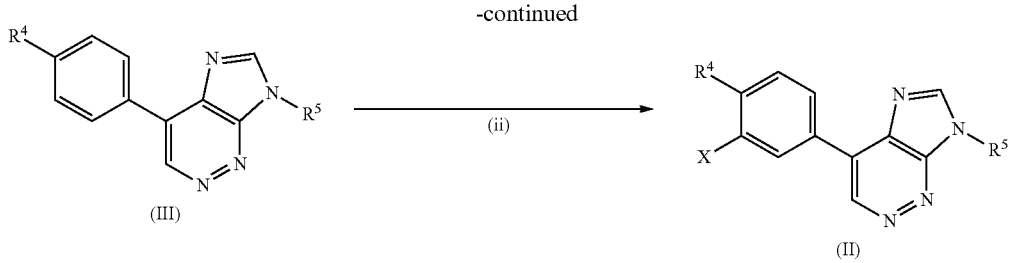

Compounds of formula (I) may be prepared from compounds of formula (II) or (IV) according to process step (i), a Suzuki cross coupling reaction with compounds of formula (V) or (VI). Typical conditions for the metal catalysed cross coupling reaction comprise a palladium catalyst such as dichloro[1,1-bis(di-tert-butylphosphino)]ferrocene palladium(II) or tetrakis(triphenylphosphine)palladium(0) or tris(dibenzylideneacetone)palladium(0) with a suitable ligand such as tricyclohexylphosphine, with a base such as sodium, potassium or cesium carbonate in dioxane/water or DMF/water either heating to reflux thermally, or heating up to 120° C. under microwave irradiation. Preferred conditions comprise tetrakis(triphenylphosphine)palladium(0) with sodium carbonate in dioxane/water at 110° C. During this step, if compounds of formula (V) and (VI) need to be converted to the boronic acid or ester, an additional step may be used to convert X to M. Typical conditions comprise dichloro[1,1-bis(di-tert-butylphosphino)]ferrocene palladium(II) with potassium acetate in dioxane at 110° C.

Compounds of formula (VI) are either commercially available or are well-known to those skilled in the art with reference to literature precedents and/or the preparations described herein, or may be prepared according to Scheme 4.

Compounds of formula (IV) are either commercially available or are well-known to those skilled in the art with reference to literature precedents and/or the preparations described herein or may be prepared according to Schemes 2 and 3.

Compounds of formula (V) may be prepared according to Scheme 4.

Compounds of formula (II) may be prepared from compounds of formula (III) according to process step (ii), an electrophilic halogenation reaction. Typical conditions comprise 1,3-diiodo-5,5-dimethylhydantoin or 1,3-dibromo-5,5-dimethylhydantoin in concentrated sulphuric acid at from 0° C. to room temperature.

Compounds of formula (III) may be prepared from compounds of formula (IV) and (VII) according to process step (i), a Suzuki cross coupling reaction as described above. Preferred conditions comprise tetrakis(triphenylphosphine)palladium(0) and sodium carbonate in DMF and water at reflux.

Compounds of formula (VII) are either commercially available or are well-known to those skilled in the art with reference to literature precedents and/or the preparations described herein.

According to a second process, compounds of formula (IV) may be prepared by the process illustrated in Scheme 2.

Scheme 2

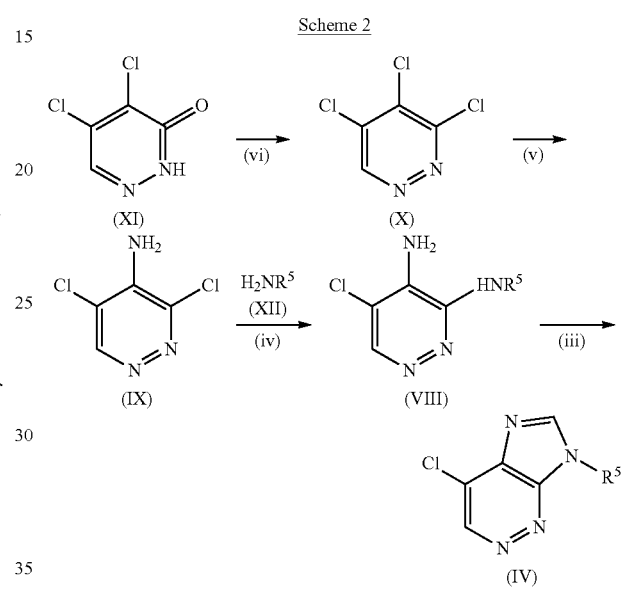

Compounds of formula (IV) may be prepared from compounds of formula (VIII) according to process step (iii) a condensation reaction at elevated temperature. Typical conditions comprise heating compounds of formula (VIII) neat with triethylorthoformate at 130° C.

Compounds of formula (VIII) may be prepared from compounds of formula (IX) according to process step (iv) a nucleophilic aromatic substitution reaction with compounds of formula (XII). Typical conditions comprise heating compounds of formula (XII) with compounds of formula (IX) either in a sealed vessel or under microwave irradiation at from 100-150° C. either neat or in a suitable solvent such as water or acetic acid.

Compounds of formula (XII) are commercially available.

Compounds of formula (IX) may be prepared from compounds of formula (X) according to process step (v), a nucleophilic aromatic substitution reaction with ammonia. Preferred conditions comprise heating compounds of formula (X) with ammonia in a suitable solvent such as ethanol under microwave irradiation at 120° C. Compounds of formula (X) may be prepared from compounds of formula (XI) according to process step (vi), a dehydrating chlorination reaction. Typical conditions comprise heating compounds of formula (XI) neat in $POCl_3$ at 110° C.

The compound of formula (XI) is commercially available.

According to a third process, compounds of formula (IV) may also be prepared by the process illustrated in Scheme 3.

Scheme 3

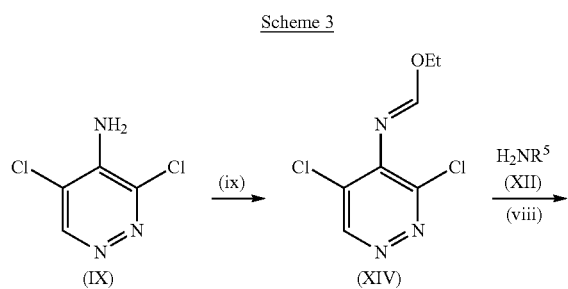

Compounds of formula (XIII) may be prepared from compounds of formula (XIV) according to process step (viii) a nucleophilic substitution reaction with compounds of formula (XII) in the presence of a suitable base such as sodium hydride in a solvent such as THF at from 0° C. to room temperature.

Compounds of formula (XIV) may be prepared from compounds of formula (IX) according to process step (ix), an alkylation reaction with triethylorthoformate. Typical conditions comprise pyridinium para-toluenesulfonate with triethylorthoformate at 100° C.

Compounds of formula (IX) may be prepared as described in Scheme 2. According to a fourth process, compounds of formulae (VI) and (V) may also be prepared by the processes illustrated in Scheme 4.

Scheme 4

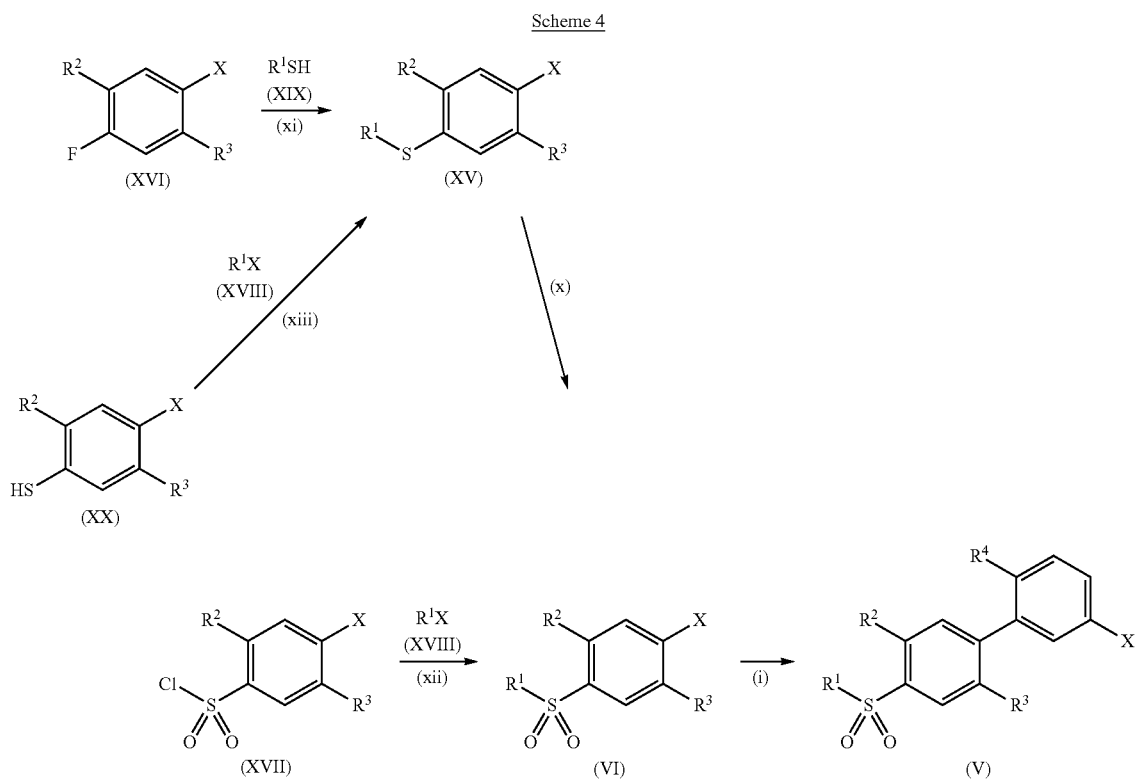

-continued

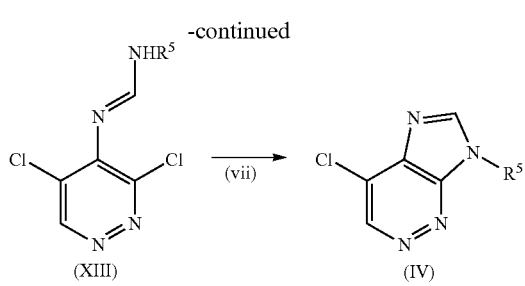

Compounds of formula (IV) may be prepared from compounds of formula (XIII) according to process step (vii), an aromatic cyclisation reaction. Preferred conditions comprise a suitable catalyst such as copper(I) bromide with a suitable ligand such as 1,10-phenanthroline in a solvent such as DMF in the presence of an inorganic base such as cesium carbonate at elevated temperature.

Compounds of formula (V) may be prepared from compounds of formula (VI) according to process step (i) a Suzuki cross-coupling reaction as described in Scheme 1.

Compounds of formula (VI) may be prepared from compounds of formula (XVII) according to process step (xii), a displacement of the sulfonyl chloride with an alkyl halide of formula (XVIII) via a sulfonyl hydrazide. Typical conditions comprise hydrazine monohydrate in THF at 0° C. followed by sodium acetate and compounds of formula (XVIII) in IMS at 85° C.

Compounds of formula (VI) may also be prepared from compounds of formula (XV) according to process step (x), an oxidation reaction in the presence of a suitable oxidising reagent. Preferred conditions comprise meta-chloroperoxybenzoic acid in DCM at from 0° C. to room temperature.

Compounds of formula (XV) may be prepared from compounds of formula (XVI) and (XIX) according to process step (xi), a nucleophilic aromatic substitution reaction. Preferred conditions comprise a sodium salt of compounds of formula (XIX) in DMSO at elevated temperature.

Compounds of formula (XV) may also be prepared from compounds of formula (XX) and (XVIII) according to process step (xiii), and alkylation reaction in the presence of a suitable base. Typical conditions comprise either potassium tert-butoxide or cesium carbonate in DMSO at from 70-90° C.

Compounds of formula (XIX), (XVIII), (XVI) and (XX) are either commercially available or are well-known to those skilled in the art with reference to literature precedents and/or the preparations described herein.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 μg to 100 mg of the compound of formula (I). The overall daily dose will typically be in the range 1 μg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

The compounds of the invention are useful because they exhibit pharmacological activity, i.e., $GABA_A$ channel modulation. More particularly, the compounds of the invention are positive allosteric modulators of the $GABA_A$ channel. Preferred compounds of the invention are selective modulators of the $\alpha_2$, $\alpha_3$ and/or $\alpha_5$ subtypes, with lower efficacy and/or affinity at the $\alpha_1$, $\alpha_4$ and $\alpha_6$ subtypes. The compounds of the invention are accordingly of use in the treatment of disorders in animals for which a $GABA_A$ positive allosteric modulator is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a $GABA_A$ positive allosteric modulator is indicated.

In a further aspect of the invention there is provided use of a compound of the invention for the preparation of a medicament for the treatment of a disorder for which a $GABA_A$ positive allosteric modulator is indicated.

In a further aspect of the invention there is provided a method of treating a disorder in an animal (preferably a mammal, more preferably a human) for which a $GABA_A$ positive allosteric modulator is indicated, comprising administering to said animal a therapeutically effective amount of a compound of the invention.

The $GABA_A$ positive allosteric modulators of formula (I) may be used:

- as analgesics, for example for the treatment of pain, including acute pain, chronic pain, neuropathic pain, nociceptive (including inflammatory) pain, somatic pain, visceral pain, and dysfunctional pain, as further discussed below, and in particular for pain conditions wherein there is a brain or spinal component to the underlying mechanism;
- as anticonvulsants, for example for the treatment of epilepsy and epilepsy associated disorders, including Lennox-Gastaut syndrome, Dravet's disease, and generalised epilepsy with febrile seizures plus (GEFS+);
- as anxiolytic agents, for example for the treatment of panic disorder, generalized anxiety disorder, stress disorders such as post-traumatic stress disorder, acute stress disorder and substance-induced stress disorder, phobias such as agoraphobia, social phobia and animal phobias, and obsessive-compulsive disorder; and
- as muscle relaxants, for example for the treatment of muscle spasm, dystonia, spasticity (including generalised and focal spasticity) and essential tremor.

The $GABA_A$ positive allosteric modulators of formula (I) may also be used for the treatment of autism, or as antipsychotic agents, for example for the treatment of schizophrenia.

Other therapeutic indications for the $GABA_A$ positive allosteric modulators of formula (I) include use as antidepressant agents, for example for the treatment of depressive and bipolar disorders and cyclothymia; as antiemetic agents, for example for the treatment of chemotherapy- or radiation-induced emesis, post-operative nausea and vomiting, and motion sickness; as cognition-enhancing agents, for example for the treatment of neurodegenerative disorders, such as Alzheimer's disease, and cerebral ischemia; as sleep improving agents, for example for the treatment of sleep disorders such as insomnia and circadian rhythm disorders such as jet-lag, or for use as pre-medication prior to anaesthesia or endoscopy; and use in the treatment of addiction phenotypes such as alcoholism, Angelman syndrome, attention deficit hyperactivity disorder, bladder urgency, bowel abnormalities, eating disorders such as anorexia nervosa and bulimia nervosa, Fragile X syndrome, hearing disorders such as tinnitus and age-related hearing impairment, multiple sclerosis, neuroses, overactive bladder with sensory disturbance, premenstrual syndrome, restless legs syndrome, and urinary incontinence.

A preferred use for the compounds of formula (I) is the treatment of pain. Pain may be either acute or chronic and additionally may be of central and/or peripheral origin. Pain may be of a neuropathic and/or nociceptive and/or inflammatory nature, such as pain affecting either the somatic or visceral systems, as well as dysfunctional pain affecting multiple systems.

Physiological pain is an important protective mechanism designed to warn of danger from potentially injurious stimuli from the external environment. The system operates through a specific set of primary sensory neurones and is activated by noxious stimuli via peripheral transducing mechanisms (see Meyer et al., 2006, Wall and Melzack's Textbook of Pain ($5^{th}$ Ed), Chapter1). These sensory fibres are known as nociceptors, and are characteristically small diameter axons with slow conduction velocities, of which there are two main types, A-delta fibres (myelinated) and C fibres (non-myelinated). Nociceptors encode the intensity, duration and quality of noxious stimulus and by virtue of their topographically organised projection to the spinal cord, the location of the stimulus. The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually, although not always, associated with a specific cause such as a defined injury, is often sharp and severe and can result from numerous origins such as surgery, dental work, a strain or a sprain. Acute pain does not generally result in any persistent psychological response. When a substantial injury occurs to body tissue, via disease or trauma, the characteristics of nociceptor activation may be altered such that there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury or alteration which can be associated with maladaptation and aberrant activity (Woolf & Salter, 2000, Science, 288, 1765-1768). As such, chronic pain is long-term pain, typically persisting for more than three months and leading to significant psychological and emotional problems. Common examples of chronic pain are neuropathic pain (e.g. painful diabetic neuropathy or postherpetic neuralgia), carpal tunnel syndrome, back pain, headache, cancer pain, arthritic pain and chronic post-surgical pain, but may include any chronic painful condition affecting any system, such as those described by the International Association for the Study of Pain (Classification of Chronic Pain, a publication freely available for download at http://www.iasp-pain.org).

The clinical manifestation of pain is present when discomfort and abnormal sensitivity feature among the patient's symptoms. Patients tend to be quite heterogeneous and may present with various pain symptoms. Such symptoms can include: 1) spontaneous pain which may be dull, burning, or stabbing; 2) exaggerated pain responses to noxious stimuli (hyperalgesia); and 3) pain produced by normally innocuous stimuli (allodynia) (Meyer et al., 2006, Wall and Melzack's Textbook of Pain ($5^{th}$ Ed), Chapter1). Although patients suffering from various forms of acute and chronic pain may have similar symptoms, the underlying mechanisms may be different and may, therefore, require different treatment strategies. Apart from acute or chronic, pain can also be broadly categorized into: nociceptive pain, affecting either the somatic or visceral systems, which can be inflammatory in nature (associated with tissue damage and the infiltration of immune cells); or neuropathic pain.

Nociceptive pain can be defined as the process by which intense thermal, mechanical, or chemical stimuli are detected by a subpopulation of peripheral nerve fibers, called nociceptors, and can be induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 2006, Wall and Melzack's Textbook of Pain ($5^{th}$ Ed), Chapter1). Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from strains/sprains, burns, myocardial infarction and acute pancreatitis, post-operative pain (pain following any type of surgical procedure), posttraumatic pain, pain associated with gout, cancer pain and back pain. Cancer pain may be chronic pain such as tumour related pain (e.g. bone pain, headache, facial pain or visceral pain) or pain associated with cancer therapy (e.g. in response to chemotherapy, immunotherapy, hormonal therapy or radiotherapy). Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Nociceptive pain can also be related to inflammatory states. The inflammatory process is a complex series of biochemical and cellular events, activated in response to tissue injury or the presence of foreign substances, which results in swelling and pain (McMahon et al., 2006, Wall and Melzack's Textbook of Pain ($5^{th}$ Ed), Chapter3). A common inflammatory condition associated with pain is arthritis. It has been estimated that almost 27 million Americans have symptomatic osteoarthritis (OA) or degenerative joint disease (Lawrence et al., 2008, Arthritis Rheum, 58, 15-35); most patients with osteoarthritis seek medical attention because of the associated pain. Arthritis has a significant impact on psychosocial and physical function and is known to be the leading cause of disability in later life. Rheumatoid arthritis is an immune-mediated, chronic, inflammatory polyarthritis disease, mainly affecting peripheral synovial joints. It is one of the commonest chronic inflammatory conditions in developed countries and is a major cause of pain.

In regard to nociceptive pain of visceral origin, visceral pain results from the activation of nociceptors of the thoracic, pelvic, or abdominal organs (Bielefeldt and Gebhart, 2006, Wall and Melzack's Textbook of Pain ($5^{th}$ Ed), Chapter48). This includes the reproductive organs, spleen, liver, gastrointestinal and urinary tracts, airway structures, cardiovascular system and other organs contained within the abdominal cavity. As such visceral pain refers to pain associated with conditions of such organs, such as painful bladder syndrome, interstitial cystitis, prostatitis, ulcerative colitis, Crohn's disease, renal colic, irritable bowl syndrome, endometriosis and dysmenorrheal (Classification of Chronic Pain, available at http://www.iasp-pain.org). Currently the potential for a neuropathic contribution (either through central changes or nerve injury/damage) to visceral pain states is poorly understood but may play a role in certain conditions (Aziz et al., 2009, Dig Dis 27, Suppl 1, 31-41).

Neuropathic pain is currently defined as pain arising as a direct consequence of a lesion or disease affecting the somatosensory system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Dworkin, 2009, Am J Med, 122, S1-S2; Geber et al., 2009, Am J Med, 122, S3-S12; Haanpaa et al., 2009, Am J Med, 122, S13-S21). The symptoms of neuropathic pain are difficult to treat, as they are often heterogeneous even between patients with the same disease (Dworkin, 2009, Am J Med, 122, S1-S2; Geber et al., 2009, Am J Med, 122, S3-S12; Haanpaa et al., 2009, Am J Med, 122, S13-S21). They include spontaneous pain, which can be continuous, and paroxysmal or abnormal evoked pain, such as hyperalgesia (increased sensitivity to a noxious stimulus) and allodynia (sensitivity to a normally innocuous stimulus).

It should be noted that some types of pain have multiple aetiologies and thus can be classified in more than one area, e.g. back pain, cancer pain and even migraine headaches may include both nociceptive and neuropathic components.

Similarly other types of chronic pain, perhaps less well understood, are not easily defined by the simplistic definitions of nociceptive or neuropathic. Such conditions include in particular fibromyalgia and chronic regional pain syndrome, which are often described as dysfunctional pain states e.g. fibromyalgia or complex regional pain syndrome (Woolf, 2010, J Clin Invest, 120, 3742-3744), but which are included in classifications of chronic pain states (Classification of Chronic Pain, available at http://www.iasp-pain.org).

A $GABA_A$ positive allosteric modulator may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

For the treatment of pain, a $GABA_A$ positive allosteric modulator of formula (I), or a pharmaceutically acceptable salt thereof, as defined above, may be administered in combination with one or more agents selected from:

- a selective Nav1.3 channel modulator, such as a compound disclosed in WO2008/118758;
- a selective Nav1.7 channel modulator, such as a compound disclosed in WO2010/079443, e.g. 4-[2-(5-amino-1H-pyrazol-4-yl)-4-chlorophenoxy]-5-chloro-2-fluoro-N-1,3-thiazol-4-ylbenzenesulfonamide or 4-[2-(3-amino-1H-pyrazol-4-yl)-4-(trifluoromethyl)phenoxy]-5-chloro-2-fluoro-N-1,3-thiazol-4-ylbenzenesulfonamide, or a pharmaceutically acceptable salt of either;
- a selective Nav1.8 channel modulator;
- a selective Nav1.9 channel modulator;
- a compound which modulates activity at more than one Nav channel, including a non-selective modulator such as bupivacaine, carbamazepine, lamotrigine, lidocaine, mexiletine or phenyloin;
- any inhibitor of nerve growth factor (NGF) signaling, such as: an agent that binds to NGF and inhibits NGF biological activity and/or downstream pathway(s) mediated by NGF signaling (e.g. tanezumab), a TrkA antagonist or a p75 antagoinsist, or an agent that inhibits downstream signaling in regard to NGF stimulated TrkA or P75 signalling;
- an inhibitor of neurotrophic pathways, where such inhibition is achieved by: (a) an agent that binds to nerve growth factor (NGF) (e.g. tanezumab, fasinumab or fulranumab), brain-derived neurotrophic factor (BDNF), neurotrophin-3 (NT-3) or neurotrophin-4 (NT-4), or to more than one of the aforementioned neurotrophins (e.g. soluble P75); or (b) an agent that inhibits receptor function at one or more of TrKA, TrKB, TrKC or P75, either at the orthosteric site, an allosteric site or by inhibition of the catalytic activity of the receptor(s);
- a compound which increases the levels of endocannabinoid, such as a compound with fatty acid amid hydrolase inhibitory (FAAH) or monoacylglycerol lipase (MAGL) activity;
- an analgesic, in particular paracetamol;
- an opioid analgesic, such as: buprenorphine, butorphanol, cocaine, codeine, dihydrocodeine, fentanyl, heroin, hydrocodone, hydromorphone, levallorphan levorphanol, meperidine, methadone, morphine, nalmefene, nalorphine, naloxone, naltrexone, nalbuphine, oxycodone, oxymorphone, propoxyphene or pentazocine;
- an opioid analgesic which preferentially stimulates a specific intracellular pathway, for example G-protein as opposed to beta arrestin recruitment, such as TRV130; an opioid analgesic with additional pharmacology, such as: noradrenaline (norepinephrine) reuptake inhibitory (NRI) activity, e.g. tapentadol; serotonin and norepinephrine reuptake inhibitory (SNRI) activity, e.g. tramadol; or nociceptin receptor (NOP) agonist activity, such as GRT6005;
- a nonsteroidal antiinflammatory drug (NSAID), such as a non-selective cyclooxygenase (COX) inhibitor, e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac; or a COX-2 selective inhibitor, e.g. celecoxib, deracoxib, etoricoxib, mavacoxib or parecoxib;
- a prostaglandin $E_2$ subtype 4 (EP4) antagonist;
- a microsomal prostaglandin E synthase type 1 (mPGES-1) inhibitor;
- a sedative, such as glutethimide, meprobamate, methaqualone or dichloralphenazone;
- a $GABA_A$ modulator with broad subtype modulatory effects mediated via the benzodiazepine binding site, such as chlordiazepoxide, alprazolam, diazepam, lorazepam, oxazepam, temazepam, triazolam, clonazepam or clobazam;
- a $GABA_A$ modulator with subtype-selective modulatory effects mediated via the benzodiazepine binding site with reduced adverse effects, for example sedation, such as TPA023, TPA023B, L-838,417, CTP354 or NSD72;
- a $GABA_A$ modulator acting via alternative binding sites on the receptor, such as barbiturates, e.g. amobarbital, aprobarbital, butabital, mephobarbital, methohexital, pentobarbital, phenobartital, secobarbital, or thiopental; neurosteroids such as alphaxalone, alphadolone or ganaxolone; β-subunit ligands, such as etifoxine; or δ-preferring ligands, such as gaboxadol;
- a GlyR3 agonist or positive allosteric modulator;
- a skeletal muscle relaxant, e.g. baclofen, carisoprodol, chlorzoxazone, cyclobenzaprine, metaxolone, methocarbamol or orphrenadine;
- a glutamate receptor antagonist or negative allosteric modulator, such as an NMDA receptor antagonist, e.g. dextromethorphan, dextrorphan, ketamine or, memantine; or an mGluR antagonist or modulator;
- an alpha-adrenergic, such as clonidine, guanfacine or dexmetatomidine;
- a beta-adrenergic such as propranolol;
- a tricyclic antidepressant, e.g. desipramine, imipramine, amitriptyline or nortriptyline;
- a tachykinin (NK) antagonist, such as aprepitant or maropitant;
- a muscarinic antagonist, e.g oxybutynin, tolterodine, propiverine, tropsium chloride, darifenacin, solifenacin, temiverine and ipratropium;
- a cholinergic (nicotinic) analgesic, such as ispronicline (TC-1734), varenicline or nicotine;
- a Transient Receptor Potential V1 (TRPV1) receptor agonist (e.g. resinferatoxin or capsaicin) or antagonist (e.g. capsazepine or mavatrap);
- a Transient Receptor Potential A1 (TRPA1) receptor agonist (e.g. cinnamaldehyde or mustard oil) or antagonist (e.g. GRC17536 or CB-625);
- a Transient Receptor Potential M8 (TRPM8) receptor agonist (e.g. menthol or icilin) or antagonist;
- a Transient Receptor Potential V3 (TRPV3) receptor agonist or antagonist (e.g. GRC-15300);
- a corticosteroid such as dexamethasone;
- a 5-HT receptor agonist or antagonist, particularly a $5-HT_{1B/1D}$ agonist, such as eletriptan, sumatriptan, naratriptan, zolmitriptan or rizatriptan;
- a $5-HT_{2A}$ receptor antagonist;
- a PDEV inhibitor, such sildenafil, tadalafil or vardenafil;
- an alpha-2-delta ligand such as gabapentin, gabapentin enacarbil or pregabalin;

a serotonin reuptake inhibitor (SRI) such as sertraline, demethylsertraline, fluoxetine, norfluoxetine, fluvoxamine, paroxetine, citalopram, desmethylcitalopram, escitalopram, d,l-fenfluramine, femoxetine, ifoxetine, cyanodothiepin, litoxetine, dapoxetine, nefazodone, cericlamine and trazodone;

an NRI, such as maprotiline, lofepramine, mirtazepine, oxaprotiline, fezolamine, tomoxetine, mianserin, buproprion, buproprion metabolite hydroxybuproprion, nomifensine and viloxazine, especially a selective noradrenaline reuptake inhibitor such as reboxetine;

an SNRI, such as venlafaxine, O-desmethylvenlafaxine, clomipramine, desmethylclomipramine, duloxetine, milnacipran and imipramine;

an inducible nitric oxide synthase (iNOS) inhibitor;

a leukotriene B4 antagonist;

a 5-lipoxygenase inhibitor, such as zileuton;

a potassium channel opener or positive modulator, such as an opener or positive modulator of KCNQ/Kv7 (e.g. retigabine or flupirtine), a G protein-coupled inwardly-rectifying potassium channel (GIRK), a calcium-activated potassium channel (Kca) or a potassium voltage-gated channel such as a member of subfamily A (e.g. Kv1.1), subfamily B (e.g. Kv2.2) or subfamily K (e.g. TASK, TREK or TRESK);

a $P2X_3$ receptor antagonist (e.g. AF219) or an antagonist of a receptor which contains as one of its subunits the $P2X_3$ subunit, such as a $P2X_{2/3}$ heteromeric receptor;

a $Ca_V2.2$ calcium channel blocker (N-type), such as ziconotide; and a $Ca_V3.2$ calcium channel blocker (T-type), such as ethosuximide.

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl)acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a $Na_V1.8$ modulator is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:

AcOH is acetic acid;
APCI is atmospheric pressure chemical ionisation mass spectrum;
Arbocel is a filter agent;
br is broad;
Celite® is a filter agent;
CDI is N,N'-carbonyldiimidazole;
$Cs_2CO_3$ is caesium carbonate;
$Cu(acac)_2$ is copper(II)acetylacetonate;
CuI is copper(I)iodide;
$Cu(OAc)_2$ is copper(II)acetate;
δ is chemical shift;
d is doublet;
DABCO is 1,4-diazabicyclo[2.2.2]octane;
DAD is diode array detector;
DCM is dichloromethane; methylene chloride;
DCC is N,N'-dicyclohexylcarbodiimide;
DDQ is 2,3-Dichloro-5,6-Dicyanobenzoquinone;
DIPEA is N-ethyldiisopropylamine, N,N-diisopropylethylamine;
DMAP is 4-dimethylaminopyridine;
DMF is N,N-dimethylformamide;
DMSO is dimethyl sulphoxide;
EDCl.HCl is 1-(3-dimethylaminopropyl)-3-ethylcarbodiimide hydrochloride;
EDCI.MeI is N-(3-dimethylaminopropyl)-N'-ethylcarbodiimide methyliodide;
EDTA is ethylenediaminetetraacetic acid;
ELSD is evaporative light scattering detection;
ES is electrospray ionization;
$Et_2O$ is diethyl ether;
EtOAc is ethyl acetate;
EtOH is ethanol;
HATU is 2-(7-azabenzotriazol-1-yl)-1,1,3,3-tetramethyluronium hexafluorophosphate;
HBTU is O-benzotriazol-1-yl-N,N,N',N'-tetramethyluronium hexafluorophosphate;
HCl is hydrochloric acid;
HOBT is N-hydroxybenzotriazole hydrate;
HPLC is high pressure liquid chromatography;
IPA is isopropanol;
$Ir_2(OMe)_2COD_2$ is bis(1,5-cyclooctadiene)di-μ-methoxydiiridium (I);
$K_2CO_3$ is potassium carbonate;
$KHSO_4$ is potassium hydrogen sulphate;
KOAc is potassium acetate;
KOH is potassium hydroxide;
$K_3PO_4$ is potassium phosphate tribasic;
L is liter LCMS is liquid chromatography mass spectrometry (R$_t$=retention time);
LiOH is lithium hydroxide;
m is multiplet;
MeOH is methanol;
2-MeTHF is 2-methyltetrahydrofuran;
MgSO$_4$ is magnesium sulphate;
m/z is mass spectrum peak;
NaH is sodium hydride;
NaHCO$_3$ is sodium hydrogencarbonate;
Na$_2$CO$_3$ is sodium carbonate;
NaHSO$_3$ is sodium bisulphite;
NaHSO$_4$ is sodium hydrogensulphate;
NaOH is sodium hydroxide;
Na$_2$SO$_4$ is sodium sulphate;
NBS is N-bromosuccinimide
NH$_4$Cl is ammonium chloride;
NMP is N-Methyl-2-pyrrolidone;
NMR is nuclear magnetic resonance;
Pd-118 is dichloro[1,1'bis(di-tert-butylphosphino)]ferrocene palladium(II);
PdCl$_2$(dtbpf) is dichloro[1,1'-bis(di-tert-butylphosphino)]ferrocene palladium(II);
Pd/C is palladium on carbon;
Pd(PPh$_3$)$_4$ is palladium tetrakis(triphenylphosphine);
Pd(dppf)$_2$Cl$_2$.DCM is [1,1'-bis(diphenylphosphino)ferrocene]dichloropalladium (II), complex with dichloromethane;
Pd$_2$(dba)$_3$ is tris(dibenzylideneacetone)dipalladium(0);
Pd(OAc)$_2$ is palladium acetate;
Pd(OH)$_2$/C is palladium hydroxide on carbon;
Prep is preparation;
POBr$_3$ is phosphorus oxybromide;
psi is pounds per square inch;
PyBop is (Benzotriazol-1-yloxy)tripyrrolidinophosphonium hexafluorophosphate;
q is quartet;
Rt is retention time;
s is singlet;
SPhos is 2-Dicyclohexylphosphino-2',6'-dimethoxybiphenyl;
t is triplet;
TBAF is tetrabutyl ammonium fluoride;
TBME is tert-butyl dimethyl ether;
THF is tetrahydrofuran;
THP is tetrahydropyran;
TLC is thin layer chromatography;
UV is ultraviolet; and
WSCDI is 1-(3-dimethylaminopropyl)-3-ethylcarbodiimide hydrochloride.

The Preparations and Examples that follow illustrate the invention but do not limit the invention in any way. All starting materials are available commercially or described in the literature. All temperatures are in ° C. Flash column chromatography was carried out using Merck silica gel 60 (9385). Thin layer chromatography (TLC) was carried out on Merck silica gel 60 plates (5729). "R$_f$" represents the distance travelled by a compound divided by the distance travelled by the solvent front on a TLC plate. Melting points were determined using a Gallenkamp MPD350 apparatus and are uncorrected. $^1$H-NMR spectra were recorded on a Varian Mercury 300 or 400 MHz, Bruker Avance 400 MHz NMR or Jeol ECX 400 MHz. NMR spectra were obtained as DMSO-d$_6$ solutions (reported in ppm). Other NMR solvents were used as needed. When peak multiplicities are reported, the following abbreviations are used: s=singlet, d=doublet, t=triplet, m=multiplet, br=broadened, dd=doublet of doublets, dt=doublet of triplets.

LCMS indicates liquid chromatography mass spectrometry (R$_t$=retention time). Where ratios of solvents are given, the ratios are by volume.

Mass spectra (MS) were recorded using either electrospray ionisation (ESI) or atmospheric pressure chemical ionisation (APCI). Mass spectroscopy was carried out using a Finnigan Navigator single quadrupole electrospray mass spectrometer, Finnigan aQa APCI mass spectrometer or Applied Biosystem Q-Trap.

Where it is stated that compounds were prepared in the manner described for an earlier Preparation or Example, the skilled person will appreciate that reaction times, number of equivalents of reagents and reaction temperatures may have been modified for each specific reaction, and that it may nevertheless be necessary, or desirable, to employ different work-up or purification conditions.

LCMS Systems

Where singleton compounds are analysed by LCMS, there are 16 methods used, shown below:
System 1
A: 0.1% formic acid in water
B: 0.1% formic acid in acetonitrile
Column: Agilent Extend C18 phase 50×3 mm with 3 micron particle size
Gradient: 95-0% A over 3.5 min, 1 min hold, 0.4 min re-equilibration, 1.2 mL/min flow rate
UV: 210 nm-450 nm DAD
Temperature: 50° C.
System 2
A: 0.1% formic acid in water
B: 0.1% formic acid in acetonitrile
Column: C18 phase Waters Sunfire 50×4.6 mm with 5 micron particle size
Gradient: 95-5% A over 3 min, 1 min hold, 2 min re-equilibration, 1 mL/min flow rate
UV: 210 nm-450 nm DAD
Temperature: 50° C.
System 3
A: 0.1% formic acid in water
B: 0.1% formic acid in acetonitrile
Column: C18 phase Phenomenex 20×4.0 mm with 3 micron particle size
Gradient: 98-2% A over 1.5 min, 0.3 min hold, 0.2 re-equilibration, 1.8 mL/min flow rate
UV: 210 nm-450 nm DAD
Temperature: 75° C.
System 4
A: 0.1% formic acid in water
B: 0.1% formic acid in 70% MeOH:30% IPA
Column: C18 phase Phenomenex 20×4.0 mm with 3 micron particle size
Gradient: 98-10% A over 1.5 min, 0.3 min hold, 0.2 re-equilibration, 2 mL/min flow rate
UV: 210 nm-450 nm DAD
Temperature: 75° C.
System 5
A: 0.05% formic acid in water
B: 0.05% formic acid in acetonitrile
Column: C18 phase Phenomenex Gemini, 50×4.60 mm with 3 micron particle size.
Gradient: 5% B to 95% B over 3.5 minutes. Hold to 4.5 minutes. 2.0 mL/min flow rate
UV: 200 nm-400 nm DAD
Temperature: 40° C.

System 6
A: water
B: acetonitrile
D: 1.0% formic acid in acetonitrile
Column: XBridge C18 2.1×30 mm with 5 micron particle size
Gradient: 5% B to 95% B over 2.3 minutes. Hold to 3.5 minutes. 1.0 mL/min flow rate
UV: 215 nm-350 nm DAD
Temperature: 25° C.
System 7
A: 10 mM Ammonium Acetate in water (basic Buffer)
B: Acetonitrile
Column: Xbridge C18 4.6×50 mm with 5 micron particle size
Gradient: from 90% [Buffer] and 10% [MeCN] to 70% [Buffer] and 30% [MeCN] in 1.5 min, further to 10% [buffer] and 90% [MeCN] in 3.0 min, held for 4 min and back to initial condition in 5 min),
1.2 mL/minflow rate
UV: 220 nm
Temperature: 25° C.
System 8
A: 0.1% Formic acid in water (v/v) [Buffer]
B: 0.1% Formic acid in acetonitrile (v/v) [MeCN]
Column: Phenomenex Gemini-NX C18 4.6×50 mm with 3 micron particle size
Gradient: From 95% [Buffer] and 5% [MeCN] to 0% [Buffer] and 100% [MeCN] from 0.0-4.1 min, held from 4.1-4.5 min and finally back to initial condition from 4.5-5.0 min, 1.5 mL/min flow rate
UV: 200 nm-450 nm DAD
Temperature: 60° C.
System 9
A: 0.05% Formic acid in water (acidic buffer)
B: Acetonitrile
Column: Gemini C18 4.6×50 mm with 5 micron particle size
Gradient: From 90% [Buffer] and 10% [MeCN] to 70% [Buffer] and 30% [MeCN] in 1.5 min, further to 10% [buffer] and 90% [MeCN] in 3.0 min, held for 4 min and finally back to initial condition in 5 min), 1.2 mL/min flow rate
UV: 220 nm
Temperature: 25° C.
System 10
A: 20 mM Ammonium formate in water (basic Buffer)
B: Acetonitrile
Column: Gemini-NX 5 μm C18 110A 50×4.6 mm column
Gradient: 5-95% A over 3.5 min, 1 min hold, 95-5% A over 0.1 min, 2 mL/min flow rate
UV: 210 nm-450 nm DAD 2 mL/min flow rate
UV: 260 nm
Temperature: 40° C.
System 11
A: 20 mM Ammonium formate in water (basic Buffer)
B: Acetonitrile
Column: XBridge C18 5 μm 50×4.6 mm column
Gradient: 5-95% A over 3.5 min, 1 min hold, 95-5% A over 0.1 min, 2 mL/min flow rate
UV: 210 nm-450 nm DAD 2 mL/min flow rate
Temperature: 25° C.
System 12
A: 0.05% Formic acid in water (acidic buffer)
B: 0.05% Formic acid in Acetonitrile
Column: Gemini-NX 5 μm C18 110A 50×4.6 mm column
5-95% A over 3.5 min, 1 min hold, 95-5% A over 0.1 min, 2 mL/min flow rate
UV: 210 nm-450 nm DAD 2 mL/min flow rate
Temperature: 40° C.

System 13
A: 0.05% Formic acid in water (acidic buffer)
B: 0.05% Formic acid in Acetonitrile
Column: XBridge C18 5 μm 50×4.6 mm column
5-95% A over 3.5 min, 1 min hold, 95-5% A over 0.1 min, 2 mL/min flow rate
UV: 210 nm-450 nm DAD 2 mL/min flow rate
Temperature: 25° C.
System 14
A: 0.1% formic acid in water (v/v)
B: 0.1% formic acid in acetonitrile (v/v)
Column: Acid: Waters Acquity UPLC BEH, 2.1 mm×50 mm, C18, 1.7 μm
Gradient Profiles: Flow-1.25 ml/min
1.5 min Run: Initial conditions: A-95%:B-5%; hold at initial from 0.0-0.1 min; Linear
Ramp to A-5%:B-95% over 0.1-1.0 min; hold at A-5%:B-95% from 1.0-1.1 min; return to initial conditions 1.1-1.5 min
Temperature: 60° C.
System 15
Column: Waters symmetry 2.1*50 mm 5 μm
Mobile phase: from 0% MeCN (0.1% TFA) in water (0.1% TFA) to 60% MeCN (0.1% TFA) in water (0.1% TFA)
Wavelength: 220 nm
System 16
A: 0.0375% TFA in water
B: 0.01875% TFA in MeCN
Column: Welch XB-C18 2.1×50 mm 5 μm
Gradient: From 99% [A] and 1% [B] to 95% [A] and 5% [B] in 1 min, further to 100% [B] in 4.0 min and finally back to initial condition in 4.30 min, 0.8 mL/minflow rate
UV: API-ES
Temperature 50° C.
Preparative HPLC:
Where singleton compounds are purified by preparative HPLC, there are two methods used, shown below:
Method 1 Acidic Conditions

| Column | Gemini NX C18, 5 um 21.2 × 100 mm |
|---|---|
| Temperature | Ambient |
| Detection | ELSD-MS |
| Mobile Phase A | 0.1% formic acid in water |
| Mobile Phase B | 0.1% formic acid in acetonitrile |
| Gradient | initial 0% B, 1 mins - 5% B; 7 mins - 98% B; 9 mins - 98% B; 9.1 mins - 5% B; 10 mins - 5% B |
| Flow rate | 18 mL/min |
| Injection volume | 1000 uL |

Method 2 Basic Conditions

| Column | Gemini NX C18, 5 um 21.2 × 100 mm |
|---|---|
| Temperature | Ambient |
| Detection | ELSD-MS |
| Mobile Phase A | 0.1% diethylamine in water |
| Mobile Phase B | 0.1% diethylamine in acetonitrile |
| Gradient | initial 0% B, 1 mins - 5% B; 7 mins - 98% B; 9 mins - 98% B; 9.1 mins - 5% B; 10 mins - 5% B |
| Flow rate | 18 mL/min |
| Injection volume | 1000 uL |

Example 1

7-Ethyl-4-[6-fluoro-4'-(propan-2-ylsulfonyl)biphenyl-3-yl]-7H-imidazo[4,5-c]pyridazine

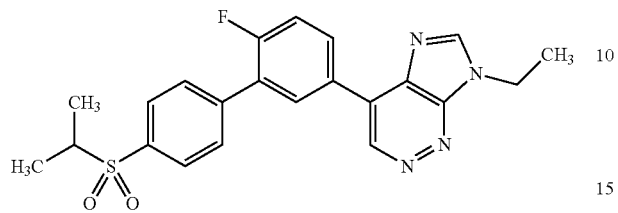

To a solution of 7-ethyl-4-(4-fluoro-3-iodophenyl)-7H-imidazo[4,5-c]pyridazine (Preparation 10, 41 mg, 0.11 mmol) and 4-(isopropylsulfonyl)phenylboronic acid (38 mg, 0.17 mmol) in anhydrous dioxane (2.0 mL) was added aqueous $Na_2CO_3$ (1M solution, 0.56 mL, 0.56 mmol) and the solution was degassed.

Tetrakis(triphenylphosphine)palladium(0) (6.9 mg, 0.0060 mmol) was added and the reaction mixture was heated to 100° C. for 2 hours. The reaction was allowed to cool to room temperature, then EtOAc (10 mL) and water (10 mL) were added. The layers were separated and the organic layer was dried over anhydrous $MgSO_4$, filtered and evaporated in vacuo. The residue was purified by preparative HPLC (Method 1) to afford the title compound in 64% yield, 29.7 mg.

LCMS (System 6) Rt=1.47 minutes MS m/z 425 $[M+H]^+$

Example 2

4-[2',6-Difluoro-4'-(methylsulfonyl)biphenyl-3-yl]-7-ethyl-7H-imidazo[4,5-c]pyridazine

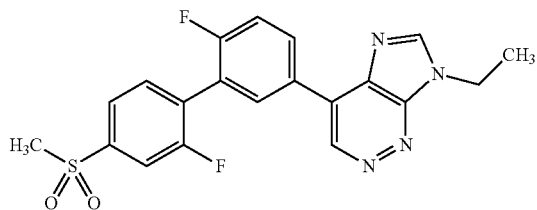 [SMILES: CCn1cnc2c(-c3ccc(F)c(-c4ccc(S(C)(=O)=O)cc4F)c3)cnnc21]

Prepared according to the method described above for Example 1 using 4-(3-iodo-4-fluorophenyl)-7-ethyl-7H-imidazo[4,5-c]pyridazine (Preparation 11, 50 mg, 0.16 mmol) and 2-fluoro-4-(methylsulfonyl)phenylboronic acid (68 mg, 0.31 mmol).

The crude product was purified by silica gel column chromatography eluting with EtOAc to afford the title compound as a white solid in 83% yield, 53.8 mg.

$^1$H-NMR (400 MHz, $CDCl_3$): δ ppm 1.69 (t, 3H), 3.14 (s, 3H), 4.59 (q, 2H), 7.43 (dd, 1H), 7.72 (dd, 1H), 7.79-7.83 (m, 1H), 7.85-7.88 (m, 1H), 8.28-8.32 (m, 1H), 8.29 (s, 1H), 8.32-8.36 (m, 1H), 9.38 (s, 1H).

LCMS (System 5) Rt=1.19 minutes MS m/z 415 $[M+H]^+$

Example 3

5'-(7-Ethyl-7H-imidazo[4,5-c]pyridazin-4-yl)-2'-fluorobiphenyl-4-sulfonamide

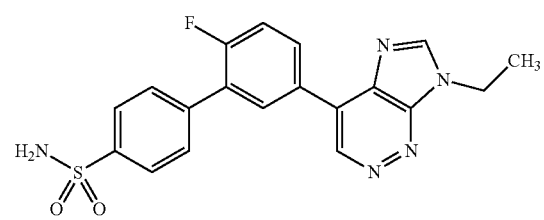 [SMILES: CCn1cnc2c(-c3ccc(F)c(-c4ccc(S(N)(=O)=O)cc4)c3)cnnc21]

Prepared according to the method described above for Example 1 using 7-ethyl-4-(4-fluoro-3-iodophenyl)-7H-imidazo[4,5-c]pyridazine (Preparation 10) and 4-(4,4,5,5-tetramethyl-1,3,2-dioxaborolan-2-yl)benzenesulfonamide (Preparation 80) to afford the title compound in 57% yield, 24.8 mg.

LCMS (System 6) Rt=1.27 minutes MS m/z 398 $[M+H]^+$

Example 4

7-Ethyl-4-[4'-(ethylsulfonyl)-6-fluoro-2'-methoxybiphenyl-3-yl]-7H-imidazo[4,5-c]pyridazine

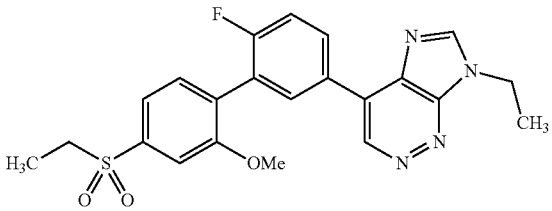 [SMILES: CCn1cnc2c(-c3ccc(F)c(-c4ccc(S(=O)(=O)CC)cc4OC)c3)cnnc21]

A stirred solution of 7-ethyl-4-(4-fluoro-3-iodophenyl)-7H-imidazo[4,5-c]pyridazine (Preparation 10, 100 mg, 0.27 mmol), 2-(4-ethylsulfonyl-2-methoxyphenyl)-4,4,5,5-tetramethyl-[1,3,2]dioxaborolane (Preparation 21, 88 mg, 0.27 mmol) and cesium carbonate (177 mg, 0.54 mmol) in dioxane (5 mL) and water (1 mL) was degassed with argon for 10 minutes followed by the addition of 1,1'-bis(di-tert-butylphosphino) ferrocene palladium dichloride (4.4 mg, 0.005 mmol). The resulting mixture was heated at 100° C. for 16 hours, cooled to room temperature and diluted with EtOAc (15 mL). The organic layer was washed with water (10 mL) and saturated brine solution (10 mL) then dried over $Na_2SO_4$, filtered and concentrated in vacuo. Purification by silica gel column chromatography eluting with $CH_2Cl_2$:MeOH 98:2 afforded the title compound as off white solid in 13% yield, 15 mg.

$^1$H NMR (400 MHz, $CDCl_3$): δ ppm 1.36 (t, 3H), 1.68 (t, 3H), 3.18 (q, 2H), 3.90 (s, 3H), 4.58 (q, 2H), 7.35 (t, 1H), 7.50 (s, 1H), 7.54-7.60 (m, 2H), 8.21 (dd, 1H), 8.26 (s, 1H), 8.27-8.29 (m, 1H), 9.35 (s, 1H).

LCMS (System 7) Rt=2.94 minutes MS m/z=441 $[M+H]^+$

Example 5

5'-(7-Ethyl-7H-imidazo[4,5-c]pyridazin-4-yl)-2'-fluoro-4-(isopropylsulfonyl)-[1,1'-biphenyl]-2-carbonitrile

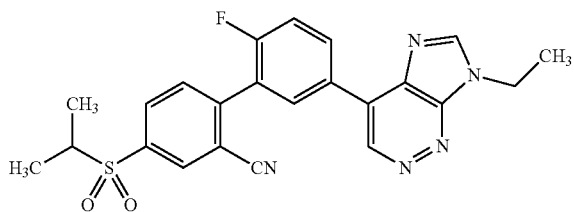 [SMILES: CCn1cnc2c(-c3ccc(F)c(-c4ccc(S(=O)(=O)C(C)C)cc4C#N)c3)cnnc21]

A solution of 6-(3-bromo-4-fluorophenyl)-9-ethyl-9H-imidazo[4,5-c]pyridazine (Preparation 11, 58 mg, 0.18 mmol), bis(pinacolato)diboron (69 mg, 0.27 mmol) and potassium acetate (35 mg, 0.35 mmol) in dioxane (5.0 mL) at room temperature was purged with nitrogen gas for 30 minutes. [1,1'-bis(diphenylphosphino)ferrocene]dichloropalladium(II) (15 mg, 0.02 mmol) was added to the reaction mixture, which was purged with nitrogen gas for a further 10 minutes. The reaction mixture was heated under reflux at 110° C. for 3 hours. The reaction was cooled to 40° C. and 2-bromo-5-(isopropylsulfonyl)benzonitrile, (Preparation 25, 60 mg, 0.21 mmol), sodium carbonate (74 mg, 0.70 mmol) in $H_2O$ (0.3 mL) and [1,1'-bis(diphenylphosphino) ferrocene]dichloropalladium(II) (16.0 mg, 0.02 mmol) were added and the reaction mixture was purged with nitrogen gas for 30 minutes. The reaction mixture was heated at 110° C. for 16 hours. The reaction mixture was filtered through a pad of celite, eluting with EtOAc (20 mL). The filtrate was washed with water (20 mL), brine (10 mL), dried over $Na_2SO_4$ and concentrated under reduced pressure to give a dark brown oil. The oil was purified by silica gel column chromatography eluting with EtOAc to afford the title compound as a pale yellow oil. The material was further purified by silica gel column chromatography eluting with EtOAc:$CH_2Cl_2$:MeOH 1:1:0.1 followed by elution through an SCX-2 cartridge using $CH_2Cl_2$, MeOH and $NH_3$/MeOH. The title compound was obtained as an off-white solid, 26% yield, 21 mg. $^1$H NMR (400 MHz, CDCl$_3$): δ ppm 1.39 (d, 6H), 1.70 (t, 3H) 3.30 (q, 2H) 4.61 (m, 1H) 7.50 (m, 1H) 7.85 (m, 1H) 8.19 (m, 1H) 8.33-8.43 (m, 4H) 9.45 (s, 1H).

LCMS (System 12) Rt=2.46 minutes MS m/z 450 [M+H]$^+$

Example 6

4-(4'-(Cyclobutylsulfonyl)-6-fluoro-2'-methoxy-[1,1-biphenyl]-3-yl)-7-ethyl-7H-imidazo[4,5-c]pyridazine

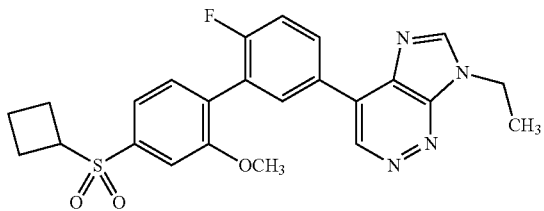 [SMILES: CCn1cnc2c(-c3ccc(F)c(-c4ccc(S(=O)(=O)C5CCC5)cc4OC)c3)cnnc21]

A mixture of 6-(3-bromo-4-fluorophenyl)-9-ethyl-9H-imidazo[4,5-c]pyridazine (Preparation 11, 50 mg, 0.156 mmol), 2-(4-(cyclobutylsulfonyl)-2-methoxyphenyl)-4,4,5,5-tetramethyl-1,3,2-dioxaborolane (Preparation 30, 82 mg, 0.233 mmol) and sodium carbonate (50 mg, 0.468 mmol) in dioxane (2.5 mL) and water (0.5 mL) was purged with nitrogen for 10 minutes. Tetrakis(triphenylphosphine)palladium (0) (18 mg, 0.02 mmol) was added and the reaction heated at 98° C. for 16 hours. The mixture was diluted with $CH_2Cl_2$ (30 mL), washed with water (10 mL), dried over $Na_2SO_4$ and concentrated in vacuo. The resulting gum was purified by silica gel column chromatography eluting with EtOAc followed by preparative HPLC to afford the title compound as a white solid 44% yield, 32 mg.

$^1$H NMR (400 MHz, CDCl$_3$): δ ppm 1.70 (t, 3H), 2.05 (m, 2H), 2.27 (m, 2H), 2.65 (m, 2H), 2.82-2.95, (m, 4H), 4.61 (q, 2H), 6.38 (m, 1H), 6.42-6.58 (m, 3H), 8.25 (m, 1H), 8.33 (m, 1H), 8.42 (s, 1H), 9.42 (s, 1H).

LCMS (System 11) Rt=2.88 minutes MS m/z 467 [M+H]$^+$

Example 7

4-(4'-(Cyclopropylsulfonyl)-6-fluoro-2'-methoxy-[1,1'-biphenyl]-3-yl)-7-ethyl-7H-imidazo[4,5-c]pyridazine

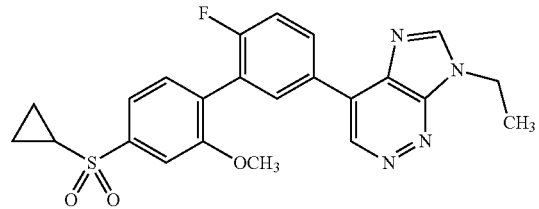 [SMILES: CCn1cnc2c(-c3ccc(F)c(-c4ccc(S(=O)(=O)C5CC5)cc4OC)c3)cnnc21]

Step 1

To a degassed solution of 1-bromo-4-(cyclopropylsulfonyl)-2-methoxybenzene (Preparation 33, 85 mg, 0.29 mmol), bis(pinacolato)diboron (111 mg, 0.44 mmol) and potassium acetate (86 mg, 0.88 mmol) in dioxane (2 mL) was added 1,1'-bis(diphenylphosphino)ferrocene-palladium(II)dichloride (24 mg, 0.03 mmol). The resulting mixture was stirred at 100° C. for 3 hours.

Step 2

After cooling to room temperature, 6-(3-bromo-4-fluorophenyl)-9-ethyl-9H-imidazo[4,5-c]pyridazine (Preparation 11, 84 mg, 0.26 mmol), sodium carbonate (96 mg, 0.88 mmol) and water (0.5 mL) were added, and the resulting mixture degassed and flushed with nitrogen gas, followed by addition of tetrakis(triphenylphosphine) palladium(0) (34 mg, 0.03 mmol). After stirring at 90° C. for 1.5 hours, the mixture was cooled to room temperature and left to stand for 16 hours. Water (3 mL) and ethyl acetate (3 mL) were added, and the resulting mixture passed through a short pad of arbocel, then partitioned. The aqueous was extracted with ethyl acetate (2×3 mL), and the combined organic layers dried over MgSO$_4$ then concentrated in vacuo. Purification by silica gel column chromatography eluting with 1:39:60 MeOH/EtOAc/$CH_2Cl_2$ yielded a brown solid that was triturated with methanol to afford the title compound as an off-white solid 37% yield, 49 mg, $^1$H NMR (400 MHz, CDCl$_3$): δ ppm 1.15 (m, 2H), 1.41 (m, 2H), 1.71 (t, 3H), 2.54 (m, 1H), 3.91 (s, 3H), 4.59 (q, 2H), 7.40 (t, 1H), 7.53 (m, 2H), 7.60 (m, 1H), 8.30 (m, 1H), 8.36 (m, 1H), 8.47 (s, 1H), 9.46 (s, 1H).

LCMS (System 12): Rt=2.51 minutes MS m/z 453 [M+H]+

Examples 8-15 were prepared according to the method described above for Example 7 using either Step 1 and Step 2 combined or just Step 2 alone as described, using 6-(3-bromo-4-fluorophenyl)-9-ethyl-9H-imidazo[4,5-c]pyridazine (Preparation 11) or 4-chloro-7-ethyl-7H-imidazo[4,5-c]pyridazine (Preparation 8) and the appropriate aryl bromide or boronic ester as described.

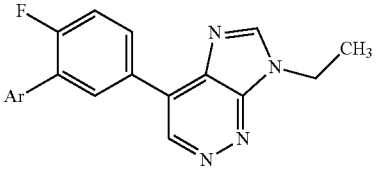

| Example | | |
|---|---|---|
| 8 | 5'-(7-Ethyl-7H-imidazo[4,5-c]pyridazin-4-yl)-2'-fluoro-N-methylbiphenyl-4-sulfonamide | |
| | Ar = 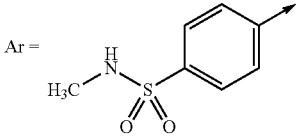 | Using 4-bromo-N-methylbenzenesulfonamide.<br>LCMS (System 16): Rt = 2.73 min<br>MS m/z 412 [M + H]+ |
| 9 | 7-Ethyl-4-[6-fluoro-4'-(methylsulfonyl)biphenyl-3-yl]-7H-imidazo[4,5-c]pyridazine | |
| | Ar = 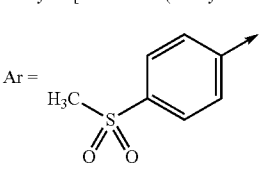 | Using 4-bromophenylmethylsulfone<br>LCMS (System 16): Rt = 2.70 min<br>MS m/z 397 [M + H]+ |
| 10 | 4-(2',6-Difluoro-4'-(isopropylsulfonyl)-[1,1'-biphenyl]-3-yl)-7-ethyl-7H-imidazo[4,5-c]pyridazine | |
| | Ar = 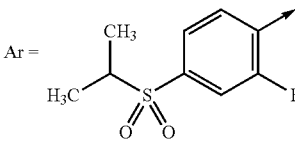 | Using 1-bromo-2-fluoro-4-(isopropylsulfonyl)-benzene (Preparation 34)<br>LCMS (System 11): Rt = 2.60 min<br>MS m/z 443 [M + H]+ |
| 11 | 5'-(7-Ethyl-7H-imidazo[4,5-c]pyridazin-4-yl)-4-(ethylsulfonyl)-2'-fluoro-[1,1'-biphenyl]-2-carbonitrile | |
| | Ar = 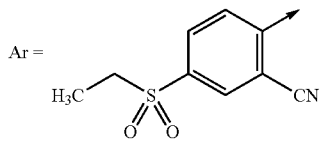 | Using 4-(ethylsulfonyl)-2'-fluoro-5'-(4,4,5,5-tetramethyl-1,3,2-dioxaborolan-2-yl)-[1,1'-biphenyl]-2-carbonitrile (Preparation 79) and Step 2<br>LCMS (System 13): Rt = 2.42 min<br>MS m/z 436 [M + H]+ |
| 12 | 7-Ethyl-4-(6-fluoro-2'-methoxy-4'-(methylsulfonyl)-[1,1'-biphenyl]-3-yl)-7H-imidazo[4,5-c]pyridazine | |
| | Ar = 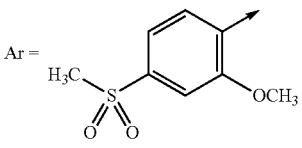 | Using 2-(6-fluoro-2'-methoxy-4'-(methylsulfonyl)-[1,1'-biphenyl]-3-yl)-4,4,5,5-tetramethyl-1,3,2-dioxaborolane (Preparation 18) and Step 2<br>LCMS (System 11): Rt = 2.18 min<br>MS m/z 427 [M + H]+ |
| 13 | 7-Ethyl-4-(6-fluoro-4'-(isopropylsulfonyl)-2'-methoxy-[1,1'-biphenyl]-3-yl)-7H-imidazo[4,5-c]pyridazine | |
| | Ar = 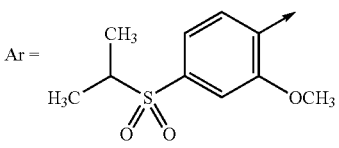 | Using 2-(6-fluoro-4'-(isopropylsulfonyl)-2'-methoxy-[1,1'-biphenyl]-3-yl)-4,4,5,5-tetramethyl-1,3,2-dioxaborolane (Preparation 38) and Step 2<br>LCMS (System 11): Rt = 2.44 min<br>MS m/z 455 [M + H]+ |

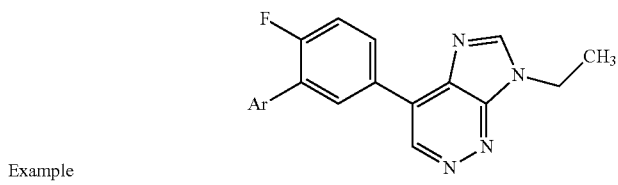

| Example | |
|---|---|
| 14 | 4-(2'-(Difluoromethyl)-4'-(ethylsulfonyl)-6-fluoro-[1,1'-biphenyl]-3-yl)-7-ethyl-7H-imidazo[4,5-c]pyridazine |

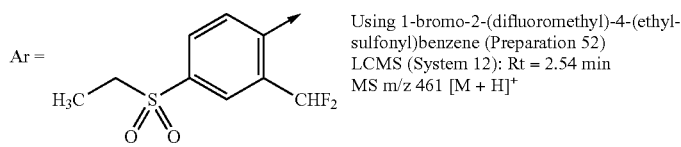

Ar =

Using 1-bromo-2-(difluoromethyl)-4-(ethylsulfonyl)benzene (Preparation 52)
LCMS (System 12): Rt = 2.54 min
MS m/z 461 [M + H]$^+$

| 15 | 4-(4'-Ethanesulfonyl-6,2'-difluoro-biphenyl-3-yl)-7-ethyl-7H-imidazo[4,5-c]pyridazine |
|---|---|

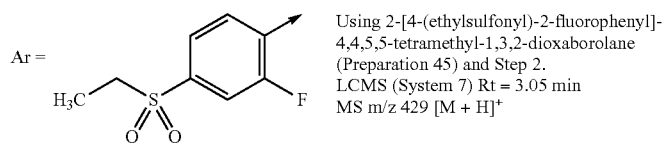

Ar =

Using 2-[4-(ethylsulfonyl)-2-fluorophenyl]-4,4,5,5-tetramethyl-1,3,2-dioxaborolane (Preparation 45) and Step 2.
LCMS (System 7) Rt = 3.05 min
MS m/z 429 [M + H]$^+$ Examples 16 and 17 were prepared according to the method described above for Step 2 Example 7, using 3-(7-ethyl-7H-imidazo[4,5-c]pyridazin-4-yl)benzene boronic acid (Preparation 63), cesium carbonate as base, and the appropriate aryl bromide as described. The crude residues were purified by preparative HPLC (Method 1) eluting from between 33-67% organic over a gradient time of 10 minutes. LCMS conditions used: System 16

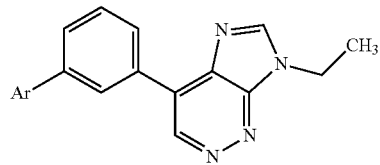

| Example | |
|---|---|
| 16 | 7-Ethyl-4-[4'-(methylsulfonyl)biphenyl-3-yl]-7H-imidazo[4,5-c]pyridazine |

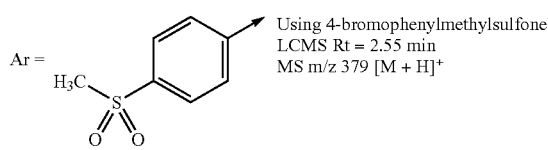

Ar =

Using 4-bromophenylmethylsulfone
LCMS Rt = 2.55 min
MS m/z 379 [M + H]$^+$

| 17 | 4-[3-(1,1-dioxido-2,3-dihydro-1-benzothiophen-5-yl)phenyl]-7-ethyl-7H-imidazo[4,5-c]pyridazine |
|---|---|

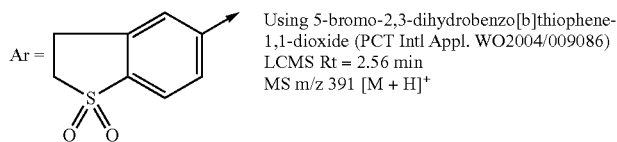

Ar =

Using 5-bromo-2,3-dihydrobenzo[b]thiophene-1,1-dioxide (PCT Intl Appl. WO2004/009086)
LCMS Rt = 2.56 min
MS m/z 391 [M + H]$^+$

Example 18

5'-(7-cyclopropyl-7H-imidazo[4,5-d]pyridazin-4-yl)-2'-fluoro-4-(isopropylsulfonyl)-[1,1'-biphenyl]-2-carbonitrile

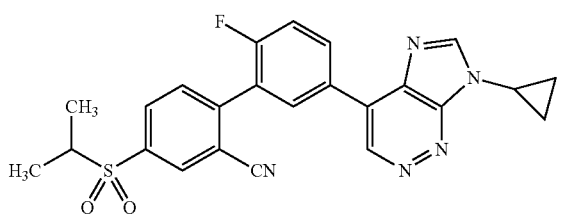 [SMILES: CC(C)S(=O)(=O)c1ccc(-c2cc(-c3cnnc4c3ncn4C3CC3)ccc2F)c(C#N)c1]

Step 1

A solution of 6-(3-bromo-4-fluorophenyl)-9-cyclopropyl-9H-imidazo[4,5-c]pyridazine (Preparation 84, 50.0 mg, 0.150 mmol), bis(pinacolato)diboron (57.0 mg, 0.23 mmol), potassium acetate (29.0 mg, 0.30 mmol) in dioxane (3.5 mL) at room temperature was purged with nitrogen for 30 minutes. [1,1'-bis(diphenylphosphino) ferrocene]dichloropalladium (II) (11.0 mg, 0.02 mmol) was added to the reaction mixture, which was further purged with nitrogen for 20 minutes. The reaction mixture was heated to reflux for 62 hours.

Step 2

The reaction was cooled to room temperature and 2-bromo-5-(isopropylsulfonyl)benzonitrile (Preparation 25, 48.0 mg, 0.165 mmol), sodium carbonate (56.0 mg, 0.530 mmol) in water (0.2 mL) was added. The mixture was purged with nitrogen for 20 minutes. [1,1'-Bis(diphenylphosphino) ferrocene]dichloropalladium(II) (11.0 mg, 0.0150 mmol) was added and the mixture was purged with nitrogen for 10 minutes and heated to 110° C. The reaction mixture was cooled to room temperature after 1.5 hours, filtered through celite and concentrated in vacuo. Te residue was purified using silica gel column chromatography eluting with EtOAc/heptanes 1:1 to 1:0 to afford an orange solution which crystallised upon concentration. The solid was washed with EtOAc (3×5 mL) before being diluted in acetonitrile and concentrated in vacuo 3 times. The title compound was afforded as an off-white solid 13% yield, 10 mg.

$^1$H NMR (400 MHz, CDCl$_3$): δ ppm 1.25 (br s, 2H), 1.30-1.39 (m, 8H), 3.29 (m, 1H), 3.70 (br s, 1H), 7.48 (t, 1H), 7.84 (d, 1H), 8.18 (d, 1H), 8.30 (s, 1H), 8.32-8.45 (m, 3H), 9.49 (s, 1H).

$^{19}$F NMR (376 MHz, CDCl$_3$ with drop of CD$_3$OD): δ −111.27 ppm.

LCMS (System 13): Rt=2.59 minutes MS m/z 462 [M+H]$^+$

Example 19

7-Cyclopropyl-4-[4'-(ethylsulfonyl)-6-fluorobiphenyl-3-yl]-7H-imidazo[4,5-c]pyridazine

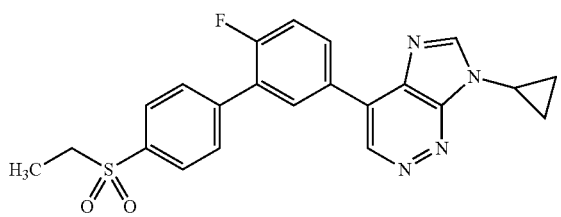 [SMILES: CCS(=O)(=O)c1ccc(-c2cc(-c3cnnc4c3ncn4C3CC3)ccc2F)cc1]

4-Ethylsulfonylphenyl boronic acid (19 mg, 0.09 mmol) and 6-(3-bromo-4-fluorophenyl)-9-cyclopropyl-9H-imidazo[4,5-c]pyridazine (Preparation 84, 25 mg, 0.075 mmol) were reacted as described in Example 18 to afford the title compound as a pale yellow solid in 38% yield, 12 mg.

$^1$H NMR (400 MHz, CDCl$_3$): δ ppm 1.24-1.35 (m, 7H), 3.17 (q, 2H), 3.69-3.72 (m, 1H), 7.40 (t, 1H), 7.83 (d, 2H), 8.01 (d, 2H), 8.18-8.20 (m, 1H), 8.26 (s, 1H), 8.37 (dd, 1H), 9.39 (s, 1H).

LCMS (System 7): Rt=2.99 minutes MS m/z 423 [M+H]$^+$

Examples 20 to 25 were prepared according to the method described above for Example 18, using 6-(3-bromo-4-fluorophenyl)-9-cyclopropyl-9H-imidazo[4,5-c]pyridazine (Preparation 84) or 6-(3-iodo-4-fluorophenyl)-9-cyclopropyl-9H-imidazo[4,5-c]pyridazine (Preparation 94) or an alternative as described and the appropriate boronic acid or ester as described.

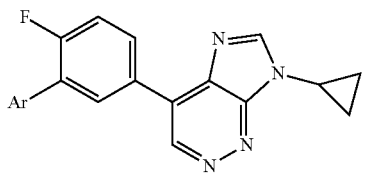

| Example | | |
|---|---|---|
| 20 | 5'-(7-Cyclopropyl-7H-imidazo[4,5-c]pyridazin-4-yl)-2'-fluoro-[1,1'-biphenyl]-4-sulfonamide | |
| | Ar = 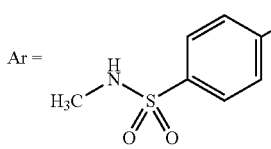 | Using 4-bromo-N-methylbenzenesulfonamide<br>LCMS (System 11) Rt = 2.32 min<br>MS m/z = 410 [M + H]$^+$ |

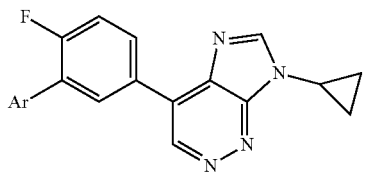

| Example | | |
|---|---|---|
| 21 | 7-Cyclopropyl-4-(6-fluoro-4'-(methylsulfonyl)biphenyl-3-yl)-7H-imidazo[4,5-c]pyridazine | |
| | 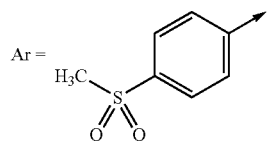  Ar = | Using 6-(3-chloro-4-fluorophenyl)-9-cyclopropyl-9H-imidazo[4,5-c]pyridazine (Preparation 92) and 4-(4,4,5,5-tetramethyl-1,3,2-dioxaborolan-2-yl)benzenesulfonamide (Preparation 80) and Step 2 using palladium acetate, cataCXium A and cesium fluoride in methanol<br>LCMS (System 14): Rt = 0.74 mins<br>MS m/z 409 [M + H]$^+$ |
| 22 | 7-Cyclopropyl-4-(4'-(ethylsulfonyl)-2',6-difluoro-[1,1'-biphenyl]-3-yl)-7H-imidazo[4,5-c]pyridazine | |
| | 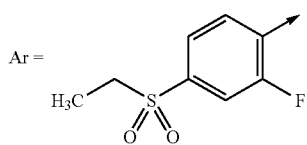  Ar = | Using 2-[4'-(ethylsulfonyl)-2',6-difluoro-biphenyl-3-yl]-4,4,5,5-tetramethyl-1,3,2-dioxaborolane (Preparation 47) and 4-chloro-7-cyclopropyl-7H-imidazo[4,5-c]pyridazine (Preparation 91) and Step 2<br>LCMS (System 13): Rt = 2.55 min<br>MS m/z 441 [M + H]$^+$ |
| 23 | 7-Cyclopropyl-4-(6-fluoro-4'-(isopropylsulfonyl)-2'-methoxy-[1,1'-biphenyl]-3-yl)-7H-imidazo[4,5-c]pyridazine | |
| | 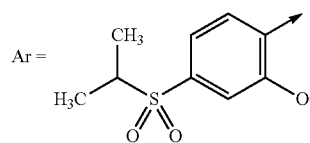  Ar = | Using 2-(4-(isopropylsulfonyl)-2-methoxy-phenyl)-4,4,5,5-tetramethyl-1,3,2-dioxaborolane (Preparation 36) and Step 2.<br>LCMS (System 13): Rt = 2.62 min<br>MS m/z 467 [M + H]$^+$ |
| 24 | 7-Cyclopropyl-4-(6-fluoro-2'-methoxy-4'-(methylsulfonyl)-[1,1'-biphenyl]-3-yl)-7H-imidazo[4,5-c]pyridazine | |
| | 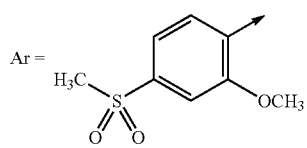  Ar = | Using 2-(6-fluoro-2'-methoxy-4'-(methylsulfonyl)-[1,1'-biphenyl]-3-yl)-4,4,5,5-tetramethyl-1,3,2-dioxaborolane (Preparation 18) and 4-chloro-7-cyclopropyl-7H-imidazo[4,5-c]pyridazine (Preparation 91) and Step 2.<br>LCMS System 13): Rt = 2.42 min<br>MS m/z 439 [M + H]$^+$ |
| 25 | 5'-(7-Cyclopropyl-7H-imidazo[4,5-c]pyridazin-4-yl)-4-(ethylsulfonyl)-2'-fluoro-[1,1'-biphenyl]-2-carbonitrile | |
| | 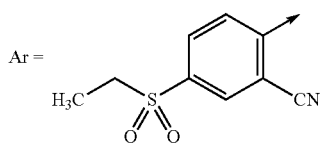  Ar = | Using 2-bromo-5-(ethylsulfonyl)benzonitrile (Preparation 75).<br>LCMS (System 13): Rt = 2.45 min<br>MS m/z 448 [M + H]$^+$ |

Example 26

7-Cyclobutyl-4-(4'-(ethylsulfonyl)-2',6-difluoro-[1,1'-biphenyl]-3-yl)-7H-imidazo[4,5-c]pyridazine

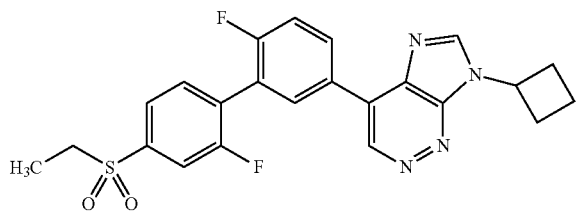 [SMILES: CCS(=O)(=O)c1ccc(-c2cc(-c3cnnc4c3ncn4C3CCC3)ccc2F)c(F)c1]

A solution of 2-(4'-(ethylsulfonyl)-2',6-difluoro-[1,1'-biphenyl]-3-yl)-4,4,5,5-tetramethyl-1,3,2-dioxaborolane (Preparation 83, 64 mg, 0.16) in dioxane (2.5 mL) was added to 6-chloro-9-cyclobutyl-9H-imidazo[4,5-c]pyridazine (Preparation 99, 33 mg, 0.16 mmol), tetrakis(triphenylphosphine)palladium(0) (18 mg, 0.016 mmol), sodium carbonate (50 mg, 0.471 mmol) and water (0.5 mL). Nitrogen gas was bubbled through the solution for 10 minutes, and the reaction was then warmed to 80° C. and stirred for 18 hours. The reaction was cooled, diluted with EtOAc (10 mL), filtered through a pad of celite washing with EtOAc (10 mL). The organic layers were washed with water (10 mL) and brine (10 mL), dried over MgSO$_4$, filtered and the solvent removed in vacuo. The crude material was passed through a SCX-2 cartridge washing first with MeOH, and then 25% 7M NH$_3$ (in MeOH) in MeOH (50 mL). The residue was further purified by preparative HPLC (System X) to afford the title compound as an off-white solid 15% yield, 11 mg.

$^1$H NMR (400 MHz, DMSO-d$_6$): δ ppm 1.18 (t, 3H), 1.92-2.00 (m, 2H), 2.56 (m, 2H), 2.82 (m, 2H), 3.46 (q, 2H), 5.33 (m, 1H), 7.66 (m, 1H), 7.92 (m, 3H), 8.62 (m, 2H), 9.02 (s, 1H), 9.61 (s, 1H).

$^{19}$F NMR (376 MHz, DMSO-d$_6$): δ −111.4 (m, 1F), −112.6 (m, 1F) ppm.

LCMS (System 13): Rt=2.77 min; m/z=455 [M+H]$^+$

Example 27

4-[4'-(Ethylsulfonyl)-6-fluorobiphenyl-3-yl]-7-(1-methylcyclopropyl)-7H-imidazo[4,5-c]pyridazine

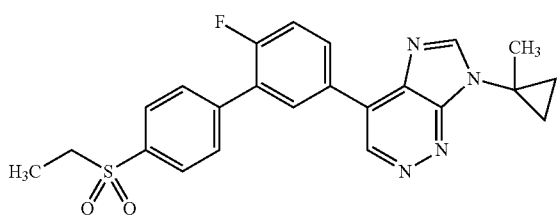 [SMILES: CCS(=O)(=O)c1ccc(-c2cc(-c3cnnc4c3ncn4C3(C)CC3)ccc2F)cc1]

Prepared according to the method described for Example 26 using 4-chloro-7-(1-methylcyclopropyl)-7H-imidazo[4,5-c]pyridazine (Preparation 97) and 2-(4'-ethylsulfonyl-6-fluorobiphenyl-3-yl)-4,4,5,5-tetramethyl[1,3,2]dioxaborolane (Preparation 48) to afford the title compound as an off white solid in 32% yield, 20 mg $^1$H NMR (400 MHz, CDCl$_3$): δ ppm 1.02 (t, 3H), 1.33 (t, 3H), 2.06-2.12 (m, 2H), 3.16 (q, 2H), 4.48 (q, 2H), 7.40 (t, 1H), 7.84 (d, 2H), 8.01 (d, 2H), 8.21-8.23 (t, 1H), 8.25 (s, 1H), 8.42 (dd, 1H), 9.37 (s, 1H).

LCMS (System 7): Rt=3.10 minutes MS m/z 437 [M+H]$^+$

Example 28

7-Cyclobutyl-4-[4'-(ethylsulfonyl)-6-fluorobiphenyl-3-yl]-7H-imidazol[4,5-c]pyridazine

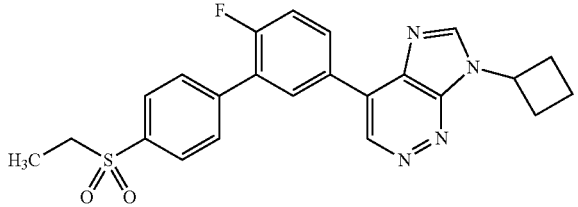 [SMILES: CCS(=O)(=O)c1ccc(-c2cc(-c3cnnc4c3ncn4C3CCC3)ccc2F)cc1]

Prepared according to the method described for Example 26 using 4-chloro-7-cyclobutyl-7H-imidazo[4,5-c]pyridazine (Preparation 99) and 2-(4'-ethylsulfonyl-6-fluorobiphenyl-3-yl)-4,4,5,5-tetramethyl-[1,3,2]dioxaborolane (Preparation 48) to afford the title compound as an off white solid in 10% yield, 10 mg.

$^1$H NMR (400 MHz, CDCl$_3$): δ ppm 1.33 (t, 3H), 2.01-2.11 (m, 2H), 2.71-2.83 (m, 4H), 3.16 (q, 2H), 5.28-5.34 (m, 1H), 7.40 (t, 1H), 7.83 (d, 2H), 8.01 (d, 2H), 8.21-8.23 (m, 1H), 8.34 (s, 1H), 8.39 (d, 1H), 9.36 (s, 1H).

LCMS (System 7): Rt=3.35 minutes MS m/z 437 [M+H]$^+$

Example 29

7-Cyclobutyl-4-(6-fluoro-2'-methoxy-4'-(methylsulfonyl)-[1,1'-biphenyl]-3-yl)-7H-imidazol[4,5-c]pyridazine

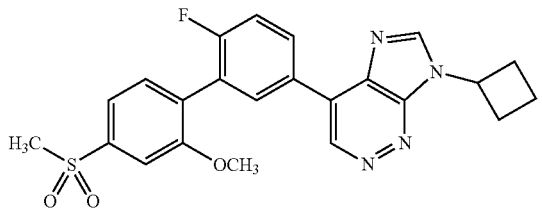 [SMILES: COc1cc(S(C)(=O)=O)ccc1-c1cc(-c2cnnc3c2ncn3C2CCC2)ccc1F]

Prepared according to the method described for Example 26 using 2-(6-fluoro-2'-methoxy-4'-(methylsulfonyl)-[1,1'-biphenyl]-3-yl)-4,4,5,5-tetramethyl-1,3,2-dioxaborolane (Preparation 18) and 6-chloro-9-cyclobutyl-9H-imidazo[4,5-c]pyridazine (Preparation 99) to afford the title compound as a colourless solid in 50% yield, 200 mg.

$^1$H NMR (400 MHz, CDCl$_3$): δ ppm 2.01-2.14 (m, 2H), 2.69-2.85 (m, 4H), 3.13 (s, 3H), 3.91 (s, 3H), 5.31 (m, 1H), 7.36 (t, 1H), 7.55-7.57 (m, 2H), 7.64 (dd, 1H), 8.22 (dd, 1H), 8.27-8.31 (m, 1H), 8.38 (s, 1H), 9.37 (s, 1H).

$^{19}$F NMR (376 MHz, CDCl$_3$): δ −111 ppm.

LCMS (System 13): Rt=2.61 minutes MS m/z 453 [M+H]$^+$

Example 30

4-[4'-(Ethylsulfonyl)-6-fluorobiphenyl-3-yl]-7-propyl-7H-imidazo[4,5-d]pyridazine

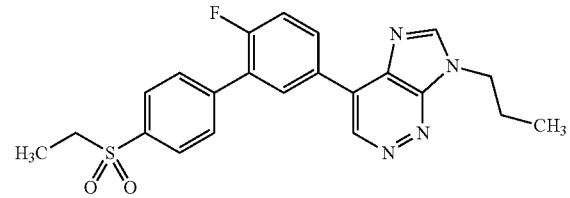 [SMILES: CCCn1cnc2c(-c3ccc(F)c(-c4ccc(S(=O)(=O)CC)cc4)c3)cnnc21]

Prepared according to the method described for Example 26 using 4-chloro-7-propyl-7H-imidazo[4,5-c]pyridazine (Preparation 101) and 2-(4'-ethylsulfonyl-6-fluorobiphenyl-3-yl)-4,4,5,5-tetramethyl-[1,3,2]dioxaborolane (Preparation 48) to afford the title compound as an off white solid in 10% yield, 10 mg.

$^1$H NMR (400 MHz, CDCl$_3$): δ ppm 1.02 (t, 3H), 1.33 (t, 3H), 2.06-2.12 (m, 2H), 3.16 (q, 2H), 4.48 (q, 2H), 7.40 (t, 1H), 7.84 (d, 2H), 8.01 (d, 2H), 8.21-8.23 (t, 1H), 8.25 (s, 1H), 8.42 (dd, 1H), 9.37 (s, 1H) ppm.

LCMS (System 7): Rt=3.27 minutes MS m/z 425 [M+H]$^+$

Example 31

4-[4'-(Ethylsulfonyl)-6-fluorobiphenyl-3-yl]-7-(propan-2-yl)-7H-imidazo[4,5-c]pyridazine

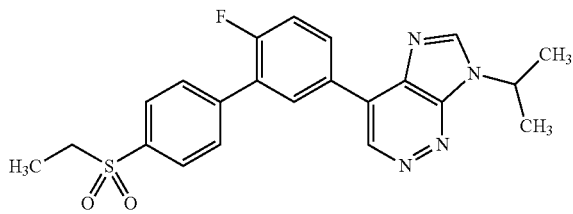 [SMILES: CCS(=O)(=O)c1ccc(-c2cc(-c3cnnc4c3ncn4C(C)C)ccc2F)cc1]

A stirred solution of 4'-ethylsulfonyl-6-fluorobiphenyl-3-yl-boronic acid (Preparation 65, 30 mg, 0.097 mmol), 4-chloro-7-isopropyl-7H-imidazo[4,5-c]pyridazine (Preparation 6, 15 mg, 0.077 mmol) and potassium phosphite (33 mg, 0.154 mmol) in dioxane (3 mL) and water (0.7 mL) was degassed with argon for 10 minutes followed by the addition of tricyclohexylphosphine (1.72 mg, 0.006 mmol) and tris(dibenzylideneacetone)palladium(0) (2.82 mg, 0.003 mmol). The resulting mixture was heated at 100° C. for 16 hours. The reaction mixture was filtered to remove inorganics and the filtrate was concentrated in vacuo to remove the volatiles. Purification of the crude residue by preparative TLC eluting with 2% MeOH in DCM afforded the title compound as off white solid in 27% yield, 9 mg.

$^1$H NMR (400 MHz, CDCl$_3$): δ ppm 1.33 (t, 3H), 1.76 (d, 6H), 3.18 (q, 2H), 5.20-5.24 (m, 1H), 7.40 (t, 1H), 7.82 (d, 2H), 8.00 (d, 2H), 8.20-8.23 (m, 1H), 8.32 (s, 1H), 8.41 (d, 1H), 9.36 (s, 1H).

LCMS (System 9): Rt=3.27 minutes MS m/z 425 [M+H]$^+$

Example 32

2'-Fluoro-5'-(7-isopropyl-7H-imidazo[4,5-c]pyridazin-4-yl)biphenyl-4-sulfonamide

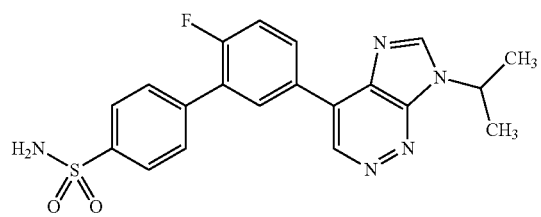 [SMILES: CC(C)n1cnc2c(-c3ccc(F)c(-c4ccc(S(N)(=O)=O)cc4)c3)cnnc21]

To 4-Chloro-7-isopropyl-7H-imidazo[4,5-c]pyridazine (Preparation 6, 50 mg, 0.254 mmoles) and 2'-fluoro-5'-(4,4,5,5-tetramethyl-1,3,2-dioxaborolan-2-yl)biphenyl-4-sulfonamide (Preparation 2, 131 mg, 0.254 mmoles) in dioxane (2.5 mL) was added Na$_2$CO$_3$ (80 mg, 0.759 mmol) pre dissolved in water (0.5 mL) and [1,1-bis(diphenylphosphino)ferrocene]dichloropalladium(II) (7.3 mg, 0.009 mmol). The reaction was degassed with nitrogen and heated under microwave irradiation at 90° C. for 15 minutes. After cooling, ethyl acetate and Na$_2$SO$_4$ were added and the mixture decanted and washed with ethyl acetate. Purification by silica gel column chromatography eluting with DCM: MeOH 1:0 to 9:1 yielded the title product in 50% yield, 57 mg.

$^1$H NMR (400 MHz, DMSO-d$_6$): δ ppm 1.68 (d, 6H), 5.13 (s, 1H), 7.46 (s, 2H), 7.62 (dd, 1H), 7.85-7.91 (m, 2H), 7.94-8.01 (m, 2H), 8.54 (s, 1H), 8.63 (dd, 1H), 8.95 (s, 1H), 9.62 (s, 1H).

LCMS Rt=0.68 minutes; MS m/z 412 [M+H]$^+$

Example 33

2'-Fluoro-N-methyl-5'-[7-(propan-2-yl)-7H-imidazo[4,5-c]pyridazin-4-yl]biphenyl-4-sulfonamide

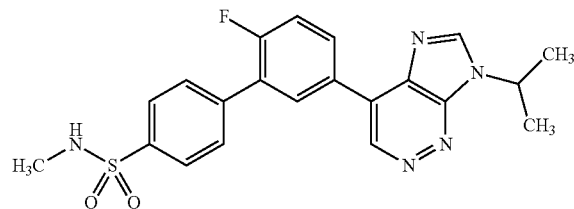 [SMILES: CNS(=O)(=O)c1ccc(-c2cc(-c3cnnc4c3ncn4C(C)C)ccc2F)cc1]

To a solution of 2'-fluoro-N-methyl-5'-(4,4,5,5-tetramethyl-1,3,2-dioxaborolan-2-yl)biphenyl-4-sulfonamide (Preparation 44, 112 mg, 0.29 mmol) and 4-chloro-7-isopropyl-7H-imidazo[4,5-c]pyridazine (Preparation 6, 54 mg, 0.27 mmol) in anhydrous dioxane (1.6 mL) was added aqueous Na$_2$CO$_3$ solution (2M, 0.41 mL, 0.81 mmol) and a stream of nitrogen gas was bubbled through the suspension for 5 minutes. Tetrakistriphenylphosphine palladium(0) (5.8 mg, 0.005 mmol) was added and the mixture was heated under microwave irradiation at 120° C. for 12 minutes. The reaction mixture was cooled and diluted with EtOAc (15 mL) and water (30 mL). The organic phase was extracted and the aqueous layer was back-extracted with EtOAc (2×15 mL). The organic layers were combined, washed with brine, dried over Na$_2$SO$_4$, filtered and the filtrate was evaporated in vacuo to leave a tan solid that was suspended in EtOAc (2.5 mL) and stirred at room temperature for 18 hours. The solid was filtered, rinsed with EtOAc (2×1 mL) and further dried to afford the title compound as an off-white solid in 82% yield, 120 mg.

$^1$H NMR (500 MHz, CDCl$_3$): δ ppm 1.79 (d, 6H), 2.75 (d, 3H), 4.52 (q, 1H), 5.24 (spt, 1H), 7.42 (dd, 1H), 7.81 (m, 2H), 7.99 (d, 2H), 8.26 (ddd, 1H), 8.38 (s, 1H), 8.43 (dd, 1H), 9.42 (s, 1H).

MS m/z 426 [M+H]$^+$

Example 34

4-[4'-(Ethylsulfonyl)-2',6-difluorobiphenyl-3-yl]-7-(propan-2-yl)-7H-imidazol[4,5-c]pyridazine

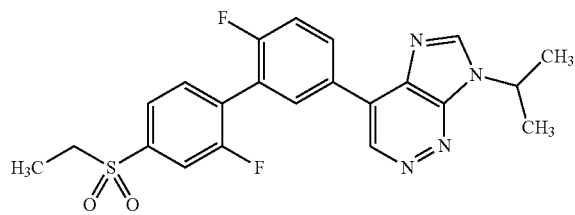 [SMILES: CCS(=O)(=O)c1ccc(-c2cc(-c3cnnc4c3ncn4C(C)C)ccc2F)c(F)c1]

To a solution of 2-[4'-(ethylsulfonyl)-2',6-difluorobiphenyl-3-yl]-4,4,5,5-tetramethyl-1,3,2-dioxaborolane (Preparation 47, 48 mg, 0.12 mmol) and 4-chloro-7-isopropyl-7H-imidazo[4,5-c]pyridazine (Preparation 6, 22 mg, 0.11 mmol) in anhydrous dioxane (0.56 mL) was added aqueous $Na_2CO_3$ solution (2M, 0.17 mL, 0.34 mmol) and a stream of nitrogen gas was bubbled through the suspension for 5 minutes. Tetrakistriphenylphosphine palladium(0) (2.3 mg, 0.002 mmol) was added and the mixture was heated under microwave irradiation at 120° C. for a total of 15 minutes. The reaction mixture was cooled, diluted with water (20 mL) and extracted with EtOAc (3×15 mL). The organic layers were combined, washed with brine, dried over $Na_2SO_4$, filtered and the filtrate was evaporated in vacuo to leave a tan sticky solid that was purified by silica gel column chromatography eluting with heptane:EtOAc to afford the title compound as a tan solid in 80% yield, 40 mg.

$^1$H NMR (500 MHz, $CDCl_3$): δ ppm 1.37 (t, 3H), 1.78 (d, 6H), 3.21 (q, 2H), 5.23 (spt, 1H), 7.44 (t, 1H), 7.71-7.75 (m, 1H), 7.78 (dd, 1H), 7.83 (dd, 1H), 8.30-8.39 (m, 3H), 9.40 (s, 1H).

LCMS (System 8): Rt=3.12 minutes; MS m/z 443 [M+H]$^+$

Example 35

2'-Fluoro-5'-(7-isopropyl-7H-imidazo[4,5-c]pyridazin-4-yl)-4-(isopropylsulfonyl)-[1,1'-biphenyl]-2-carbonitrile

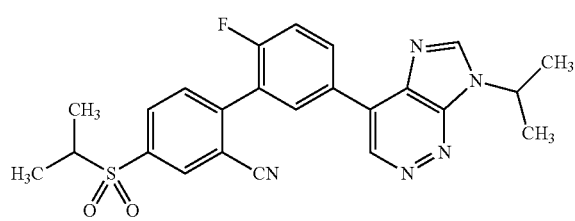 [SMILES: CC(C)n1cnc2c(-c3ccc(F)c(-c4ccc(S(=O)(=O)C(C)C)cc4C#N)c3)cnnc21]

A solution of 6-(3-bromo-4-fluorophenyl)-9-isopropyl-9H-imidazo[4,5-c]pyridazine (Preparation 87, 50.0 mg, 0.150 mmol), bis(pinacolato) diboron (57.0 mg, 0.225 mmol), potassium acetate (29.0 mg, 0.300 mmol) in dioxane (3.5 mL) at room temperature was purged with nitrogen for 30 minutes. [1,1-Bis(diphenylphosphino)ferrocene]dichloropalladium(II) (11.0 mg, 0.0150 mmol) was added to the reaction mixture, which was further purged with nitrogen for 10 minutes.

The reaction mixture was heated at reflux for 62 hours. The reaction was cooled to room temperature and 2-bromo-5-(isopropylsulfonyl)benzonitrile (Preparation 25, 48.0 mg, 0.165 mmol), sodium carbonate (56.0 mg, 0.530 mmol) in water (0.2 mL) was added, purged with nitrogen for 0.25 hours. [1,1'-Bis(diphenylphosphino)ferrocene]dichloropalladium(II) (11.0 mg, 0.0150 mmol) was added and the reaction mixture was purged with nitrogen for 10 minutes and heated to 110° C. The reaction was cooled to room temperature after 1.5 hours, filtered through celite and concentrated in vacuo. The residue was purified using silica gel column chromatography eluting with EtOAc/heptanes 1:1 to 0:1 to afford a yellow solution which crystallised upon concentration. The solid was washed with EtOAc (3×5 mL) before being diluted in acetonitrile and concentrated in vacuo. The title compound was afforded as an off-white solid 12% yield, 9.1 mg.

$^1$H NMR (400 MHz, $CDCl_3$): δ ppm 1.39 (d, 6H), 1.78 (d, 6H), 3.30 (br m, 1H), 5.22 (br m, 1H), 7.50 (br s, 1H), 7.84 (br s, 1H), 8.20 (br s, 1H), 8.30-8.49 (m, 4H), 9.44 (s, 1H).

$^{19}$F NMR (376 MHz, $CDCl_3$): δ −111.53 ppm.

LCMS (System 13): Rt=2.61 minutes; MS m/z 464 [M+H]$^+$

Examples 36 to 41 were prepared according to the method described above for Example 35, starting from 6-(3-bromo-4-fluorophenyl)-9-cyclopropyl-9H-imidazo[4,5-c]pyridazine (Preparation 87) unless otherwise described and the appropriate bromide or boronic acid as described.

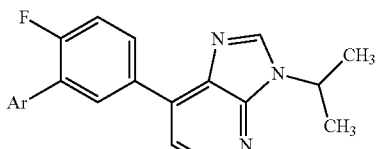

| Example | |
|---|---|
| 36 | 4-(2',6-Difluoro-4'-(isopropylsulfonyl)-[1,1'-biphenyl]-3-yl)-7-isopropyl-7H-imidazo[4,5-c]pyridazine |

-continued

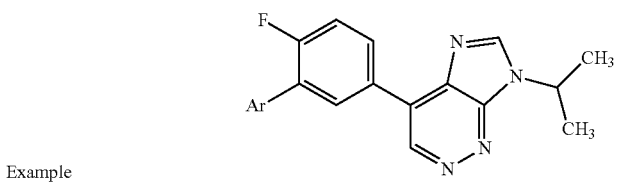

| Example | | |
|---|---|---|
| | 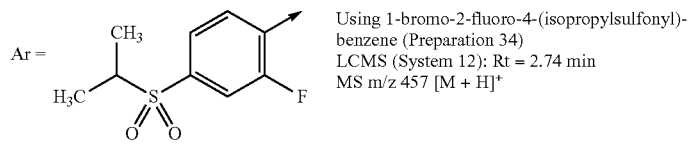 | Using 1-bromo-2-fluoro-4-(isopropylsulfonyl)-benzene (Preparation 34)<br>LCMS (System 12): Rt = 2.74 min<br>MS m/z 457 [M + H]$^+$ |
| 37 | 4-(6-Fluoro-4'-(isopropylsulfonyl)-2'-methoxy-[1,1'-biphenyl]-3-yl)-4-isopropyl-4H-imidazo[4,5-c]pyridazine | |
| | 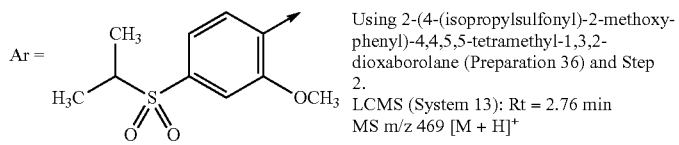 | Using 2-(4-(isopropylsulfonyl)-2-methoxy-phenyl)-4,4,5,5-tetramethyl-1,3,2-dioxaborolane (Preparation 36) and Step 2.<br>LCMS (System 13): Rt = 2.76 min<br>MS m/z 469 [M + H]$^+$ |
| 38 | 4-(6-Fluoro-2'-methoxy-4'-(methylsulfonyl)-[1,1'-biphenyl]-3-yl)-7-isopropyl-7H-imidazo[4,5-c]pyridazine | |
| | 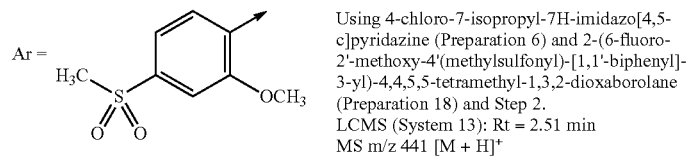 | Using 4-chloro-7-isopropyl-7H-imidazo[4,5-c]pyridazine (Preparation 6) and 2-(6-fluoro-2'-methoxy-4'(methylsulfonyl)-[1,1'-biphenyl]-3-yl)-4,4,5,5-tetramethyl-1,3,2-dioxaborolane (Preparation 18) and Step 2.<br>LCMS (System 13): Rt = 2.51 min<br>MS m/z 441 [M + H]$^+$ |
| 39 | 4-(2'-Chloro-4'-(ethylsulfonyl)-6-fluoro-[1,1'-biphenyl]-3-yl)-7-isopropyl-7H-imidazo[4,5-c]pyridazine | |
| | 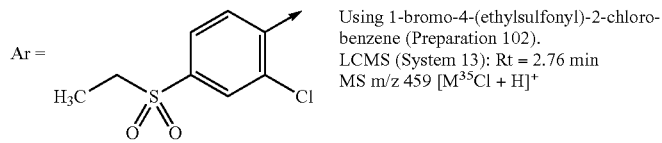 | Using 1-bromo-4-(ethylsulfonyl)-2-chloro-benzene (Preparation 102).<br>LCMS (System 13): Rt = 2.76 min<br>MS m/z 459 [M$^{35}$Cl + H]$^+$ |
| 40 | 4-(4'-(Ethylsulfonyl)-6-fluoro-2'-methoxy-[1,1'-biphenyl]-3-yl)-7-isopropyl-7H-imidazo[4,5-c]pyridazine | |
| | 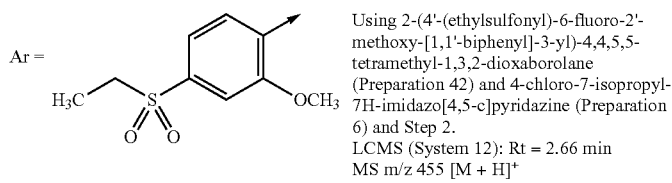 | Using 2-(4'-(ethylsulfonyl)-6-fluoro-2'-methoxy-[1,1'-biphenyl]-3-yl)-4,4,5,5-tetramethyl-1,3,2-dioxaborolane (Preparation 42) and 4-chloro-7-isopropyl-7H-imidazo[4,5-c]pyridazine (Preparation 6) and Step 2.<br>LCMS (System 12): Rt = 2.66 min<br>MS m/z 455 [M + H]$^+$ |
| 41 | 4-(Ethylsulfonyl)-2'-fluoro-5'-(7-isopropyl-7H-imidazo[4,5-c]pyridazin-4-yl)-[1,1'-biphenyl]-2-carbonitrile | |
| | 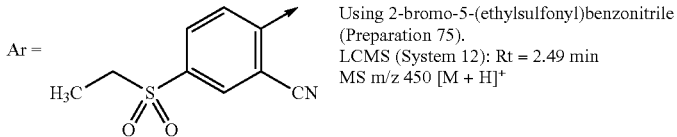 | Using 2-bromo-5-(ethylsulfonyl)benzonitrile (Preparation 75).<br>LCMS (System 12): Rt = 2.49 min<br>MS m/z 450 [M + H]$^+$ |

Example 42

7-Cyclopentyl-4-(6-fluoro-2'-methoxy-4'-(methylsulfonyl)-[1,1'-biphenyl]-3-yl)-7H-imidazo[4,5-c]pyridazine

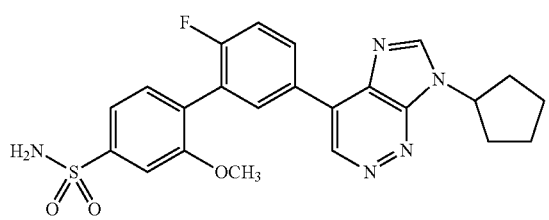 [SMILES: COc1cc(S(N)(=O)=O)ccc1-c1cc(-c2cnnc3c2ncn3C2CCCC2)ccc1F]

To a solution of 2-(6-fluoro-2'-methoxy-4'-(methylsulfonyl)-[1,1'-biphenyl]-3-yl)-4,4,5,5-tetramethyl-1,3,2-dioxaborolane (Preparation 18, 376 mg, 0.99 mmol) and 6-chloro-9-cyclopentyl-9H-imidazo[4,5-c]pyridazine (Preparation 13, 200 mg, 0.90 mmol) in dioxane (20 mL) was added $Na_2CO_3$ (286 mg, 2.70 mmol) in water (5 mL).

The resulting solution was degassed with nitrogen then tetrakis(triphenylphosphine)palladium(0) (104 mg, 0.09 mmol) was added and the reaction mixture was degassed again and heated at 110° C. for 18 hours. The reaction was cooled to room temperature, diluted with EtOAc (100 mL) and washed with water (150 mL). The aqueous layer was re-extracted with EtOAc (2×100 mL) and the combined organic layers were dried ($Na_2SO_4$), filtered and concentrated under reduced pressure to give the crude product. This material was purified by silica gel column chromatography eluting with 30-60% EtOAc:Heptane followed by elution through an SCX cartridge using $CH_2Cl_2$, EtOAc, THF, MeOH and 7N ammonia in MeOH to provide the title compound as a yellow solid in 26% yield, 108 mg.

$^1$H NMR (400 MHz, $CDCl_3$): δ ppm 1.81-1.93 (m, 2H), 1.96-2.05 (m, 2H), 2.12-2.21 (m, 2H), 2.38-2.46 (m, 2H), 3.13 (s, 3H), 3.91 (s, 3H), 5.25 (m, 1H), 7.36 (t, 1H), 7.55-7.57 (m, 2H), 7.64 (dd, 1H), 8.22 (dd, 1H), 8.27-8.31 (m, 1H), 8.33 (s, 1H), 9.37 (s, 1H).

$^{19}$F NMR (376 MHz, $CDCl_3$): δ −111 ppm.

LCMS (System 13): Rt=2.73 minutes MS m/z 467 [M+H]$^+$

Example 43

7-Cyclopentyl-4-(4'-(ethylsulfonyl)-6-fluoro-2'-methoxy-[1,1'-biphenyl]-3-yl)-7H-imidazo[4,5-c]pyridazine

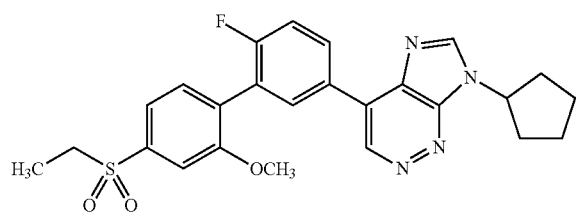 [SMILES: CCS(=O)(=O)c1ccc(-c2cc(-c3cnnc4c3ncn4C3CCCC3)ccc2F)c(OC)c1]

A suspension of 6-chloro-9-cyclopentyl-9H-imidazo[4,5-c]pyridazine (Preparation 13, 52 mg, 0.23 mmol), 2-(4'-(ethylsulfonyl)-6-fluoro-2'-methoxy-[1,1'-biphenyl]-3-yl)-4,4,5,5-tetramethyl-1,3,2-dioxaborolane (Preparation 42, 100 mg, 0.24 mmol), sodium carbonate (2.0 M aqueous solution, 0.36 mL) in dioxane (6 mL) were degassed with nitrogen for 30 minutes. Tetrakis(triphenylphosphine)palladium(0) (28 mg, 0.024 mmol) was added and the reaction warmed to 110° C. and stirred for 18 hours. The reaction was cooled to room temperature, filtered through celite and the celite pad was washed with $CH_2Cl_2$ (10 mL). Water (10 mL) was added and the product extracted with $CH_2Cl_2$ (2×10 mL). The organic layer was dried over $Na_2SO_4$, filtered and concentrated under vacuum. The residue was purified using silica gel column chromatography eluting with EtOAc:heptanes 8:2 followed by elution through an SCX cartridge using MeOH, EtOAc, THF, DCM, and 7N $NH_3$ in MeOH to afford the title compound as a pale yellow oil in 14% yield, 15.2 mg.

$^1$H NMR (400 MHz, $CDCl_3$): δ ppm 1.38 (t, 3H), 1.88 (m, 2H), 2.01 (m, 2H), 1.20 (m, 2H), 2.41 (m, 2H), 3.19 (q, 2H), 3.89 (s, 3H), 5.22 (m, 1H), 7.29 (dd, 1H), 7.54 (s, 1H), 7.63 (m, 2H), 8.21 (dd, 1H), 8.38 (m, 2H), 9.38 (s, 1H).

$^{19}$F NMR (376 MHz, $CDCl_3$): −111.3 ppm.

LCMS (System 12): Rt=2.81 minutes MS m/z 481 [M+H]$^+$

Example 44

7-Ethyl-4-(4'-(ethylsulfonyl)-2'-fluoro-6-methoxy-[1,1'-biphenyl]-3-yl)-7H-imidazo[4,5-c]pyridazine

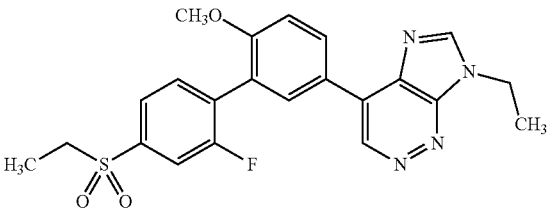

To 2-(4'-(ethylsulfonyl)-2'-fluoro-6-methoxy-[1,1'-biphenyl]-3-yl)-4,4,5,5-tetramethyl-1,3,2-dioxaborolane (Preparation 69, 90 mg, 0.21 mmol) in dioxane (2.5 mL) and water (1 mL) was added 4-chloro-7-ethyl-7H-imidazo[4,5-c]pyridazine (Preparation 8, 40 mg, 0.21 mmol) and sodium carbonate (68 mg, 0.64 mmol). The reaction was degassed and tetrakis(triphenylphosphine) palladium(0) (25 mg, 0.02 mmol) was added. The reaction was further degassed and then heated to 110° C. for 2 hours and then cooled to room temperature. The reaction mixture was diluted with EtOAc (40 mL) was passed through celite and the solvent removed in vacuo. The crude material was purified by reverse phase column chromatography eluting with a gradient of 0.1% formic acid in MeCN/water. The resulting residue was dissolved in DMSO (1 mL) and purified using preparative HPLC to give the title compound as a colourless solid in 26% yield, 24 mg.

$^1$H-NMR (400 MHz, $CDCl_3$): δ ppm 1.37 (t, 3H), 1.68 (t, 3H), 3.19 (q, 2H), 3.91 (s, 3H), 4.57 (q, 2H), 7.22 (d, 1H), 7.64-7.72 (m, 2H), 7.76-7.78 (m, 1H), 8.23 (d, 1H), 8.25 (s, 1H), 8.33-8.36 (m, 1H) 9.37 (s, 1H).

LCMS (System 13): Rt=2.22 minutes MS m/z 441 [M+H]$^+$

Example 45

4-(6-Chloro-4'-(ethylsulfonyl)-2'-methoxy-[1,1'-biphenyl]-3-yl)-7-ethyl-7H-imidazo[4,5-c]pyridazine

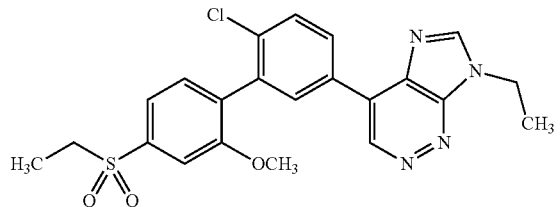 [SMILES: CCn1cnc2c(-c3ccc(Cl)c(-c4ccc(S(=O)(=O)CC)cc4OC)c3)cnnc21]

Prepared according to the method described for Example 45 using 2-(6-chloro-4'-(ethylsulfonyl)-2'-methoxy-[1,1'-biphenyl]-3-yl)-4,4,5,5-tetramethyl-1,3,2-dioxaborolane (Preparation 56) and 4-chloro-7-ethyl-7H-imidazo[4,5-c]pyridazine (Preparation 8) to afford the title compound as an off white solid in 19% yield, 9.9 mg.

$^1$H NMR (400 MHz, CDCl$_3$): δ ppm 1.37 (t, 3H), 1.68 (t, 3H), 3.21 (q, 2H), 3.88 (s, 3H), 4.57 (q, 2H), 7.50 (m, 2H), 7.60 (dd, 1H), 7.68 (d, 1H), 8.14 (d, 1H), 8.24 (dd, 1H), 8.27 (s, 1H), 9.36 (s, 1H).

LCMS (system 11): Rt=2.44 minutes MS m/z 456 [M$^{35}$Cl+H]$^+$

Example 46

7-Ethyl-4-(4'-(ethylsulfonyl)-2',6-dimethoxy-[1,1'-biphenyl]-3-yl)-7H-imidazol[4,5-c]pyridazine

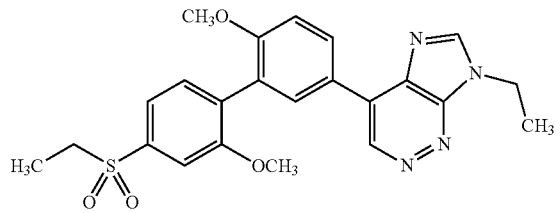

Prepared according to the method described for Example 45 using 2-(4'-(Ethylsulfonyl)-2',6-dimethoxy-[1,1'-biphenyl]-3-yl)-4,4,5,5-tetramethyl-1,3,2-dioxaborolane (Preparation 59) and 4-chloro-7-ethyl-7H-imidazo[4,5-c]pyridazine (Preparation 8) to afford the title compound as an off white solid in 13% yield, 14.7 mg.

$^1$H NMR (400 MHz, CDCl$_3$): δ ppm 1.38 (t, 3H), 1.68 (t, 3H), 3.19 (q, 2H), 3.87 (s, 6H), 4.56 (q, 2H), 7.19 (d, 1H), 7.53 (m, 3H), 8.12 (d, 1H), 8.25 (s, 1H), 8.35 (dd, 1H), 9.36 (s, 1H).

LCMS (System 11): Rt=2.33 minutes MS m/z 453 [M+H]$^+$

Example 47

5-(7-Ethyl-7H-imidazo[4,5-c]pyridazin-4-yl)-4'-(ethylsulfonyl)-2'-methoxy-[1,1'-biphenyl]-2-carbonitrile

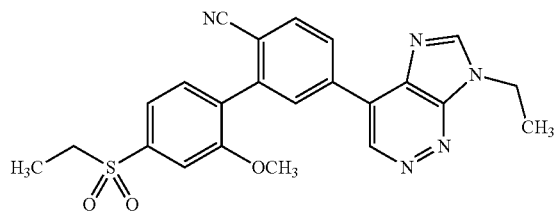 [SMILES: CCn1cnc2c(-c3ccc(C#N)c(-c4ccc(S(=O)(=O)CC)cc4OC)c3)cnnc21]

Prepared according to the method described for Example 45 using (6-cyano-4'-(ethylsulfonyl)-2'-methoxy-[1,1-biphenyl]-3-yl)boronic acid (Preparation 67) and 4-chloro-7-ethyl-7H-imidazo[4,5-c]pyridazine (Preparation 8) to afford the title compound as a white solid in 10% yield, 10.1 mg.

$^1$H NMR (400 MHz, CDCl$_3$): δ ppm 1.38 (t, 3H), 1.71 (t, 3H), 3.21 (q, 2H), 3.95 (s, 3H), 4.61 (q, 2H), 7.56-7.58 (m, 2H), 7.60-7.66 (m, 1H), 7.96 (d, 1H), 8.32 (s, 2H), 8.35-8.38 (m, 1H), 9.40 (s, 1H).

LCMS (System 11): Rt=2.30 minutes MS m/z 448 [M+H]$^+$

Example 48

5-(7-Ethyl-7H-imidazo[4,5-c]pyridazin-4-yl)-4'-(ethylsulfonyl)-2'-methoxy-[1,1'-biphenyl]-2-ol

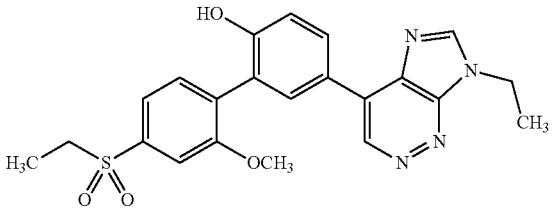

To a stirred solution 4-chloro-7-ethyl-7H-imidazo[4,5-c]pyridazine (Preparation 8, 80 mg, 0.44 mmol) and 4'-(ethylsulfonyl)-2'-methoxy-5-(4,4,5,5-tetramethyl-1,3,2-dioxaborolan-2-yl)-[1,1'-biphenyl]-2-ol (Preparation 89, 167 mg, 0.44 mmol) in dioxane (15 mL) and water (5 mL) was added sodium carbonate (106 mg, 1.0 mmol) and the reaction mixture was degassed before adding tetrakis(triphenylphosphine) palladium(0) (46 mg, 0.04 mmol). The reaction was heated to 100° C. for 18 hours. After this time the reaction was allowed to cool to room temperature, filtered through celite and the filtrate evaporated under reduced pressure. The crude was purified by silica gel column chromatography eluting with CH$_2$Cl$_2$:MeOH from 95:5 to 9:1 and then further purified by preparative HPLC to afford the title compound as colourless solid 11%, 19 mg.

$^1$H NMR (400 MHz CDCl$_3$): δ ppm 1.38 (t, 3H), 1.69 (t, 3H), 3.21 (q, 2H), 4.03 (s, 3H), 4.57 (q, 2H), 7.23 (s, 1H), 7.59 (s, 1H), 7.64-7.69 (m, 2H), 8.22-8.25 (m., 3H), 9.37 (s, 1H).

LCMS: (System 13) Rt=2.02 minutes MS m/z 439 [M+H]$^+$

Example 49

7-Ethyl-4-[4'-(ethylsulfonyl)-6-fluorobiphenyl-3-yl]-7H-imidazo[4,5-d]pyridazine

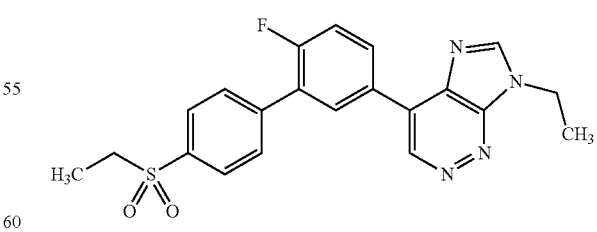

Prepared according to the method described for Example 44 using 4-chloro-7-ethyl-7H-imidazo[4,5-c]pyridazine (Preparation 8) and 2-(4'ethylsulfonyl-6-fluorobiphenyl-3-yl)-4,4,5,5-tetramethyl[1,3,2]dioxaborolane (Preparation 48). The crude residue was triturated with EtOAc followed by recrystallisation from MeCN to afford the title compound.

¹H NMR (400 MHz CDCl₃): δ ppm 1.34 (t, 3H), 1.70 (t, 3H), 3.17 (q, 2H), 4.61 (q, 2H), 7.42 (dd, 1H), 7.85 (d, 2H), 8.03 (d, 2H), 8.24 (ddd, 1H), 8.42 (dd, 1H), 9.39 (s, 1H).
LCMS Rt=1.15 minutes MS m/z 411 [M+H]⁺

Example 50

7-Ethyl-4-[4-fluoro-3-(2-methyl-1,1-dioxido-2,3-di hydro-1,2-benzisothiazol-5-yl)phenyl]-7H-imidazo [4,5-d]pyridazine

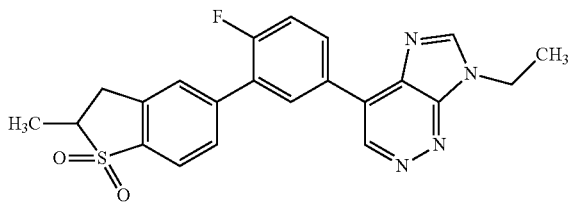 [SMILES: CCn1cnc2c(-c3ccc(F)c(-c4ccc5c(c4)CC(C)S5(=O)=O)c3)cnnc21]

A solution of 7-ethyl-4-[4-fluoro-3-(4,4,5,5-tetramethyl-[1,3,2]dioxaborolan-2-yl)phenyl]-7H-imidazo[4,5-c]pyridazine (Preparation 95, 70 mg, 0.190 mmol), 5-bromo-2-methyl-2,3-dihydro-1,2-benzisothiazole 1,1-dioxide (Preparation 39, 50 mg, 0.190 mmol) cesium carbonate (124 mg, 0.380 mmol) in DMF (2 mL) was degassed with nitrogen for 30 minutes. Bis(diphenylphosphino)ferrocene]dichloropalladium(II) (12 mg, 0.019 mmol) was added and the reaction heated to 95° C. for 18 hours. The reaction was cooled and purified using silica gel column chromatography eluting with 0-100% EtOAc in DCM to afford the title compound (26 mg, 32%).
¹H NMR (400 MHz CDCl₃): δ ppm 1.68 (t, 3H), 3.00 (s, 3H), 4.42 (s, 2H), 4.59 (q, 2H), 7.41 (t, 1H), 7.63 (s, 1H), 7.78 (d, 1H), 7.93 (d, 1H), 8.20-8.25 (m, 1H), 8.27 (s, 1H), 8.39 (d, 1H), 9.38 (s, 1H).
LCMS Rt=2.19 minutes MS m/z 424 [M+H]⁺

Preparations Section

Preparation 1

5'-Bromo-2'-fluorobiphenyl-4-sulfonamide

To 4-bromo-1-fluoro-2-iodobenzene (361 mg, 1.2 mmol) and 4-sulfamoyl-phenylboronic acid (240 mg, 1.20 mmol) in 4:1 dioxane/H₂O (5 mL) was added Na₂CO₃ (382 mg, 3.60 mmol) and [1,1'-Bis(diphenylphosphino)-ferrocene]dichloropalladium(II) (34.3 mg, 0.042 mmol). The reaction was heated under microwave irradiation at 120° C. for 15 minutes, cooled and diluted with EtOAc and water. The aqueous layer was extracted with EtOAc and the combined organic layers dried over Na₂SO₄. The solvent was removed in vacuo and the resulting residue purified via silica gel column chromatography eluting with EtOAc:heptanes 0:1 to 1:1 to afford the desired product 55%, 218 mg, 55%.
LCMS Rt=0.79 minutes MS m/z 331 [M+H]⁺

Preparation 2

2'-Fluoro-5'-(4,4,5,5-tetramethyl-1,3,2-dioxaborolan-2-yl)biphenyl-4-sulfonamide 5'-bromo-2'-fluorobiphenyl-4-sulfonamide (Preparation 1, 118 mg, 0.303 mmol) and bis(pinacolato)diboron (199 mg, 0.785 mmole), KOAc (123 mg, 1.25 mmoles) and Pd(dppf)Cl₂ (14.7 mg, 0.018 mmole) were suspended in dioxane (5 mL) and DMSO (0.2 mL). The reaction was heated under microwave irradiation at 90° C. for 20 minutes and the solvents removed under reduced pressure. Purification via silica gel column chromatography eluting with EtOAc:heptanes 0:1 to 1:1 afforded the title compound in 81% yield, 110 mg.
¹H-NMR (400 MHz, CDCl₃): δ ppm 1.25 (s, 12H), 6.20-6.29 (m, 2H), 7.04-7.11 (m, 1H), 7.56-7.61 (m, 2H), 7.69-7.74 (m, 1H), 7.77-7.81 (m, 1H), 7.89 (d, 2H).
LCMS Rt=0.89 minutes MS m/z 378 [M+H]⁺

Preparation 3

3,4,5-Trichloropyridazine 4,5-dichloropyridazin-3(2H)-one (10.0 g, 60.6 mmole) in POCl₃ (60 mL, 642 mmole) was stirred at 110° C. for 18 hours. Toluene was added and the solvents removed under reduced pressure. EtOAc (200 mL) and water were added to the resulting residue and the organic layer washed with water and brine and then dried over MgSO₄. Concentration under reduced pressure provided the desired product as an off white solid in 90% yield, 10 g.
¹H NMR (400 MHz, CDCl₃): δ ppm 9.10 (d, 1H).
HPLC (Method 2): Rt=3.35 minutes Preparation 4

3,5-Dichloropyridazin-4-amine

A mixture of 3,4,5-trichloropyridazine (Preparation 3, 500 mg, 2.73 mmole) in EtOH (5.5 mL) and NH₄OH (5.5 mL) was heated under microwave irradiation 120° C. for 25 minutes. Concentration under reduced pressure and purification via silica gel column chromatography eluting with acetone:dichloromethane (0-15% acetone), provided the title product in 36% yield, 163 mg.
¹H NMR (400 MHz, CDCl₃): δ ppm 5.11 (br s, 2H), 8.74 (s, 1H).
LCMS Rt=0.27 minutes MS m/z 164 [M+H]⁺

Preparation 5

5-Chloro-N³-isopropylpyridazine-3,4-diamine

HOAc (2.47 mL, 42.7 mmol) was added dropwise to a mixture of 3,5-dichloropyridazin-4-amine (Preparation 4, 1000 mg, 6.098 mmol) and isopropylamine (7.27 mL, 85.4 mmol) cooled to 0° C. The resulting solid/suspension was heated under microwave irradiation at 105° C. for 5 hours. The reaction mixture was dissolved in minimum amount of MeOH and purified by silica gel column chromatography eluting with EtOAc:heptane: 10%-90% to provide the title compound as a slightly brownish solid in 74% yield, 2.52 g.
¹H NMR (400 MHz, CDCl₃): δ ppm 1.22-1.25 (m, 6H), 4.37 (d, 1H), 4.91 (d, 1H), 5.06 (s, 2H), 8.29 (s, 1H).
LCMS Rt=0.4 minutes MS m/z 187 [M³⁵Cl+H]⁺

Preparation 6

4-Chloro-7-isopropyl-7H-imidazo[4,5-c]pyridazine

A mixture of 5-chloro-N³-isopropylpyridazine-3,4-diamine (Preparation 5, 1020 mg, 5.47 mmol) in triethyl orthoformate (9 mL) was heated at 130° C. for 80 minutes. The solvent was removed in vacuo and the residue dissolved in MeOH/DCM and purified by silica gel column chromatography eluting with EtOAc:heptane 0-63% to provide the titled product as a white solid in 76% yield, 816 mg.

$^1$H NMR (400 MHz, CDCl$_3$): δ ppm 1.76 (d, 6H), 5.10-5.23 (m, 1H), 8.34 (s, 1H), 9.14 (s, 1H).

LCMS Rt=1.1 minute MS m/z 197 [M$^{35}$Cl+H]$^+$

Preparation 7

5-Chloro-N$^3$-ethylpyridazine-3,4-diamine

A mixture of 3,5-(dichloropyridazin-4-yl)amine (Preparation 4, 15 g, 92 mmol) and anhydrous ethylamine (50 mL) was heated to 120° C. for 48 hours in a sealed tube. The reaction mixture was cooled to room temperature, and then added to a mixture of water (500 mL) and EtOAc (50 mL). The resulting precipitate was separated by filtration and the filter cake was washed with tBME, and dried under vacuum to afford the title compound as off-white solid in 51% yield, 8.1 g.

$^1$H-NMR (400 MHz, DMSO-d$_6$): δ ppm 1.18 (t, 3H), 3.41 (q, 2H), 6.08-6.11 (m, 3H), 8.09 (s, 1H).

Preparation 8

4-Chloro-7-ethyl-7H-imidazo[4,5-c]pyridazine

A mixture of 5-chloro-N$^3$-ethyl-pyridazine-3,4-diamine (Preparation 7, 10.0 g, 58 mmol) and triethylorthoformate (60 mL) were heated to reflux for 4 hours. The reaction mixture was concentrated in vacuo and the residue was dissolved in EtOAc (50 mL) and filtered. The filter cake was washed with EtOAc and then the organic layers were washed with saturated brine solution, dried over Na$_2$SO$_4$ and concentrated in vacuo to afford the title compound as a yellow solid in 45% yield, 4.8 g.

Preparation 9

7-Ethyl-4-(4-fluorophenyl)-7H-imidazo[4,5-c]pyridazine

To a room temperature solution of 4-chloro-7-ethyl-7H-imidazo[4,5-c]pyridazine (Preparation 8, 9.6 g, 52.4 mmol) in dioxane (300 mL) was added 4-fluorobenzene boronic acid (8.8 g, 63 mmol) and an aqueous solution of Na$_2$CO$_3$ (1M, 260 mL, 262 mmol). The reaction mixture was degassed and purged with nitrogen gas 3 times. Tetrakis(triphenylphosphine)palladium(0) (1.2 g, 1.0 mmol) was then added and the mixture was heated to reflux for 4 hours. The organic solvent was removed in vacuo and the resulting aqueous mixture filtered. The filter cake was dried under vacuum to afford the title compound as a yellow solid in 55% yield, 7 g.

$^1$H NMR (400 MHz, CDCl$_3$): δ ppm 1.62 (t, 3H), 4.50 (q, 2H), 7.19 (t, 2H), 8.14-8.18 (m, 2H), 8.21 (s, 1H), 9.27 (s, 1H).

Preparation 10

7-Ethyl-4-(4-fluoro-3-iodophenyl)-7H-imidazo[4,5-c]pyridazine

Concentrated sulphuric acid (10 mL) was carefully added to 7-ethyl-4-(4-fluorophenyl)-7H-imidazo[4,5-c]pyridazine (Preparation 9, 825 mg, 2.4 mmol) surrounded by an ice bath, and the resultant reaction mixture was gently stirred at room temperature until a homogeneous solution was observed. To this was added 1,3-diiodo-5,5-dimethylhydantoin (1.36 g, 3.58 mmol) portion-wise, and stirring was continued for 5 minutes. The viscous mixture was then slowly poured into an aqueous sodium hydroxide solution (1M, 10 mL) at 0° C. with stirring. The black suspension slowly dissolved to give a blue solution. CH$_2$Cl$_2$ (20 mL) was added and the layers were separated. The organic layer was washed with saturated aqueous sodium bisulfite solution (20 mL) then concentrated in vacuo. The residue was purified using silica gel column chromatography eluting with heptane:EtOAc 1:1 to 0:100 to afford the title compound as a white solid in 95% yield, 1.19 g.

$^1$H-NMR (400 MHz, CDCl$_3$): δ ppm 1.70 (t, 3H), 4.58 (q, 2H), 8.19-8.23 (m, 1H), 8.29 (s, 1H), 8.65 (dd, 1H), 9.32 (s, 1H).

LCMS Rt=1.44 minutes MS m/z 369 [M+H]$^+$

Preparation 11

4-(3-Bromo-4-fluoro-phenyl)-7-ethyl-7H-imidazo[4,5-c]pyridazine

Concentrated sulphuric acid (66 g, 0.67 mol) was carefully added to 7-ethyl-4-(4-fluorophenyl)-7H-imidazo[4,5-c]pyridazine (Preparation 9, 2.3 g, 9.5 mmol) surrounded by an ice bath, and the resultant reaction mixture was gently stirred at room temperature until a homogeneous solution was observed. To this solution was added 1,3-dibromo-5,5-dimethylhydantoin (2.7 g, 9.5 mmol) portion-wise, and stirring was continued at 0° C. for 2 hours. The reaction mixture was poured carefully into aqueous sodium bisulphite (200 mL), and then basified with an aqueous sodium hydroxide solution (2 M) to pH=8 keeping the temperature below 20° C. EtOAc (50 mL) was added and the layers were separated. The aqueous layer was extracted with EtOAc (2×50 mL). The combined organic phases were washed with saturated brine solution, dried over Na$_2$SO$_4$ and concentrated in vacuo. The residue was purified by silica gel column chromatography eluting with petroleum ether:CH$_2$Cl$_2$ 1:1 followed by trituration with EtOAc to afford the title compound as a white solid in 41% yield, 1.25 g.

$^1$H NMR (400 MHz, CDCl$_3$): δ ppm 1.70 (t, 3H), 4.58 (q, 2H), 7.26-7.34 (m, 1H), 8.16-8.25 (m, 1H), 8.31 (s, 1H), 8.44-8.50 (m, 1H), 9.32 (s, 1H).

HPLC (System 15): Rt=2.98 minutes LRMS MS m/z 323 [M$^{81}$Br+H]$^+$

Preparation 12

5-Chloro-N$^3$-cyclopentylpyridazine-3,4-diamine 3,5-Dichloropyridazin-4-amine (Preparation 4, 1 g, 6.09 mmol) was added to cyclopentylamine (3.0 mL, 30.41 mmol) and water (1 mL) in a stainless steel sealed container. The mixture was heated for 16 hours at 150° C. The reaction mixture was cooled to room temperature then evaporated in vacuo. The residue was purified by silica gel column chromatography eluting with EtOAc to afford the title compound as yellow solid in 90% yield, 1.17 g.

$^1$H NMR (400 MHz, CDCl$_3$): δ ppm 1.43 (m, 2H), 1.76 (m, 4H), 2.21 (m, 2H), 4.17 (m, 1H), 4.39 (br s, 2H), 4.48 (m, 1H), 8.39 (s, 1H).

LCMS (System 12): Rt=1.15 minutes MS m/z 213 [M+H]$^+$

Preparation 13

4-Chloro-7-cyclopentyl-7H-imidazo[4,5-c]pyridazine

A mixture of 5-chloro-N-3-cyclopentylpyridazine-3,4-diamine (Preparation 12, 1.2 g, 5.64 mmol) and triethylorthoformate (10 mL) were heated to reflux for 1.5 hours. The reaction mixture was allowed to cool to room temperature, concentrated in vacuo and triturated with EtOAc (20 mL). The solid was filtered and the filtrate was reduced to dryness. The crude material was purified by silica gel column chromatography eluting with EtOAc to afford the title compound as a yellow solid in 51% yield, 902 mg.

$^1$H NMR (400 MHz, CD$_3$OD): δ ppm 1.85 (m, 2H), 2.07 (m, 2H), 2.26 (m, 2H), 2.44 (m, 2H), 5.22 (dt, 1H), 8.82 (s, 1H), 9.19 (s, 1H).

LCMS (System 13): Rt=1.97 minutes MS m/z 223 [M+H]$^+$

Preparation 14

1-Bromo-2-fluoro-4-(methylsulfonyl)benzene

A solution of 4-bromo-3-fluorobenzene sulphonyl chloride (10 g, 36.56 mmol) in THF (100 mL) was cooled to 0° C. and hydrazine monohydrate (6.2 mL, 127.96 mmol) was added dropwise. After the addition, the reaction was left to stir at room temperature for 1 hour before adding heptane (500 mL). The precipitate formed was filtered off and re-dissolved in industrial methylated spirit (200 mL). Sodium acetate (18 g, 219.36 mmol) was added followed by iodomethane (11.38 mL, 182.8 mmol). The reaction mixture was stirred at reflux for 18 hours. The reaction was cooled to room temperature and the solvent was concentrated to half of the initial volume. Water (300 mL) was added and the product was extracted with EtOAc (3×300 mL). The combined organic layers were washed with brine (300 mL) and dried (Na$_2$SO$_4$), filtered and concentrated under reduced pressure. The crude residue was purified by silica gel column chromatography eluting from 15% to 35% EtOAc/heptane to afford the title compound as a colourless solid in 48% yield, 4.40 g.

$^1$H NMR (400 MHz, CDCl$_3$): δ ppm 3.04 (s, 3H), 7.62 (dd, 1H), 7.70 (dd, 1H), 7.80 (dd, 1H).

$^{19}$F NMR (376 MHz, CDCl$_3$): δ −102 ppm.

LCMS (System 13): Rt=2.50 minutes MS m/z no ionisation.

Preparation 15

1-Bromo-2-methoxy-4-(methylsulfonyl)benzene

To a solution of 1-bromo-2-fluoro-4-(methylsulfonyl)benzene (Preparation 14, 1.5 g, 5.93 mmol) in MeOH (12 mL) was added sodium methoxide (480 mg, 8.89 mmol) and the reaction mixture was irradiated at 100° C. in the microwave for 1.5 hours. After this time the reaction was quenched with water (50 mL) and the product was extract with EtOAc (3×50 mL). The combined organic layers were dried (Na$_2$SO$_4$), filtered and concentrated under reduced pressure. The residue was purified by silica gel column chromatography eluting with 20-40% EtOAc in heptane to afford the title compound as colourless solid in 53% yield.

$^1$H NMR (400 MHz, CDCl$_3$): δ ppm 3.06 (s, 3H), 3.98 (s, 3H), 7.39-7.41 (m, 2H), 7.75 (d, 1H).

LCMS (System 13): Rt=2.49 minutes MS m/z no ionisation.

Preparation 16

2-(2-Methoxy-4-(methylsulfonyl)phenyl)-4,4,5,5-tetramethyl-1,3,2-dioxaborolane

To a solution of 1-bromo-2-methoxy-4-(methylsulfonyl)benzene (Preparation 15, 4.39 g, 16.56 mmol) in dioxane (100 mL) was added bis(pinacolato)diboron (4.62 g, 18.21 mmol) and potassium acetate (4.88 g, 49.68 mmol). The resulting mixture was degassed then [1,1'-bis(diphenylphosphino)ferrocene]-dichloropalladium(II) (1.21 g, 1.66 mmol) was added and degassed again. The reaction mixture was heated at reflux for 3 hours and cooled to room temperature for 18 hours. Water (300 mL) was added to the reaction mixture, which was then filtered through celite and the celite washed with EtOAc (300 mL). The filtrate phases were separated and the organic layer was washed with brine (300 mL) then dried (Na$_2$SO$_4$), filtered and concentrated under reduced pressure. The residue was purified using silica gel column chromatography eluting with 20-50% EtOAc:heptane to afford the title compound as a yellow solid in 59% yield, 3.04 g.

$^1$H NMR (400 MHz, CDCl$_3$): δ ppm 1.36 (s, 12H), 3.04 (s, 3H), 3.91 (s, 3H), 7.36 (d, 1H), 7.49 (dd, 1H), 7.82 (d, 1H).

LCMS (System 13): Rt=2.71 minutes MS m/z 330 [M+NH$_4$]$^+$

Preparation 17

5'-Bromo-2'-fluoro-2-methoxy-4-(methylsulfonyl)-1,1'-biphenyl

A solution of 2-(2-methoxy-4-(methylsulfonyl)phenyl)-4,4,5,5-tetramethyl-1,3,2-dioxaborolane (Preparation 16, 3.04 g, 9.74 mmol), 5-bromo-2-fluoro-iodobenzene (2.66 g, 8.85 mmol), and Na$_2$CO$_3$ (2.80, 26.55 mmol) in dioxane (60 mL) and water (15 mL) was degassed, tetrakis(triphenylphosphine)palladium(0) was added and the reaction mixture was degassed again. The reaction mixture was heated at 110° C. for 3 hours before cooling to room temperature and concentrating under reduced pressure. The residue was partitioned between water (100 mL) and EtOAc (100 mL). The organic phase was separated and the aqueous layer was re-extracted with EtOAc (2×100 mL). The combined organic layers were dried (Na$_2$SO$_4$), filtered and concentrated under reduced pressure to give the crude. The crude was purified by silica gel column chromatography eluting with 10-30% EtOAc/heptane to afford the title compound in 71% yield, 2.25 g.

$^1$H NMR (400 MHz, CDCl$_3$): δ ppm 3.11 (s, 3H), 3.89 (s, 3H), 7.04 (t, 1H), 7.43-7.51 (m, 4H), 7.60 (dd, 1H).

$^{19}$F NMR (CDCl$_3$, 376 MHz): δ −116 ppm.

LCMS (System 13): Rt=3.10 minutes MS m/z no ionization.

Preparation 18

2-(6-Fluoro-2'-methoxy-4'-(methylsulfonyl)-[1,1'-biphenyl]-3-yl)-4,4,5,5-tetramethyl-1,3,2-dioxaborolane A solution of 5'-bromo-2'-fluoro-2-methoxy-4-(methylsulfonyl)-1,1'-biphenyl (Preparation 17, 2.25 g, 6.26 mmol), bis(pinacolato)diboron (1.75 g, 6.89 mmol) and potassium acetate (1.84 g, 18.78 mmol, 3 eq) in dioxane (75 mL) was degassed then [1,1'-bis(diphenylphosphino)ferrocene]dichloropalladium(II) (511 mg, 0.626 mmol) was added and the mixture was degassed again. The reaction mixture was heated at reflux for 18 hours. The reaction was cooled to room temperature, diluted with CH$_2$Cl$_2$ (100 mL), and filtered through celite and the celite washed with CH$_2$Cl$_2$. The filtrate was concentrated under reduced pressure to give the crude material, which was purified by silica gel column chromatography eluting with 15% to 30% EtOAc in heptane to afford the title compound as colourless oil in quantitative yield, 2.80 g.

¹H NMR (400 MHz, CDCl$_3$): δ ppm 1.33 (s, 12H), 3.10 (s, 3H), 3.87 (s, 3H), 7.13 (dd, 1H), 7.46-7.49 (m, 2H), 7.58 (dd, 1H), 7.75 (dd, 1H), 7.81-7.85 (m, 1H).

¹⁹F NMR (376 MHz, CDCl$_3$): δ −109 ppm.

LCMS (System 13): Rt=3.38 minutes MS m/z no ionisation.

Preparation 19

1-Bromo-4-(ethylsulfonyl)-2-fluorobenzene

To solution of 4-bromo-3-fluorobenzene-1-sulfonyl chloride (50 g, 0.184 mol) in THF (800 mL) at 0° C. was added hydrazine monohydrate (40-50%, 41.26 g, 0.644 mol) dropwise over 45 minutes. The reaction was stirred for 4 hours at room temperature and then the solvent was removed under reduced pressure to low volume. Heptane (100 mL) was added and the solid was filtered and washed several times with heptanes. The resulting solid was dissolved in ethanol (800 mL). Sodium acetate (90.56 g, 1.104 mol) and ethyl iodide (143.49 g, 0.92 mol) were added and the reaction heated to reflux for 18 hours. The reaction was allow to cool to room temperature, the solvent was removed under reduced pressure to 30% of the initial volume. The reaction mixture was diluted with water (500 mL) and extracted with CH$_2$Cl$_2$ (3×250 mL). The combined organic layers were washed with brine (2×300 mL), dried over Na$_2$SO$_4$, filtered and reduced to dryness to give a yellow oil. The crude was absorbed onto silica and purified (using siica gel column chromatography eluting with cyclohexane/EtOAc 8/2 to give the title compound as yellow solid in 64% yield, 31.70 g.

¹H NMR (400 MHz, CDCl$_3$): δ ppm 1.29 (t, 3H), 3.14 (q, 2H), 7.57-7.59 (m, 1H), 7.65 (dd, 1H), 7.89 (dd, 1H).

LCMS (System 13): Rt=2.26 minutes MS m/z no ionization.

Preparation 20

1-Bromo-4-(ethylsulfonyl)-2-methoxybenzene

In a sealed vessel 1-bromo-4-(ethylsulfonyl)-2-fluorobenzene (Preparation 19, 34.89 g, 0.131 mol) was dissolved in MeOH (400 mL) and sodium methoxide (35.3 g, 0.653 mol) was added. The reaction was heated at 100° C. for 12 hours and then allowed to cool to room temperature. The reaction mixture was diluted with water (750 mL) and the aqueous layer was extracted with CH$_2$Cl$_2$ (2×250 mL). The combined organic layers were washed with brine (300 mL), dried over Na$_2$SO$_4$, filtered and reduced to dryness to give a solid. The crude was purified by silica gel column chromatography eluting with cyclo-hexane/EtOAc gradient from 95/5 to 8/2 to afford the title compound as colourless solid in 75% yield, 27.32 g.

¹H NMR (400 MHz, CDCl$_3$): δ ppm 1.29 (t, 3H), 3.12 (q, 2H), 3.97 (s, 3H), 7.35-7.38 (m, 2H), 7.74 (d, 1H).

LCMS (System 13): Rt=2.26 minutes MS m/z no ionization.

1-Bromo-4-(ethylsulfonyl)-2-methoxybenzene may also be prepared according to the following Preparation:
Step 1

To a pre-cooled suspension of 2-bromo-5-fluorophenol (5 g, 26.18 mmol) and potassium carbonate (10.84 g, 78.54 mmol) in DMF (15 mL) at 0-5° C., was added methyl iodide (4.75 mL, 39.27 mmol) and the resulting reaction mixture was stirred at room temperature for 16 hours. The reaction mixture was partitioned between water (20 mL) and EtOAc (50 mL). The organic layer was separated and the aqueous layer was further extracted with EtOAc (3×50 mL). The organic layers were combined, washed with saturated brine solution (20 mL) and dried over Na$_2$SO$_4$, filtered and concentrated in vacuo to afford 1-bromo-4-fluoro-2-methoxybenzene as a colourless liquid in 93% yield, 5.00 g.

¹H NMR (400 MHz, DMSO-d$_6$): δ ppm 3.86 (s, 3H), 6.74-6.79 (m, 1H), 7.06 (dd, 1H), 7.57-7.65 (m, 1H).
Step 2

To a room temperature solution of 1-bromo-4-fluoro-2-methoxybenzene (5.00 g, 24.39 mmol) in DMF (15 mL) was added sodium ethanethiolate (2.66 g, 31.71 mmol) and the resulting reaction mixture was stirred for 72 hours. The reaction mixture was partitioned between water (20 mL) and EtOAc (50 mL). The organic layer was separated and the aqueous layer was further extracted with EtOAc (3×50 mL). The organic layers were combined and washed with saturated brine solution (20 mL) then dried over Na$_2$SO$_4$, filtered and concentrated in vacuo. The crude material was purified by silica gel column chromatography eluting with hexane:EtOAc 98:2 to afford 1-bromo-4-ethylthio-2-methoxybenzene as a colourless liquid in 17% yield, 1.00 g.

¹H NMR (400 MHz, DMSO-d$_6$): δ ppm 1.24 (t, 3H), 3.01 (q, 2H), 3.85 (s, 3H), 6.82 (dd, 1H), 6.98 (s, 1H), 7.48 (d, 1H) ppm.
Step 3

To a room temperature solution of 1-bromo-4-ethylthio-2-methoxybenzene (1.00 g, 4.05 mmol) in acetic acid (60 mL) was added sodium perborate monohydrate (889 mg, 8.91 mmol) and the resulting reaction mixture was stirred for 16 hours. The reaction was concentrated in vacuo and the resulting crude was partitioned between water (20 mL) and CH$_2$Cl$_2$ (50 mL). The organic layer was separated, washed with saturated brine solution (20 mL) then dried over Na$_2$SO$_4$, filtered and concentrated to afford the title product as a colorless liquid in 88% yield, 900 mg.

¹H NMR (400 MHz, DMSO-d$_6$): δ ppm 1.11 (t, 3H), 3.34 (q, 2H), 3.96 (s, 3H), 7.38 (dd, 1H), 7.47 (d, 1H), 7.88 (d, 1H).

Preparation 21

2-(4-(Ethylsulfonyl)-2-methoxyphenyl)-4,4,5,5-tetramethyl-1,3,2-dioxaborolane

A suspension of 1-bromo-4-(ethylsulfonyl)-2-methoxybenzene (Preparation 20, 2.00 g, 7.17 mmol), bis(pinacolato)diboron (3.16 g, 10.75 mmol), bis(diphenylphosphino)ferrocene]dichloropalladium(II) (293 mg, 0.359 mmol) and potassium acetate (1.76 g, 17.93 mmol) in dioxane (40 mL) was degassed with nitrogen for 20 minutes and placed on a pre-heated hot plate at 100° C. The reaction was stirred at 100° C. for 18 hours. The reaction was cooled to room temperature, filtered through celite and washed with EtOAc (50 mL). Water (75 mL) was added and the product extracted with EtOAc (2×50 mL), dried over Na$_2$SO$_4$, filtered and concentrated under vacuum. The residue was purified using silica gel column chromatography eluting with 15-65% tBME in heptanes to afford the title compound as a colourless solid in 42% yield, 985 mg.

¹H NMR (400 MHz, CDCl$_3$): δ ppm 1.22 (t, 3H), 1.33 (s, 12H), 3.08 (q, 2H), 3.85 (s, 3H), 7.27 (s, 1H), 7.43 (s, 1H), 7.99 (s, 1H).

Preparation 22

2-Bromo-5-(chlorosulfonyl) benzoic acid

2-Bromobenzoic acid (10.2 g, 50.8 mmol) was added in several portions to chlorosulfonic acid (50 mL) at 0° C. and the resulting solution held at this temperature for 15 minutes. The mixture was then heated at 115° C. for 16 hours. The reaction mixture was cooled to room temperature and was cautiously added drop-wise onto ice. The resulting suspension was allowed to reach room temperature and filtered. The solid was dried under vacuum at 40° C. for 16 hours. The title compound was obtained as a beige solid 85% yield, 12.8 g.

$^1$H NMR (400 MHz, CDCl$_3$): δ ppm 8.01 (m, 1H) 8.60 (s, 1H).

LCMS (System 13): Rt=2.26 minutes MS m/z no ionisation.

Preparation 23

2-Bromo-5-(isopropylsulfonyl)benzoic acid

Hydrazine hydrate (3.29 ml, 66.9 mmol) was added drop-wise to a solution of 2-bromo-5-(chlorosulfonyl) benzoic acid (Preparation 22, 10.0 g, 33.4 mmol) in THF (100 mL) at 0° C. Once the addition was complete the mixture was allowed to warm to room temperature and the solid was collected by filtration. The solid was washed with heptane (3×20 mL) and dried under vacuum at 50° C. for 18 hours. The solid was dissolved in EtOH (100 mL) and NaOAc (16.4 g, 198 mmol) and 2-iodopropane (16.7 mL, 165 mmol) were added. The mixture was heated to reflux for 16 hours, cooled to room temperature and the solvent was evaporated under reduced pressure to leave an off-white solid. The solid was partitioned between EtOAc (50 mL) and 1M NaOH (100 mL). The aqueous layer was separated, acidified to pH=1 with 2M HCl and extracted with EtOAc (3×50 mL). The combined EtOAc extracts were dried over MgSO$_4$ and the solvent was evaporated under reduced pressure to leave an orange oil. The oil was purified by silica gel column chromatography eluting with MeOH/CH$_2$Cl$_2$/AcOH 5:95.5:0.5 followed by a further chromatography eluting with heptanes/EtOAc 4:1 to give the title compound as a white solid 8% yield, 0.78 g.

$^1$H NMR (400 MHz, CDCl$_3$): δ ppm 1.34 (d, 6H) 3.24 (m, 1H) 7.86 (d, 1H) 7.92 (d, 1H) 8.45 (s, 1H).

LCMS (System 12): Rt=1.88 minutes MS m/z=307 [M+H]$^+$

Preparation 24

2-Bromo-5-(isopropylsulfonyl)benzamide

2-Bromo-5-(isopropylsulfonyl)benzoic acid (Preparation 23, 623 mg, 2.03 mmol) and HATU (925 mg, 2.44 mmol) were dissolved in DMF (10 mL) and diisopropylethylamine (1.74 mL, 10.0 mmol) was added dropwise to the mixture. The mixture was stirred for 1 hour and then partitioned between water (50 mL) and EtOAc (25 mL). The aqueous layer was extracted with EtOAc (2×10 mL) and the combined organic extracts were washed with saturated brine (20 mL) and dried (MgSO$_4$). The solvent was removed under reduced pressure to leave a pale yellow solid. This material was purified by silica gel column chromatography eluting with MeOH/CH$_2$Cl$_2$ 3:97 to give the title compound as a white solid 59% yield, 362 mg.

$^1$H NMR (400 MHz, DMSO-d$_6$): δ ppm 1.15 (d, 6H) 3.50 (m, 1H) 7.76 (m, 3H) 7.94 (dd, 1H) 8.08 (s, 1H).

LCMS (System 12): Rt=1.64 minutes MS m/z 306, 308 [M$^{79}$Br+H]$^+$

Preparation 25

2-Bromo-5-(isopropylsulfonyl)benzonitrile

Triethylamine (0.23 mL, 1.65 mmol) was added to a solution of 2-bromo-5-(isopropylsulfonyl)benzamide (Preparation 24, 338 mg, 1.11 mmol) in THF (10 mL) followed by trifluoroacetic anhydride (0.18 ml, 1.32 mmol). The reaction mixture was stirred at room temperature for 1 hour, diluted with EtOAc (30 mL) and washed with 2M NaHCO$_3$ (20 mL), brine (20 mL) and the organic layer was dried (MgSO$_4$). The solvent was evaporated under reduced pressure to give a colourless solid, 86% yield, 273 mg.

$^1$H NMR (400 MHz, CDCl$_3$): δ ppm 1.32 (d, 6H) 3.22 (m, 1H) 7.92 (m, 2H) 8.15 (t, 1H).

LCMS (System 12): Rt=2.45 minutes MS m/z no ionisation.

Preparation 26

4-Bromo-3-fluorobenzenethiol

A stirred ice-cooled solution of triphenylphosphine (23.0 g, 87.7 mmol), in CH$_2$Cl$_2$ (50 mL) and DMF (1.6 mL) was treated with a solution of 4-bromo-3-fluorobenzene-1-sulfonyl chloride (8.00 g, 29.2 mmol) in CH$_2$Cl$_2$ (50 mL) and stirred room temperature for 16 hours. The mixture was washed with 1N aqueous HCl (80 mL) and concentrated in vacuo. The resulting solid was diluted with 1N aqueous NaOH (160 mL), the solid filtered and the filtrate washed with 2-methoxy-2-methylpropane (3×150 mL) and acidified to pH 1 with 1M aqueous HCl. Extraction of the aqueous layer with 2-methoxy-2-methylpropane (3×100 mL), followed by drying over sodium sulphate and concentrating in vacuo gave the title compound as a yellow oil 66% yield, 3.97 g.

$^1$NMR (400 MHz, CDCl$_3$): δ ppm 3.53 (s, 1H), 6.92 (m, 1H), 7.04 (m, 1H), 7.39 (m, 1H).

LCMS (System 13): Rt=3.17 minutes MS m/z no ionisation.

Preparation 27

(4-Bromo-3-fluorophenyl)(cyclobutyl)sulfane

A stirred mixture of 4-bromo-3-fluorobenzenethiol (Preparation 26, 400 mg, 1.93 mmol), cesium carbonate (691 mg, 2.12 mmol) and bromocyclobutane (287 mg, 2.12 mmol) in DMSO (8 mL) was heated at 70° C. for 19 hours. The mixture was cooled to room temperature, poured into water (30 mL) and extracted with 2-methoxy-2-methylpropane (30 mL), washed with water (30 mL), dried over sodium sulfate and concentrated in vacuo. This gave the title compound as a colourless oil 95% yield, 480 mg.

$^1$H NMR (400 MHz, CDCl$_3$): δ ppm 1.75-1.90 (m, 6H), 3.63 (m, 1H), 6.61 (m, 1H), 6.70 (m, 1H), 7.17 (m, 1H) ppm.

Preparation 28

1-Bromo-4-(cyclobutylsulfonyl)-2-fluorobenzene 3-chlorobenzoperoxoic acid (1.12 g, 4.55 mmol) was added portionwise to an ice-cooled solution of (4-bromo-3-fluorophenyl)(cyclobutyl)sulfane (Preparation 27, 475 mg, 1.82 mmol) in CH$_2$Cl$_2$ (10 mL) and the mixture stirred at room temperature for 16 hours. The resulting precipitate was filtered off and the filtrate washed with aqueous 1N sodium hydroxide (3×10 mL), dried over Na$_2$SO$_4$ and concentrated in vacuo to give a solid. This material was purified by silica gel column chromatography eluting with CH$_2$Cl$_2$/heptanes 1:1 to 3:1 and the resulting solid triturated with heptane (5×2 mL) and dried in vacuo to give the title compound as a white solid 55% yield, 410 mg.

$^1$H NMR (400 MHz, CDCl$_3$): δ ppm 2.02 (m, 2H), 2.22 (m, 2H), 2.58 (m, 2H), 3.81 (m, 1H), 7.55 (m, 1H), 7.63 (m, 1H), 7.78 (m, 1H).

Preparation 29

1-Bromo-4-(cyclobutylsulfonyl)-2-methoxybenzene

Sodium (235 mg, 10.2 mmol) was added to MeOH (6 mL) under nitrogen and the mixture stirred until all the sodium had reacted. 1-bromo-4-(cyclobutylsulfonyl)-2-fluorobenzene (Preparation 28, 300 mg, 1.02 mmol) was added and the mixture stirred at 60° C. for 10 hours. 2% aqueous sodium bicarbonate (36 mL) was added and the mixture extracted with EtOAc (2×36 mL), the organic layers dried over sodium sulphate and then concentrated in vacuo. The resulting residue was purified by silica gel column chromatography eluting with CH$_2$Cl$_2$/EtOAc 3:1 to provide the title compound as a white solid 87% yield, 270 mg.

$^1$H NMR (400 MHz, CDCl$_3$): δ ppm 2.03 (m, 2H), 2.20 (m, 2H), 2.57 (m, 2H), 3.81 (m, 1H), 3.96, (m, 3H), 7.34 (m, 2H), 7.71 (m, 1H).

LCMS (System 11): Rt=3.07 minutes MS m/z no ionisation.

Preparation 30

2-(4-(Cyclobutylsulfonyl)-2-methoxyphenyl)-4,4,5,5-tetramethyl-1,3,2-dioxaborolane A mixture of 1-bromo-4-(cyclobutylsulfonyl)-2-methoxybenzene (Preparation 29, 345 mg, 1.13 mmol), bis(pinacolato)diboron (316 g, 1.24 mmol) and potassium acetate (332 mg, 2.26 mmol) in dioxane (6 mL) was purged with nitrogen for 10 minutes and then treated with 1,1'-bis(diphenylphosphino)ferrocene-palladium(II)dichloride (92 mg, 0.11 mmol). The reaction mixture was stirred at 80 C for 90 minutes. Further [1,1'-bis(diphenylphosphino)ferrocene]dichloropalladium(II) (300 mg, 0.04 mmol) and bis(pinacolato)diboron (115 mg, 0.45 mmol) were added and the reaction mixture stirred at 115° C. for 6 hours. The mixture was filtered through arbocel and evaporated to give a gum. This material was triturated with heptane (15 mL) to give a black solid which was isolated by filtration and the trituration was then repeated. The resulting solid was then stirred in heptanes (20 mL) at 70° C. for 30 minutes before filtering and drying in vacuo to give the title compound as a black solid 94% yield, 375 mg.

$^1$H NMR (400 MHz, CDCl$_3$): δ ppm 1.37 (s, 12H), 1.98 (m, 2H), 2.15 (m, 2H), 2.55 (m, 2H), 3.78, (m, 1H), 3.89 (s, 3H), 7.30 (d, 1H), 7.42 (m, 1H), 7.78 (m, 1H).

LCMS (System 11): Rt=3.25 minutes MS m/z no ionisation.

Preparation 31

(4-Bromo-3-fluorophenyl)(cyclopropyl)sulfane

A stirred mixture of 4-bromo-3-fluorobenzenethiol (Preparation 26, 400 mg, 1.93 mmol), potassium tert-butoxide (238 mg, 2.12 mmol) and bromocyclopropane (701 mg, 5.80 mmol) in DMSO (10 mL) was heated at 90° C. for 16 hours. Additional potassium tert-butoxide (43 mg, 0.386 mmol) and bromocyclopropane (467 mg, 3.86 mmol) were added and heating continued at 90° C. for 30 hours. The mixture was cooled to room temperature and poured into 2-methoxy-2-methylpropane (30 mL). The mixture was washed with water (2×30 mL), dried over Na$_2$SO$_4$, concentrated in vacuo and purified by silica gel column chromatography eluting with heptanes to give the title compound as a colourless oil 27% yield, 130 mg.

$^1$H NMR (400 MHz, CDCl$_3$): δ ppm 0.71-1.90 (m, 2H), 1.12 (m, 2H), 2.16 (m, 1H), 6.98 (m, 1H), 7.15 (m, 1H), 7.42 (m, 1H).

Preparation 32

1-Bromo-4-(cyclopropylsulfonyl)-2-fluorobenzene

3-Chlorobenzoperoxoic acid (307 mg, 1.25 mmol) was added portionwise to an ice-cooled solution of (4-bromo-3-fluorophenyl)(cyclopropyl)sulfane (Preparation 31, 123 mg, 0.50 mmol) in CH$_2$Cl$_2$ (3 mL) and stirred at room temperature for 5 hours.

The resulting precipitate was filtered and the filtrate concentrated in vacuo to give a solid. This solid was dissolved in EtOAc (10 mL), washed with 1M aqueous sodium hydroxide (8 mL), dried over Na$_2$SO$_4$ and concentrated in vacuo to give a white powder. This material was triturated with heptane (10 mL), filtered and dried under vacuum to give the title compound as a white solid 83% yield, 115 mg.

$^1$H NMR (400 MHz, CDCl$_3$): δ ppm 1.09 (m, 2H), 1.38 (m, 2H), 2.47 (m, 1H), 7.60 (m, 1H), 7.66 (m, 1H), 7.78 (m, 1H).

Preparation 33

1-Bromo-4-(cyclopropylsulfonyl)-2-methoxybenzene

Sodium (95 mg, 4.12 mmol) was added portionwise to MeOH (2 mL). After stirring at room temperature for 1 hour, this solution was added dropwise to a suspension of 1-bromo-4-(cyclopropylsulfonyl)-2-fluorobenzene (Preparation 32, 115 mg, 0.41 mmol) in MeOH (2 mL), and the resulting mixture stirred at 60° C. for 16 hours. After cooling to room temperature, water (10 mL) and CH$_2$Cl$_2$ (10 mL) were added, and the resulting mixture partitioned. The aqueous was extracted with CH$_2$Cl$_2$ (2×10 mL), and the combined organic layers washed with brine (20 mL), dried over MgSO$_4$ and concentrated in vacuo. Purification by silica gel column chromatography eluting with heptanes/CH$_2$Cl$_2$ 1:2 afforded the title compound as a colourless solid in 73% yield, 88 mg.

$^1$H NMR (400 MHz, CDCl$_3$): δ ppm 1.05 (m, 2H), 1.35 (m, 2H), 2.46 (m, 1H), 3.98 (s, 3H), 7.36 (m, 2H), 7.73 (d, 1H).

LCMS (System 13): Rt=2.76 minutes MS m/z no ionisation.

Preparation 34

1-Bromo-2-fluoro-4-(isopropylsulfonyl)benzene

To a solution of 4-bromo-3-fluorobenzene-1-sulfonyl chloride (5.40 mL, 36.5 mmol) in THF (150 mL) at 0° C. was added hydrazine monohydrate (6.20 mL, 63.9 mmol) dropwise under a nitrogen atmosphere. The reaction mixture was stirred for 1.5 hours. The solvent was removed in vacuo and replaced with heptanes (150 mL) and the resulting precipitate was collected by filtration. The solid was dissolved in industrial methylated spirit (150 mL) and to this solution was added sodium acetate (17.9 g, 218 mmol) and 2-bromopropane (17.2 mL, 183 mmol). The resultant reaction mixture was stirred at 85° C. for 16 hours under a nitrogen atmosphere. The reaction mixture was cooled to room temperature and quenched with water (300 mL) before being extracted with CH$_2$Cl$_2$ (3×300 mL). The combined organic extracts were washed with brine (300 mL), dried over MgSO$_4$, filtered and evaporated in vacuo. The crude material was purified by silica gel column chromatography eluting with EtOAc:heptanes 20/80 to afford title compound as a colourless solid in 12% yield, 1.19 g.

$^1$H NMR (400 MHz CDCl$_3$): δ ppm 1.30 (s, 3H), 1.32 (s, 3H), 3.20 (m, 1H), 7.55 (m, 1H), 7.63 (dd, 1H), 7.78 (dd, 1H).

LCMS (System 12): Rt=2.71 minutes MS m/z no ionisation.

Preparation 35

1-Bromo-4-(isopropylsulfonyl)-2-methoxybenzene

To dioxane (5 mL) and MeOH (0.216 mL) was added a solution of potassium tert-butoxide (1M in THF, 5.16 mL) and the mixture stirred for 15 minutes. To the mixture was added 1-bromo-2-fluoro-4-(isopropylsulfonyl)benzene (Preparation 34, 500 mg, 1.78 mmol) and the reaction mixture stirred for 16 hours at 60° C. The cooled reaction mixture was quenched with water (15 mL), and extracted with EtOAc (3×15 mL). The combined organic extracts were dried over MgSO$_4$, filtered and evaporated in vacuo. The crude material was purified by silica gel column chromatography eluting with EtOAc/heptanes 33/67-100/0 to afford title compound as a colourless solid in 75% yield.

$^1$H NMR (400 MHz, CDCl$_3$): δ ppm 1.31 (d, 6H), 3.20 (m, 1H), 3.95 (s, 3H), 7.32-7.35 (m, 2H), 7.74 (d, 1H).

Preparation 36

2-(4-(Isopropylsulfonyl)-2-methoxyphenyl)-4,4,5,5-tetramethyl-1,3,2-dioxaborolane To a solution of 1-bromo-4-(isopropylsulfonyl)-2-methoxybenzene (Preparation 35, 858 mg, 2.93 mmol) was added potassium acetate (862 mg, 8.78 mmol) and bis(pinacolato)diboron (817 mg, 3.22 mmol) and the reaction mixture was degassed with nitrogen for 30 minutes. 1,1'-Bis(diphenylphosphino)ferrocene palladium dichloride (119 mg, 0.15 mmol) was added and the reaction mixture was stirred at 110° C. for 16 hours under a nitrogen atmosphere. The cooled reaction mixture was filtered through celite then concentrated in vacuo. The residue was purified by silica gel column chromatography eluting with EtOAc:heptanes (0:100-50:50-100:0) to afford title compound as an off-white solid (1.30 g).

$^1$H NMR (400 MHz, CDCl$_3$): δ ppm 1.28 (d, 6H), 1.37 (s, 12H), 3.18 (m, 1H), 3.89 (s, 3H), 7.30 (d, 1H), 7.43 (dd, 1H), 7.81 (d, 1H).

Preparation 37

5'-Bromo-2'-fluoro-4-(isopropylsulfonyl)-2-methoxy-1,1-biphenyl

To a solution of 2-(4-(isopropylsulfonyl)-2-methoxyphenyl)-4,4,5,5-tetramethyl-1,3,2-dioxaborolane (Preparation 36, 374 mg, 1.10 mmol) and 5-bromo-2-fluoroiodobenzene (300 mg, 1.00 mmol) in dioxane (6 mL) and water (2.5 mL) was added sodium carbonate (317 mg, 3.00 mmol). The mixture was degassed with nitrogen for 20 minutes, tetrakis(triphenylphosphine)palladium(0) (58.0 mg, 0.05 mmol) was added and the reaction mixture was stirred at 100° C. under a nitrogen atmosphere for 12 hours. The cooled reaction mixture was diluted with water (10 mL) and extracted with EtOAc (3×10 mL). The combined organic extracts were dried over MgSO$_4$, filtered and evaporated in vacuo. The crude material was purified by silica gel column chromatography eluting with EtOAc/cyclohexane 25/75 to afford the title compound as a yellow oil in 69% yield, 0.27 g.

$^1$H NMR (400 MHz, CDCl$_3$): δ ppm 1.35 (d, 6H), 3.25 (m, 1H), 3.87 (s, 3H), 7.03 (t, 1H), 7.41-7.50 (m, 4H), 7.54 (d, 1H).

LCMS: (System 11): Rt=2.79 minutes MS m/z 406 [M$^{81}$Br+NH$_4$]$^+$

Preparation 38

2-(6-Fluoro-4'-(isopropylsulfonyl)-2'-methoxy-[1,1'-biphenyl]-3-yl)-4,4,5,5-tetramethyl-1,3,2-dioxaborolane To a solution of 5'-bromo-2'-fluoro-4-(isopropylsulfonyl)-2-methoxy-1,1'-biphenyl (Preparation 37, 267 mg, 0.69 mmol) and bis(pinacolato)diboron (193 mg, 0.76 mmol) in dioxane (10 mL) was added potassium acetate (202 mg, 2.07 mmol) and the reaction mixture was degassed with nitrogen for 20 minutes. 1,1'-Bis(diphenylphosphino)ferrocene palladium dichloride (28.0 mg, 0.03 mmol) was added and the reaction mixture was stirred at 110° C. for 14 hours under a nitrogen atmosphere. The cooled reaction mixture was filtered through celite then concentrated in vacuo. No further purification performed, the material was used directly in subsequent step. The title compound was afforded as a dark oil in quantitative yield, 299 mg.

$^1$H NMR (400 MHz, CDCl$_3$): δ ppm 1.26 (s, 12H), 1.35 (d, 6H), 3.24 (m, 1H), 3.86 (s, 3H), 7.14 (dd, 1H), 7.42-7.55 (m, 3H), 7.76 (dd, 1H), 7.84 (m, 1H).

LCMS (System 11): Rt=2.98 minutes MS m/z 452 [M+NH$_4$]$^+$

Preparation 39

5-Bromo-2-methyl-2,3-dihydro-1,2-benzisothiazole 1,1-dioxide

To a suspension of 5-bromo-2,3-dihydro-1,2-benzisothiazole 1,1-dioxide (200 mg, 0.92 mmol) and potassium carbonate (128 mg, 0.92 mmol) in EtOH (2 mL) was added iodomethane (0.2 mL, 3.2 mmol) and the reaction was stirred at room temperature for 18 hours followed by heating to 50° C. for 2 hours. The reaction was cooled, concentrated in vacuo and diluted with DCM (20 mL). The solution was washed with water (20 mL), dried over Na$_2$SO$_4$ and concentrated in vacuo to afford the title compound as a white solid (1.75 g, 83%).

$^1$H NMR (400 MHz, CDCl$_3$): δ ppm 2.98 (s, 3H), 4.34 (s, 2H), 7.58 (s, 1H), 7.70 (s, 2H).

LCMS Rt=2.54 minutes MS m/z 262 [M$^{79}$Br+H]$^+$

Preparation 40

Ethyl (3,5-dichloropyridazin-4-yl)imidoformate

To a stirred suspension of 3,5-dichloro-4-aminopyridazine (5 g, 31 mmol) in triethyl orthoformate (205 mL) was added pyridinium para-toluenesulfonate (387 mg, 1.5 mmol) and the resultant solution was heated at 100° C. for 16 hours. The reaction mixture was cooled to room temperature then evaporated in vacuo and the crude residue was purified by silica gel column chromatography eluting with hexane:EtOAc (80:20) to afford the title compound as a light brown oil in 60% yield, 4 g.

¹H NMR (400 MHz, DMSO-d₆): δ ppm 1.34 (t, 3H), 4.36 (q, 2H), 8.17 (s, 1H), 9.28 (s, 1H).
LCMS (System 7): Rt=2.92 minutes MS m/z 220 [M+H]⁺

Preparation 41

5'-Bromo-4-(ethylsulfonyl)-2'-fluoro-2-methoxy-1,1'-biphenyl

A suspension of 4-bromo-1-fluoro-2-iodobenzene (420 mg, 1.39 mmol), 2-(4-(ethylsulfonyl)-2-methoxyphenyl)-4,4,5,5-tetramethyl-1,3,2-dioxaborolane (Preparation 21, 500 mg, 1.53 mmol), 2M aqueous sodium carbonate solution (2.5 mL) and dioxane (10 mL) was degassed with nitrogen for 30 minutes. Tetrakis(triphenylphosphine)palladium(0) (80 mg, 0.07 mmol) was added and the reaction warmed to 110° C. and stirred for 1 hour. The reaction was cooled to room temperature, diluted with water (10 mL), extracted with EtOAc (2×10 mL), dried over Na₂SO₄, filtered and concentrated under vacuum. The residue was purified using silica gel column chromatography eluting with heptanes/EtOAc 7/3 to afford the title compound as a pale yellow solid in 73% yield, 418 mg.
¹H NMR (400 MHz, CDCl₃): δ ppm 1.37 (t, 3H), 3.18 (q, 2H), 3.82 (s, 3H), 7.03 (1H, dd), 7.46 (m, 4H), 7.59 (d, 1H).
LCMS (System 12): Rt=3.21 minutes MS m/z no ionization.

Preparation 42

2-(4'-(Ethylsulfonyl)-6-fluoro-2'-methoxy-[1,1'-biphenyl]-3-yl)-4,4,5,5-tetramethyl-1,3,2-dioxaborolane A suspension of 5'-bromo-4-(ethylsulfonyl)-2'-fluoro-2-methoxy-1,1-biphenyl (Preparation 41, 400 mg, 1.07 mmol), bis(pinacolato)diboron (300 mg, 1.18 mmol), bis(diphenylphosphino)ferrocene]dichloropalladium(II) (87.4 mg, 0.107 mmol) and potassium acetate (315 mg, 3.21 mmol) in dioxane (20 mL) were degassed with nitrogen for 20 minutes and placed on a pre-heated hot plate at 100° C. The reaction was stirred at 100° C. for 18 hours, cooled to room temperature, filtered through celite and washed with CH₂Cl₂ (10 mL). Water (20 mL) was added and the aqueous layer was extracted with CH₂Cl₂ (2×10 mL). The combined organic layers were dried over Na₂SO₄, filtered and concentrated under vacuum. The residue was purified using silica gel column chromatography eluting with heptanes:EtOAc 8:2 to afford the title compound as a pale yellow solid in 93% yield 391 mg.
¹H NMR (400 MHz, CDCl₃): δ ppm 1.36 (t, 3H), 1.37 (12H, s), 3.19 (q, 2H), 3.82 (s, 3H), 7.14 (dd, 1H), 7.41 (m, 2H), 7.49 (d, 1H), 7.73 (d, 1H), 7.82 (dd, 1H).
LC (System 12): Rt=3.49 minutes Preparation 43

5'-Bromo-2'-fluoro-N-methylbiphenyl-4-sulfonamide

To a solution of 4-bromo-1-fluoro-2-iodobenzene (207 mg, 0.69 mmol) in anhydrous dioxane (3.4 mL) was added [4-(methylsulfamoyl)phenyl]boronic acid (148 mg, 0.69 mmol) and aqueous Na₂CO₃ solution (2M, 1.03 mL, 2.06 mmol). A stream of nitrogen gas was bubbled through the reaction mixture for 6 minutes. Tetrakistriphenylphosphine palladium(0) (24 mg, 0.021 mmol) was added and the mixture was heated under microwave irradiation at 120° C. for 12 minutes. The reaction mixture was cooled, diluted with EtOAc, treated with anhydrous Na₂SO₄ and filtered, washing the solids with EtOAc until the compound had completely eluted. The filtrate was evaporated in vacuo. The residue was purified by silica gel column chromatography eluting with heptane:EtOAc 100:0 to 60:40 to afford the title compound as clear, colorless residue in 67% yield, 159 mg.
¹H NMR (500 MHz, CDCl₃): δ ppm 2.74 (d, 3H), 4.38 (q, 1H), 7.10 (dd, 1H), 7.51 (ddd, 1H), 7.59 (dd, 1H), 7.66-7.71 (m, 2H), 7.93-7.98 (m, 2H).
LCMS (System 8) Rt=3.40 minutes MS m/z 344 [M+H]⁺

Preparation 44

2'-Fluoro-N-methyl-5'-(4,4,5,5-tetramethyl-1,3,2-dioxaborolan-2-yl)biphenyl-4-sulfonamide 5'-Bromo-2'-fluoro-N-methylbiphenyl-4-sulfonamide (Preparation 43, 157 mg, 0.46 mmol), bis(pinacolato)diboron (128 mg, 0.50 mmol), and potassium acetate (134 mg, 1.37 mmol) were suspended in anhydrous dioxane that contained 1% dimethylsulfoxide (v/v) (2.30 mL) in a microwave vial and a stream of nitrogen gas was bubbled through the suspension for 5 minutes. Dichloro[1,1'-bis(diphenylphosphino)ferrocene]palladium(II) (19 mg, 0.023 mmol) was then added, the vial sealed, and the red mixture heated at 100° C. for 18 hours. The reaction mixture was cooled and diluted with EtOAc (30 mL) and water (30 mL) and filtered through a celite plug. The organic phase was extracted and the aqueous layer was back-extracted with EtOAc (2×10 mL). The organics were combined, washed with brine (10 mL), dried over Na₂SO₄, filtered and the filtrate was evaporated in vacuo. The residue was purified using silica gel column chromatography eluting with heptane:EtOAc 100:0 to 60:40 to afford the title compound as a light tan solid in 86% yield, 153 mg.
¹H NMR (500 MHz, CDCl₃): δ ppm 1.36 (s, 12H), 2.72 (d, 3H), 4.25-4.43 (m, 1H), 7.19 (dd, 1H), 7.74 (dd, 2H), 7.82-7.87 (m, 1H), 7.89-7.96 (m, 3H).
LCMS (System 8) Rt=3.77 minutes MS m/z 392 [M+H]⁺

Preparation 45

2-[4-(Ethylsulfonyl)-2-fluorophenyl]-4,4,5,5-tetramethyl-1,3,2-dioxaborolane

1-Bromo-4-(ethylsulfonyl)-2-fluorobenzene (Preparation 19, 200 mg, 0.75 mmol), bis(pinacolato)diboron (200 mg, 0.79 mmol), and potassium acetate (220 mg, 2.25 mmol) were suspended in dimethylsulfoxide (5.0 mL) and a stream of nitrogen gas was bubbled through the suspension for 5 minutes. Dichloro[1,1'-bis(diphenylphosphino)ferrocene]palladium(II) (18 mg, 0.022 mmol) was then added and the mixture was heated at 90° C. 16.5 hours. The reaction mixture was cooled and diluted with EtOAc (30 mL) and half-saturated aqueous brine solution (10 mL). The organic phase was extracted and the aqueous layer was back-extracted with EtOAc (10 mL). The organic layers were combined, dried over Na₂SO₄, filtered and the filtrate was evaporated in vacuo. The resulting material was purified by silica gel column chromatography eluting with heptane:EtOAc 100:0 to 1:1 to afford the title compound as a light yellow solid in 70% yield, 170 mg.
¹H NMR (500 MHz, CDCl₃): δ ppm 1.27-1.30 (m, 3H), 1.39 (s, 12H), 3.13 (q, 2H), 7.58 (dd, 1H), 7.68 (dd, 1H), 7.95 (dd, 1H).

Preparation 46

5'-Bromo-4-(ethylsulfonyl)-2,2'-difluorobiphenyl

To a solution of 2-[4-(ethylsulfonyl)-2-fluorophenyl]-4,4,5,5-tetramethyl-1,3,2-dioxaborolane (Preparation 45, 102 mg, 0.33 mmol) and 4-bromo-1-fluoro-2-iodobenzene (108 mg, 0.36 mmol) in toluene (0.56 mL) and ethanol (0.14 mL) was added aqueous $Na_2CO_3$ solution (1M, 0.55 mL, 0.55 mmol). A stream of nitrogen gas was bubbled through the reaction mixture for 5 minutes. Dichloro[1,1'-bis(diphenylphosphino)ferrocene]palladium(II) (13 mg, 0.016 mmol) was then added, and the mixture was heated at 80° C. for 1 hour. The reaction mixture was cooled, diluted with water (20 mL) and extracted with EtOAc (3×20 mL). The combined organic layers were washed with brine, dried over anhydrous $Na_2SO_4$, filtered, and the filtrate was evaporated in vacuo. The residue was purified by silica gel column chromatography eluting with heptane:EtOAc 100:0 to 70:30 to afford the title compound as a light yellow solid in 57% yield, 67 mg.

$^1$H NMR (500 MHz, $CDCl_3$): δ ppm 1.36 (t, 3H), 3.19 (q, 2H), 7.12 (t, 1H), 7.53-7.59 (m, 2H), 7.61 (t, 1H), 7.75 (dd, 1H), 7.80 (dd, 1H).

GCMS Rt=5.39 minutes MS m/z 361 $[M^{79}Br+H]^+$

Preparation 47

2-[4'-(Ethylsulfonyl)-2',6-difluorobiphenyl-3-yl]-4,4,5,5-tetramethyl-1,3,2-dioxaborolane Prepared according to the method described for Preparation 42 using 5'-bromo-4-(ethylsulfonyl)-2,2'-difluorobiphenyl (Preparation 46) and bis(pinacolato)diboron to afford the title compound as a light yellow solid in 62% yield, 53 mg.

$^1$H NMR (500 MHz, $CDCl_3$): δ ppm 1.34 (t, 3H), 1.36 (s, 12H), 3.18 (q, 2H), 7.21 (dd, 1H), 7.64 (m, 1H), 7.72 (dd, 1H), 7.77 (dd, 1H), 7.82-7.86 (m, 1H), 7.88-7.93 (m, 1H).

Preparation 48

2-(4'-Ethylsulfonyl-6-fluorobiphenyl-3-yl)-4,4,5,5-tetramethyl[1,3,2]dioxaborolane A solution of 1,1'-bis(diphenylphosphino) ferrocene palladium dichloride (314 mg, 0.38 mmol), potassium acetate (2.26 g, 23.1 mmol), bis(pinacolato)diboron (2.15 g, 8.46 mmol) and 5'-bromo-2'-fluorobiphenyl-4-yl ethyl sulfone (Preparation 49, 2.64 g, 7.71 mmol) in anhydrous dioxane (80 mL) was then heated at 120° C. for 5 hours. The reaction mixture was cooled to room temperature then filtered through celite and washed with $CH_2Cl_2$ (100 mL). The filtrate was evaporated in vacuo to give a crude product as a dark brown oil. The residue was purified by silica gel column chromatography eluting with heptane:EtOAc 1:1 to afford the title compound as an off white solid in 72% yield, 2.15 g.

$^1$H NMR (400 MHz, $CDCl_3$): δ ppm 1.31 (t, 3H), 1.35 (s, 12H), 3.15 (q, 2H), 7.18 (dd, 1H), 7.75-7.79 (m, 2H), 7.84 (ddd, 1H), 7.90 (dd, 1H), 7.94-7.98 (m, 2H).

LCMS (System 1): Rt=2.95 minutes MS m/z 391[M+H]$^+$

Preparation 49

5'-Bromo-2'-fluorobiphenyl-4-yl ethyl sulfone

To a degassed, room temperature solution of 4-bromo-1-fluoro-2-iodobenzene (2.80 g, 9.30 mmol) and 4-(ethylsulphonyl)benzeneboronic acid (2.27 g, 10.6 mmol), in anhydrous 1,4-dioxane (120 mL) was added aqueous $Na_2CO_3$ solution (1M, 46.5 mL, 46.5 mmol) followed by the tetrakistriphenylphosphine palladium(0) (537 mg, 0.465 mmol). The slightly yellow solution was degassed 3 times by vacuum/nitrogen refill then was heated to 100° C. with stirring for 2 hours. The reaction mixture was cooled then suspended in $CH_2Cl_2$ (50 mL) and filtered through a pad of celite. The pad was rinsed well with $CH_2Cl_2$ (100 mL) and the filtrate was washed with water (2×50 mL) then dried over anhydrous $MgSO_4$ (s), filtered and evaporated in vacuo to give crude product as a yellow oil. Purification by silica gel column chromatography eluting with heptane:EtOAc 1:1 afforded the title compound as a colourless oil in 84% yield, 2.696 g.

$^1$H NMR (400 MHz, $CDCl_3$): δ ppm 1.32 (t, 3H), 3.19 (q, 2H), 7.09 (dd, 1H), 7.50 (ddd, 1H), 7.59 (dd, 1H), 7.71 (d, 2H), 7.98 (d, 2H).

LCMS (System 4): Rt=1.37 minutes MS m/z 345 $[M^{81}Br+H]^+$

Preparation 50

1-Bromo-2-(difluoromethyl)-4-fluorobenzene

To a solution of 2-bromo-5-fluorobenzaldehyde (1.00 g, 4.92 mmol) in $CH_2Cl_2$ (10 mL) at 0° C. was added a solution of diethylaminosulfur trifluoride (0.98 mL, 7.38 mmol) in $CH_2Cl_2$ (5 mL). The reaction was allowed to warm to room temperature and stirred for 18 hours. The reaction mixture was poured into a saturated aqueous solution of $NaHCO_3$ (10 mL) and the organics were extracted with $CH_2Cl_2$ (2×20 mL), dried over $Na_2SO_4$, filtered and concentrated under vacuum to afford the title compound as an orange oil (928 mg, 84%).

$^1$H NMR (400 MHz, $CDCl_3$): δ ppm 6.81 (t, 1H), 7.04 (m, 1H), 7.37 (dd, 1H), 7.58 (m, 1H).

$^{19}$F NMR (376 MHz, $CDCl_3$): δ −115.7 (d, 2F), −112.1 (s, 1F) ppm.

LCMS (System 12): Rt=2.87 minutes MS m/z no ionization.

Preparation 51

(4-Bromo-3-(difluoromethyl)phenyl)(ethyl)sulfane

1-Bromo-2-(difluoromethyl)-4-fluorobenzene (Preparation 50, 772 mg, 3.43 mmol) and sodium ethanethiolate (352.7 mg, 3.77 mmol) in DMSO (5 mL) was heated at 50° C. for 18 hours. On cooling, water (70 mL) was added to the reaction mixture, the product was extracted with EtOAc (20 mL×3). The combined organic layers were concentrated to give the crude product, which was purified by silica gel column chromatography eluting with heptane to afford the title compound as a colourless oil (260 mg, 28%).

$^1$H NMR (400 MHz, $CDCl_3$): δ ppm 1.33 (3H, t), 2.98 (2H, q), 6.88 (1H, t), 7.25 (1H, d), 7.50 (1H, d), 7.56 (1H, s).

LCMS (System 12): Rt=3.40 minutes MS m/z no ionization.

Preparation 52

1-Bromo-2-(difluoromethyl)-4-(ethylsulfonyl)benzene

A solution of (4-bromo-3-(difluoromethyl)phenyl)(ethyl) sulfane (Preparation 51, 260 mg, 0.97 mmol) and 3-chloroperoxybenzoic acid (722 mg, 2.92 mmol) in $CH_2Cl_2$ (10 mL) was stirred for 66 hours. Potassium carbonate (2M, 20 mL)

was added and the aqueous phase was extracted with $CH_2Cl_2$ (20 mL×2). The combined organic layers were concentrated and the product was purified by reverse phase column chromatography eluting with acetonitrile+0.1% formic acid and water+0.1% formic acid 3:97 to 60:40 to give the title compound as colourless oil 35%, 120 mg.

$^1$H NMR (400 MHz, CDCl$_3$): δ ppm 1.30 (3H, t), 3.16 (2H, q), 6.94 (1H, t), 7.04-7.89 (2H, m), 8.19 (1H, s).

LCMS (System 12): Rt=2.56 minutes MS m/z no ionization.

Preparation 53 tert-Butyl(4-chloro-3-iodophenoxy)dimethylsilane

To a solution of 4-chloro-3-iodophenol (2 g. 7.86 mmol) in anhydrous 2-methyltetrahydrofuran (10 mL) was added tert-butyldimethylsilyl chloride (1.25 g, 8.28 mmol) followed by imidazole (642 mg, 68.1 mmol) The resulting mixture was stirred at room temperature for 3 hours. EtOAc (10 mL) was added and the mixture washed with aqueous sodium hydroxide solution (2M, 3×10 mL), water (10 mL), and brine (10 mL), dried over Na$_2$SO$_4$ and concentrated in vacuo. The residue was purified by silica gel column chromatography eluting with heptane:EtOAc 90:10 to afford the title compound as colourless oil in 30% yield, 870 mg.

$^1$H NMR (400 MHz, CDCl$_3$): δ ppm 0.00 (s, 6H), 0.78 (s, 9H), 6.57 (dd, 1H), 7.07 (d, 1H), 7.17 (d, 1H).

LCMS (System 11) Rt=3.55 minutes no ionization.

Preparation 54

6-Chloro-4'-(ethylsulfonyl)-2'-methoxy-[1,1'-biphenyl]-3-ol

A solution of tert-butyl(4-chloro-3-iodophenoxy)dimethylsilane (Preparation 53, 102 mg, 0.28 mmol), 2-(4-(ethylsulfonyl)-2-methoxyphenyl)-4,4,5,5-tetramethyl-1,3,2-dioxaborolane (Preparation 21) (90 mg, 0.28 mmol) and aqueous caesium carbonate solution (1M, 0.55 mL, 0.55 mmol) in dioxane (4 mL) was degassed with nitrogen for 10 minutes, followed by the addition of 1,1'-bis(diphenylphosphino)ferrocene-palladium(II)dichloride (11.0 mg, 0.014 mmol). The resulting mixture was heated at 100° C. for 3 hours and then cooled to room temperature. The mixture was partitioned between water (15 mL) and EtOAc (15 mL), the aqueous layer then extracted with EtOAc (2×15 mL). The organic layers were combined and washed with brine (25 mL), dried over MgSO$_4$ and then concentrated in vacuo. 4M HCl in dioxane (4 mL) was added to the residue, and the mixture stirred at room temperature for 40 hours. After concentration in vacuo, NH$_3$ solution (7M in MeOH, 2 mL) was added to the residue, and the mixture re-concentrated in vacuo. The residue was purified by silica gel column chromatography eluting with cyclohexane/EtOAc 70:30 to afford the title compound as yellow gum in 72% yield, 65 mg.

$^1$H NMR (400 MHz, CDCl$_3$): δ ppm 1.35 (t, 3H), 3.19 (q, 2H), 3.85 (s, 3H), 5.23 (br s, 1H), 6.75 (d, 1H), 6.82 (dd, 1H), 7.31 (d, 1H), 7.35 (d, 1H), 7.45 (d, 1H), 7.54 (dd, 1H).

LCMS (System 13): Rt=2.30 minutes MS m/z 325 [M−H]$^-$

Preparation 55

6-Chloro-4'-(ethylsulfonyl)-2'-methoxy-[1,1'-biphenyl]-3-yl trifluoromethanesulfonate To an ice-cooled solution of 6-chloro-4'-(ethylsulfonyl)-2'-methoxy-[1,1-biphenyl]-3-ol (Preparation 54, 100 mg, 0.31 mmol) and 2,6-lutidine (42.0 μL, 0.37 mmol) in CH$_2$Cl$_2$ was added trifluoromethanesulfonic anhydride (62.0 μL, 0.37 mmol). The resulting mixture was stirred at room temperature for 1 hour. Additional 2,6-lutidine (21.0 μL, 0.19 mmol) and trifluoromethanesulfonic anhydride (31.0 μL, 0.19 mmol) were added, and the mixture stirred for a further 1 hour. After concentration in vacuo, the residue was purified by silica gel column chromatography eluting with cyclohexane/EtOAc 70:30 to afford the title compound as yellow oil in 96% yield, 135 mg.

$^1$H NMR (400 MHz, CDCl$_3$): δ ppm 1.36 (t, 3H), 3.19 (q, 2H), 3.87 (s, 3H), 7.22 (d, 1H), 7.25-7.28 (m, 1H), 7.40 (d, 1H), 7.49 (d, 1H), 7.57 (m, 2H).

$^{19}$F NMR (376 MHz, CDCl$_3$): δ −72.7 (s) ppm.

LCMS (System 12): Rt=3.28 minutes MS m/z no ionization.

Preparation 56

2-(6-Chloro-4'-(ethylsulfonyl)-2'-methoxy-[1,1'-biphenyl]-3-yl)-4,4,5,5-tetramethyl-1,3,2-dioxaborolane A solution of 6-chloro-4'-(ethylsulfonyl)-2'-methoxy-[1,1'-biphenyl]-3-yl trifluoromethanesulfonate (Preparation 55, 130 mg, 0.28 mmol), bis(pinacolato)diboron (86.0 mg, 0.34 mmol) and potassium acetate (97.0 mg, 3.50 mmol) in anhydrous dioxane (5 mL) was degassed with nitrogen for 10 minutes, followed by the addition of 1,1'-bis(diphenylphosphino)ferrocene-palladium(II)dichloride (23.0 mg, 0.028 mmol). The resulting mixture was heated at 80° C. for 1 hour. Additional 1,1'-bis(diphenylphosphino)ferrocene-palladium(II)dichloride (23.0 mg, 0.028 mmol) was added, and the mixture heated for a further 1 hour. After cooling to room temperature and concentrated in vacuo, the residue was purified by silica gel column chromatography eluting with $CH_2Cl_2$ to afford the title compound as light yellow oil in 40% yield, 50 mg.

$^1$H NMR (400 MHz, CDCl$_3$): δ ppm 1.33 (m, 15H), 3.17 (q, 2H), 3.85 (s, 3H), 7.38 (d, 1H), 7.44 (d, 1H), 7.47 (d, 1H), 7.54 (dd, 1H), 7.67 (d, 1H), 7.75 (dd, 1H).

Preparation 57

4-Bromo-2-iodo-1-methoxybenzene

Iodomethane (103 μL, 1.65 mmol) was added to a solution of 4-bromo-2-iodophenol (450 mg, 1.51 mmol) and potassium carbonate (271 mg, 1.96 mmol) in acetone (10 mL). The resulting mixture was stirred at room temperature for 16 hours.

After concentration in vacuo, the mixture was partitioned between water (20 mL) and EtOAc (20 mL), and the aqueous layer extracted with EtOAc (2×15 mL). The organics layers were combined and washed with brine (20 mL), dried over MgSO$_{4 (s)}$, and concentrated in vacuo, to afford the title compound as an orange oil in 93% yield, 439 mg.

$^1$H NMR (400 MHz, CDCl$_3$): δ ppm 3.86 (s, 3H), 6.68 (d, 1H), 7.41 (dd, 1H), 7.88 (d, 1H).

LCMS (System 13): Rt=2.73 minutes MS m/z no ionization.

Preparation 58

5'-Bromo-4-(ethylsulfonyl)-2,2'-dimethoxy-1,1-biphenyl

A solution of 4-bromo-2-iodo-1-methoxybenzene (Preparation 57, 350 mg, 1.12 mmol), 2-(4-(ethylsulfonyl)-2-methoxyphenyl)-4,4,5,5-tetramethyl-1,3,2-dioxaborolane (Preparation 21, 365 mg, 1.12 mmol) and aqueous caesium carbonate solution (1M, 2.23 mL, 2.23 mmol) in dioxane (18 mL) was degassed with nitrogen for 10 min, followed by addition of 1,1'-bis(diphenylphosphino)ferrocene-palladium (II)dichloride (46.0 mg, 0.0056 mmol). The resulting mixture was heated at 80° C. for 16 hours. After cooling to room temperature and concentration in vacuo, the crude residue was partitioned between water (30 mL) and EtOAc (30 mL). The aqueous layer was extracted with EtOAc (2×20 mL). The organic layers were combined and washed with brine (25 mL), dried over $MgSO_4$ and concentrated in vacuo. The residue was purified by silica gel column chromatography eluting with heptanes/EtOAc (70:30), to afford the title compound as off-white solid in 45% yield, 150 mg.

$^1$H NMR (400 MHz, $CDCl_3$): δ ppm 1.35 (t, 3H), 3.16 (q, 2H), 3.75 (s, 3H), 3.87 (s, 3H), 6.86 (d, 1H), 7.32 (d, 1H), 7.39 (d, 1H), 7.45 (m, 2H), 7.52 (dd, 1H).

LCMS (System 13): Rt=2.58 minutes MS m/z no ionization.

Preparation 59

2-(4'-(Ethylsulfonyl)-2',6-dimethoxy-[1,1'-biphenyl]-3-yl)-4,4,5,5-tetramethyl-1,3,2-dioxaborolane A solution of 5'-bromo-4-(ethylsulfonyl)-2,2'-dimethoxy-1,1'-biphenyl (Preparation 58, 150 mg, 0.39 mmol), bis(pinacolato)diboron (119 mg, 0.47 mmol) and potassium acetate (134 mg, 1.36 mmol) in anhydrous dioxane (8 mL) was degassed with nitrogen for 10 minutes, followed by the addition of 1,1'-bis(diphenylphosphino)ferrocene-palladium(II) dichloride (32 mg, 0.039 mmol). The resulting mixture was heated at 90° C. for 9 hours. After cooling to room temperature, the mixture was partitioned between water (30 mL) and EtOAc (20 mL). The aqueous layer was extracted with EtOAc (3×20 mL). The organic layers were combined and washed with brine (30 mL), dried over $MgSO_4$, and concentrated in vacuo. The residue was purified by silica gel column chromatography eluting with $CH_2Cl_2$/heptanes/EtOAc 55:40:5 to afford the title compound as white solid in 62% yield, 105 mg.

$^1$H NMR (400 MHz, $CDCl_3$): δ ppm 1.32 (m, 15H), 3.16 (q, 2H), 3.80 (s, 3H), 3.83 (s, 3H), 6.98 (d, 1H), 7.41 (m, 2H), 7.51 (dd, 1H), 7.63 (d, 1H), 7.84 (dd, 1H).

LCMS (System 11): Rt=2.82 minutes MS m/z 433 [M+H]$^+$

Preparation 60

2-(3-Bromophenyl)-2,3-dihydro-1H-1,3-diaza-2-boraphenalene

A solution of 3-bromobenzene boronic acid (20 g, 0.1 mol) and naphthalene-1,8-diamine (17.3 g, 0.11 mol) in anhydrous toluene (600 mL) was heated to reflux for 16 hours. The reaction mixture was cooled to room temperature, then concentrated in vacuo. The residue was purified by silica gel column chromatography eluting with petroleum ether:EtOAc 5:1 to afford the title compound as a grey solid in 54% yield, 23 g.

$^1$H NMR (400 MHz, $CDCl_3$): δ ppm 5.91 (s, 2H), 6.35 (d, 2H), 7.00 (d, 2H), 7.06-7.09 (m, 2H), 7.24-7.26 (m, 1H), 7.47-7.55 (m, 2H), 7.69 (s, 1H).

Preparation 61

2-[3-(4,4,5,5-Tetramethyl-[1,3,2]dioxaborolan-2-yl)phenyl]-2,3-dihydro-1H-1,3-diaza-2-boraphenalene To a room temperature solution of 2-(3-bromophenyl)-2,3-dihydro-1H-1,3-diaza-2-boraphenalene (Preparation 60, 23 g, 0.071 mol), bis(pinacolato)diboron (22 g, 0.086 mol) and tricyclohexylphosphine (1 g, 3.6 mmol) in anhydrous dioxane (400 mL) was added and potassium acetate (28 g, 0.284 mol). The resultant solution was degassed. Then bis (dibenzylideneacetone) dipalladium(2 g, 36 mmol) was added in one portion, and the reaction mixture was purged with nitrogen three times before being stirred at reflux for 16 hours. The reaction mixture was cooled to room temperature then concentrated in vacuo. The residue was purified by silica gel column chromatography eluting with petroleum ether: EtOAc 5:1 to afford the title compound as a yellow solid in 61% yield, 16 g.

$^1$H NMR (400 MHz, $CDCl_3$): δ ppm 1.37 (s, 12H), 6.12 (d, 1H), 6.43 (d, 2H), 7.04-7.16 (m, 4H), 7.41-7.42 (m, 1H), 7.72-7.77 (m, 1H), 7.89-7.90 (m, 1H), 8.09 (s, 1H).

Preparation 62

2-[3-(7-Ethyl-7H-imidazo[4,5-c]pyridazin-4-yl)phenyl]-2,3-dihydro-1H-1,3-diaza-2-boraphenalene A room temperature solution of 2-[3-(4,4,5,5-tetramethyl-[1,3,2]dioxaborolan-2-yl)phenyl]-2,3-dihydro-1H-1,3-diaza-2-boraphenalene (Preparation 61, 7.8 g, 21.1 mmol), 4-chloro-7-ethyl-7H-imidazo[4,5-c]pyridazine (Preparation 8, 2.6 g, 14.1 mmol) and cesium carbonate (13.8 g, 42.3 mmol) in dioxane (160 mL) and water (13 mL) was degassed. 1,1'-bis(di-tert-butylphosphino) ferrocene palladium dichloride (0.91 g, 1.4 mmol) was then added in one portion and the reaction mixture was again purged with nitrogen gas three times. The resultant solution was then stirred at reflux for 16 hours. The reaction mixture was cooled to room temperature then filtered and concentrated in vacuo. The residue was purified by silica gel column chromatography eluting with $CH_2Cl_2$:MeOH, 50:1 to afford the title compound as a yellow solid in 83.6% yield.

$^1$H NMR (400 MHz, $CDCl_3$): δ ppm 1.69 (t, 3H), 4.58 (q, 2H), 6.23 (s, 2H), 6.44 (d, 2H), 7.06 (d, 2H), 7.12-7.16 (m, 2H), 7.61-7.65 (m, 1H), 7.76 (d, 1H), 8.21 (d, 1H) 8.28 (s, 1H), 8.45 (s, 1H), 9.39 (s, 1H).

Preparation 63

3-(7-Ethyl-7H-imidazo[4,5-c]pyridazin-4-yl)benzeneboronic acid

To a room temperature solution of 2-[3-(7-ethyl-7H-imidazo[4,5-c]pyridazin-4-yl)-phenyl]-2,3-dihydro-1H-1,3-diaza-2-boraphenalene (Preparation 62, 10.5 g, 26.9 mmol) in THF (400 mL) was added 5N hydrogen chloride aqueous solution (110 mL, 0.55 mol) and the resultant reaction mixture stirred at reflux for 16 hours. After cooling to room temperature, the reaction mixture was filtered and the filtrate was neutralized with potassium carbonate until pH=6. The resulting precipitate was filtered and the filter cake was washed with a small quantity of EtOAc. The collected solid was dried under vacuum to afford the title compound as an off white solid in 62.4% yield, 4.5 g. Taken directly on to the next step.

Preparation 64

2-(4'-Ethylsulfonyl-6-fluorobiphenyl-3-yl)-2,3-dihydro-1H-1,3-diaza-2-boraphenalene To a room temperature solution of 4-(ethylsulphonyl)benzeneboronic acid (0.90 g, 4.22 mmol) in anhydrous DMF (20 mL) was added 2-(3-chloro-4-fluorophenyl)-2,3-dihydro-1H-1,3-diaza-2-boraphenalene (Preparation 81, 1.00 g, 3.37 mmol) and potassium phosphite (2.87 g, 13.5 mmol) and the reaction mixture was degassed with argon for 30 minutes. To this was added 2-dicyclohexylphosphino-2',6'-dimethoxybiphenyl (276.7 mg, 0.67 mmol) followed by the tris(dibenzilideneacetone)palladium(0) (154 mg, 0.168 mmol) and the resultant solution was heated to 100° C. with stirring for 12 hours. The reaction mixture was cooled then filtered through a pad of celite. The pad was rinsed well with EtOAc (100 mL) and the filtrate was washed with water (2×50 mL) then saturated brine solution and dried over anhydrous $MgSO_4$ (s), filtered and evaporated in vacuo to give crude product as a yellow oil. The residue was purified by silica gel column chromatography eluting with $CH_2Cl_2$:MeOH 98:2 to afford the title compound as a colourless oil in 42% yield, 600 mg.

$^1$H NMR (400 MHz, $CDCl_3$): δ ppm 1.31 (t, 3H), 3.18 (q, 2H), 5.99 (s, 1H), 6.42 (d, 2H), 7.07 (d, 2H), 7.14 (t, 2H), 7.68-7.70 (m, 2H), 7.78 (d, 2H), 8.00 (d, 2H).

Preparation 65

(4'-Ethylsulfonyl-6-fluorobiphenyl-3-yl)boronic acid

This product was prepared by a Method analogous to that as described above for Preparation 63 using 2-(4'-ethylsulfonyl-6-fluorobiphenyl-3-yl)-2,3-dihydro-1H-1,3-diaza-2-boraphenalene (Preparation 64) to afford the title compound as a colourless oil in 88% yield, 378 mg.

$^1$H NMR (400 MHz, DMSO-$d_6$): δ ppm 1.39 (t, 3H), 3.35 (q, 2H), 7.33 (dd, 1H), 7.83-7.88 (m, 3H), 7.98-8.03 (m, 3H), 8.23 (s, 2H).

LCMS (System 9): Rt=3.04 minutes MS m/z 309 [M+H]$^+$

Preparation 66

5-Chloro-4'-(ethylsulfonyl)-2'-methoxy-[1,1'-biphenyl]-2-carbonitrile

To a solution of 2-(4-(ethylsulfonyl)-2-methoxyphenyl)-4,4,5,5-tetramethyl-1,3,2-dioxaborolane (Preparation 21, 542 mg, 1.66 mmol) in dioxane (10 mL) and water (2 mL) was added 2-bromo-4-chlorobenzonitrile (300 mg, 1.38 mmol), and sodium carbonate (441 mg, 4.16 mmol). The reaction was degassed and then tetrakis(triphenylphosphine)palladium(0) (160 mg, 0.14 mmol) was added and the reaction mixture further degassed. The reaction was on a preheated hot plate (110° C.) for 16 hours. The reaction mixture was cooled to room temperature and filtered through celite and the solvent removed in vacuo. The crude material was purified by silica gel column chromatography eluting with EtOAc:cyclohexane 1:1 to give the title compound as a dark solid in 62% yield, 0.345 g.

$^1$H NMR (400 MHz, $CDCl_3$): δ ppm 1.35 (t, 3H), 3.16 (q, 2H), 3.92 (s, 3H), 7.40-7.53 (m, 4H), 7.59-7.62 (dd, 1H) 7.70 (d, 1H).

LCMS (System 11): Rt=2.62 minutes MS m/z no ionisation.

Preparation 67

(6-Cyano-4'-(ethylsulfonyl)-2'-methoxy-[1,1-biphenyl]-3-yl)boronic acid

To a solution of 5-chloro-4'-(ethylsulfonyl)-2'-methoxy-[1,1'-biphenyl]-2-carbonitrile (Preparation 66, 330 mg, 0.985 mmol) in dioxane (5 mL) was added bis(diphenylphosphino) ferrocene-palladium(II)dichloride (30 mg, 0.12 mmol), potassium acetate (290 mg, 2.95 mmol) and bis(pinacolato)diboron (3.75 mg, 1.48 mmol). The reaction was degassed and then placed on a preheated hot plate (100° C.) for 16 hours. The reaction mixture was cooled to room temperature, filtered through celite and the solvent removed in vacuo. The crude material was purified by reverse phase column chromatography eluting with MeCN/$H_2O$ to hydrolyse the boronic ester to afford the title compound in 25% yield, 85 mg.

$^1$H NMR (400 MHz, $CDCl_3$): δ ppm 1.36 (t, 3H), 1.38 (q, 2H), 3.87 (s, 3H), 7.39-7.59 (m, 4H), 7.81-8.06 (m, 2H).

LCMS (System 11): Rt=2.20 minutes MS m/z no ionisation.

Preparation 68

5'-Chloro-4-(ethylsulfonyl)-2-fluoro-2'-methoxy-1,1'-biphenyl

To a solution of (5-chloro-2-methoxyphenyl)boronic acid (714 mg, 1.68 mmol) in dioxane (5 mL) and water (1 mL) was added 1-bromo-4-(ethylsulfonyl)-2-fluorobenzene (Preparation 19, 450 mg, 1.68 mmol), and sodium carbonate (534 mg, 5.04 mmol). The reaction was degassed and then tetrakis(triphenylphosphine) palladium(0) (194 mg, 0.17 mmol) was added and the reaction mixture further degassed. The reaction was placed on a preheated hot plate (110° C.) for 16 hours. The reaction mixture was cooled to room temperature and filtered through celite and the solvent removed in vacuo. The crude material was purified by silica gel column chromatography eluting with EtOAc:cyclohexane 40:60 to give the title compound as a brown oil in 90% yield, 500 mg.

$^1$H NMR (400 MHz, $CDCl_3$): δ ppm 1.35 (t, 3H), 3.18 (q, 2H), 3.80 (s, 3H), 6.94 (d, 1H), 7.25 (d, 1H), 7.38 (d, 1H), 7.53-7.56 (m, 1H), 7.66 (d, 1H), 7.74 (d, 1H).

$^{19}$F NMR (376 MHz, $CDCl_3$): δ −109.69 ppm

LCMS (System 13): Rt=2.60 minutes MS m/z no ionisation.

Preparation 69

2-(4'-(Ethylsulfonyl)-2'-fluoro-6-methoxy-[1,1'-biphenyl]-3-yl)-4,4,5,5-tetramethyl-1,3,2-dioxaborolane To a solution of 5'-chloro-4-(ethylsulfonyl)-2-fluoro-2'-methoxy-1,1'-biphenyl (Preparation 68, 500 mg, 1.52 mmol) in 1,2-dimethoxyethane (7 mL) was added potassium acetate (448 mg, 4.56 mmol), bis(pinacolato)diboron (425 mg, 1.68 mmol), tricyclohexylphosphine (46.2 mg, 0.18 mmol) and tris(dibenzylideneacetone) dipalladium(0) (69.6 mg, 0.076 mmol). The reaction mixture was degassed and then refluxed at 85° C. for 16 hours. The reaction mixture was cooled to room temperature and filtered through a pad of celite. The filtrate was diluted with EtOAc (50 mL) and washed with water (50 mL) then dried over $MgSO_4$, filtered and the solvent removed in vacuo. The crude material was purified by reverse phase chromatography (MeCN/water, 0.1% formic acid, gradient) and flash chromatography (EtOAc:heptanes 40:60) to give the title product as a white foam in 15% yield, 85 mg.

$^1$H NMR (400 MHz, $CDCl_3$): δ 1.31-1.35 (m, 15H), 3.17 (q, 2H), 3.84 (s, 3H), 7.00 (d, 1H), 7.55-7.59 (m, 1H), 7.64 (d, 1H), 7.69-7.72 (m, 2H), 7.88 (d, 1H) ppm.

19F NMR (376 MHz, CDCl₃): δ −109.53 ppm.

Preparation 70

2-Bromo-1-fluoro-4-((4-methoxybenzyl)oxy)benzene

To a solution of 3-bromo-4-fluorophenol (2.18 g, 11.4 mmol) in DMF (15 mL) was added potassium carbonate (3.15 g, 22.8 mmol) portion wise at room temperature. The mixture was stirred at room temperature for 10 minutes then 4-methoxybenzyl chloride (1.55 mL, 11.4 mmol) was added drop wise. On completion of the addition the reaction was heated at 60° C. under nitrogen for 15 hours. The cooled reaction mixture was quenched with water (50 mL) and extracted with EtOAc (3×50 mL). The combined extracts were washed with 1M aqueous NaOH solution (50 mL) and brine (50 mL), then dried over anhydrous MgSO₄, filtered and concentrated in vacuo to afford the crude title compound as an off-white solid in quantitative yield, 3.62 g.

¹H NMR (400 MHz, CDCl₃): δ ppm 3.82 (s, 3H), 4.93 (s, 2H), 6.83-6.87 (m, 1H), 6.91 (dt, 2H), 7.02 (dd, 1H), 7.14 (dd, 1H), 7.34 (m, 2H).

LC (System 11): Rt=2.99 minutes

Preparation 71

2-(2-Fluoro-5-((4-methoxybenzyl)oxy)phenyl)-4,4,5,5-tetramethyl-1,3,2-dioxaborolane To a solution of 2-bromo-1-fluoro-4-((4-methoxybenzyl)oxy)benzene (Preparation 70, 3.55 g, 11.4 mmol) in dimethoxyethane (15 mL) was added bis(pinacolato)diboron (3.19 g, 12.6 mmol) and potassium acetate (1.68 g, 17.1 mmol) at room temperature. The mixture was degassed and purged with nitrogen gas 3 times, then tris(dibenzylideneacetone)dipalladium(0) (313 mg, 0.34 mmol) and tricyclohexylphosphine (384 mg, 1.37 mmol) were added. The mixture was degassed and purged with nitrogen gas then heated at reflux for 15 hours. The cooled reaction mixture was diluted with EtOAc (50 mL) and filtered through arbocel to remove catalyst traces, washing through with fresh EtOAc (2×25 mL). The filtrate was washed with water (20 mL) and brine (20 mL), then dried over anhydrous MgSO₄, filtered and concentrated in vacuo to afford the crude. Purification by column chromatography eluting with (heptanes:EtOAc 95:5 to 90:10) gave the title compound as a yellow fluffy solid in 65% yield, 2.65 g.

¹H NMR (400 MHz, CDCl₃): δ ppm 1.36 (s, 12H) 3.82 (s, 3H), 4.96 (s, 2H), 6.89-6.93 (m, 3H), 6.95 (d, 1H), 6.98 (dd, 1H), 7.31 (dd, 1H), 7.33-7.36 (m, 1H).

LC (System 13): Rt=2.90 minutes

Preparation 72

2-Bromo-5-(chlorosulfonyl)benzoic acid

To chlorosulfonic acid (100 mL) cooled to 0° C. was added 2-bromobenzoic acid (20.0 g, 99.5 mmol) portionwise over 10 minutes. The reaction mixture was warmed to room temperature and then to reflux cautiously over 30 minutes in 10° C. increments, followed by reflux for 16 hours. After cooling to room temperature the solution was quenched in 1 mL portions into ice-water (2 L). Further ice was added as necessary to keep the temperature below 5° C. The resulting precipitate was filtered under vacuum and dried in a vacuum oven for 4 hours to give the title compound as a tan solid in 95% yield, 28.6 g.

¹H-NMR (400 MHz, CDCl₃): δ ppm 8.00 (s, 2H), 8.60 (s, 1H).

LCMS (System 13): Rt=2.07 minutes

Preparation 73

2-Bromo-5-(ethylsulfonyl)benzoic acid

To 2-bromo-5-(chlorosulfonyl)benzoic acid (Preparation 72, 10.1 g, 33.8 mmol) dissolved in THF (100 mL) was added hydrazine monohydrate (3.32 mL, 67.6 mmol) cautiously at 0° C. under nitrogen. A fine precipitate formed, the reaction was allowed to warm to room temperature over 126 hours before filtering. The solid was washed with heptanes, dried under reduced pressure and dissolved in industrial methylated spirit (100 mL). To this solution was added sodium acetate (16.6 g, 203 mmol) and ethyl iodide (13.5 mL, 169 mmol) and the reaction heated to reflux for 20 hours. After cooling to room temperature, the solvent was removed under reduced pressure and the residue partitioned between EtOAc (500 mL) and sodium hydroxide solution (1M, 500 mL). The layers were separated and the organic layer discarded. The aqueous layer was acidified to pH=1 with HCl (1M, 500 mL) and extracted with EtOAc (5×500 mL). The combined organic layers were dried over MgSO₄ and the solvent removed under reduced pressure to give the title compound as a tan solid in 48% yield, 4.82 g.

¹H-NMR (400 MHz, CDCl₃): δ ppm 1.20 (t, 3H), 3.10 (q, 2H), 7.80 (d, 1H), 7.85 (d, 1H), 8.40 (s, 1H).

LCMS (System 12): Rt=1.90 minutes MS m/z 293 [M⁸¹Br−H]⁻

Preparation 74

2-Bromo-5-(ethylsulfonyl)benzamide

To 2-bromo-5-(ethylsulfonyl)benzoic acid (Preparation 73, 8.10 g, 27.6 mmol) dissolved in THF (200 mL) was added carbonyldiimidazole (8.72 g, 41.4 mmol). The reaction was left to stir for 5 minutes under nitrogen before ammonia was bubbled through the solution. A temperature rise from 22° C. to 41° C. was observed over 10 minutes. The temperature then started to fall, reaching 35° C. after 5 minutes, after which the flow of ammonia was stopped. The reaction mixture was left to stand as a saturated ammonia solution for 30 minutes before removal of the solvent under reduced pressure. The residue was partitioned between EtOAc (500 mL) and water (500 mL) and the layers separated. The organic layer was dried over MgSO₄ and the solvent removed under reduced pressure to give the crude product. Trituration with CH₂Cl₂ gave the title compound as a solid in 28% yield, 2.23 g. A further portion of the title compound was isolated by drying of the filtrate and further trituration, to give a further 8%, 650 mg.

¹H NMR (400 MHz, DMSO-d₆): δ ppm 1.10 (t, 3H), 3.40 (q, 2H), 7.75-7.85 (m, 3H), 8.00 (d, 1H), 8.10 (s, 1H).

LCMS (System 11): Rt=1.80 minutes MS m/z 292 [M⁷⁹Br+H]⁺

Preparation 75

2-Bromo-5-(ethylsulfonyl)benzonitrile

To 2-bromo-5-(ethylsulfonyl)benzamide (Preparation 74, 2.20 g, 7.53 mmol) in THF (50 mL) with triethylamine (1.57 mL, 11.3 mmol) was added trifluoroacetic anhydride (1.26 mg, 9.04 mmol) dropwise under nitrogen. The reaction was left to stir for 16 hours, before dilution with EtOAc (100 mL) and washing with sodium bicarbonate solution (saturated 100 mL), HCl (1M, 100 mL) and brine (100 mL). The organic phase was dried over MgSO$_4$ and the solvent removed under reduced pressure to give the title compound as a colourless solid in 80% yield, 1.64 g.

$^1$H NMR (400 MHz, CDCl$_3$): δ 1.30 (t, 3H), 3.15 (q, 2H), 7.90-8.00 (m, 2H), 8.20 (s, 1H) ppm.

LCMS (System 11): Rt=2.29 minutes MS m/z no ionization.

Preparation 76

4-(Ethylsulfonyl)-2'-fluoro-5'-((4-methoxybenzyl)oxy)-[1,1'-biphenyl]-2-carbonitrile To 2-bromo-5-(ethylsulfonyl)benzonitrile (Preparation 75, 1.09 g, 3.96 mmol) in dioxane/water (5:1 v/v, 66 mL) was added 2-(2-fluoro-5-((4-methoxybenzyl)oxy)phenyl)-4,4,5,5-tetramethyl-1,3,2-dioxaborolane (Preparation 71, 1.56 g, 4.35 mmol) and sodium carbonate (1.26 g, 11.9 mmol). The reaction mixture was degassed and tetrakis(triphenylphosphine) palladium(0) (462 mg, 0.40 mmol) was added, and the reaction heated to 110° C. under nitrogen for 12 hours. After cooling to room temperature, silica gel was added, and the solvent removed under reduced pressure. The residue was purified using silica gel column chromatography eluting with EtOAc/cyclohexane 1:3 followed by reverse phase column chromatography eluting with MeCN/water, with 0.1% NH3 0-100% to afford the title compound as a solid in 51% yield, 851 mg.

$^1$H NMR (400 MHz, CDCl$_3$): δ ppm 1.40 (t, 3H), 3.20 (q, 2H), 3.80 (s, 3H), 5.00 (s, 2H), 6.50 (d, 2H), 7.00 (m, 1H), 7.10 (m, 1H), 7.20 (t, 1H), 7.35-7.40 (m, 2H), 7.70 (d, 1H), 8.20 (d, 1H), 8.30 (s, 1H).

LC (System 12): Rt=3.08 minutes

Preparation 77

4-(Ethylsulfonyl)-2'-fluoro-F-hydroxy-[1,1'-biphenyl]-2-carbonitrile

To 4-(ethylsulfonyl)-2'-fluoro-5'-((4-methoxybenzyl)oxy)-[1,1'-biphenyl]-2-carbonitrile (Preparation 76, 850 mg, 1.99 mmol) dissolved in CH$_2$Cl$_2$ (6 mL) at 0° C. under nitrogen, was added trifluoroacetic acid (2 mL) dropwise. On addition the reaction turned purple. After stirring for 20 minutes at 0° C. the solvent was removed under reduced pressure to give a brown solid. Trituration with CH$_2$Cl$_2$ gave the title compound as a colourless solid in 53% yield, 325 mg. Drying of the filtrate under reduced pressure, followed by further trituration gave a second batch of material in 46% yield, 279 mg.

$^1$H NMR (400 MHz, CD$_3$OD): δ ppm 1.30 (t, 3H), 3.30 (q, 2H), 6.60 (m, 1H), 6.95 (m, 1H), 7.10 (t, 1H), 7.80 (d, 1H), 8.20 (d, 1H), 8.40 (s, 1H).

LCMS (System 12): Rt=2.39 minutes MS m/z 304 [M−H]$^-$

Preparation 78

2'-Cyano-4'-(ethylsulfonyl)-6-fluoro-[1,1'-biphenyl]-3-yl trifluoromethanesulfonate To 4-(ethylsulfonyl)-2'-fluoro-5'-hydroxy-[1,1'-biphenyl]-2-carbonitrile (Preparation 77, 600 mg, 1.96 mmol) in CH$_2$Cl$_2$ (20 mL) cooled to 0° C. under nitrogen, was added triflic anhydride (496 μL, 2.95 mmol) dropwise. The reaction was allowed to warm to room temperature over 1 hour and then stirred for 16 hours at room temperature before dilution with CH$_2$Cl$_2$ (80 mL) and washing with sodium bicarbonate solution (saturated, 50 mL) and NH$_4$Cl solution (saturated, 50 mL). The organic phase was dried over MgSO$_4$ and the solvent removed under reduced pressure. The residue was purified using silica gel column chromatography eluting with EtOAc:cyclohexane 1:4 to 2:3 to afford the title compound in 82% yield, 707 mg.

$^1$H NMR (400 MHz, CDCl$_3$): δ ppm 1.40 (t, 3H), 3.20 (q, 2H), 7.35-7.40 (m, 2H), 7.40 (m, 1H), 7.80 (d, 1H), 8.20 (d, 1H), 8.40 (s, 1H).

LCMS (System 12): Rt=3.06 minutes Ms m/z no ionization.

Preparation 79

4-(Ethylsulfonyl)-2'-fluoro-5'-(4,4,5,5-tetramethyl-1,3,2-dioxaborolan-2-yl)-[1,1'-biphenyl]-2-carbonitrile To 2'-cyano-4'-(ethylsulfonyl)-6-fluoro-[1,1'-biphenyl]-3-yl trifluoromethanesulfonate (Preparation 78, 350 mg, 0.80 mmol) in dioxane (7 mL) was added potassium acetate (236 mg, 2.4 mmol) and bis(pinacolato)diboron (224 mg, 0.88 mmol). The reaction mixture was degassed and dichloro[1,1'-bis(diphenylphosphino)ferrocene]palladium(II)acetone adduct (65 mg, 0.08 mmol) was added, before heating to 110° C. under nitrogen for 16 hours. After cooling to room temperature the reaction was filtered through celite and purified by silica gel column chromatography eluting with EtOAc: heptane 1:4 to 1:1 to give a 3:1 mixture of starting material to product. The crude material was dissolved in dioxane (7 mL) and potassium acetate (236 mg, 2.4 mmol) was added followed by bis(pinacolato)diboron (224 mg, 0.88 mmol). The reaction mixture was degassed and dichloro[1,1'-bis(diphenylphosphino)ferrocene]palladium(II)acetone adduct (65 mg, 0.08 mmol) added, before heating to 110° C. under nitrogen for 3 hours. After cooling to room temperature the reaction mixture was filtered through celite and purified using silica gel column chromatography eluting with EtOAc:heptanes 7:93 to 60:40 to give the title compound in 77% yield, 257 mg.

$^1$H-NMR (400 MHz, CDCl$_3$): δ ppm 1.20 (s, 12H), 1.30 (t, 3H), 3.20 (q, 2H), 7.20 (t, 1H), 7.70 (s, 1H), 7.90 (d, 1H), 7.95 (d, 1H), 8.15 (d, 1H), 8.30 (s, 1H).

LCMS (System 12): Rt=3.29 minutes MS m/z no ionization.

Preparation 80

4-(4,4,5,5-Tetramethyl-1,3,2-dioxaborolan-2-yl)benzenesulfonamide

To a solution of 4-bromobenzenesulfonamide (2.00 g, 9.32 mmol) and bis(pinacolato) diboron (2.40 g, 9.32 mmol) in DMSO (20 mL) was added potassium acetate (2.5 g, 24.4 mmol) and the mixture was degassed for 45 minutes. [1,1'-bis(diphenylphosphino)ferrocene]dichloropalladium(II) (220 mg, 0.26 mmol) was then added and the mixture heated to 90° C. for 16 hours. Once cooled the reaction mixture was diluted with EtOAc (30 mL), washed with water (3×30 mL), dried over MgSO$_4$ and concentrated under vacuum. The residue was triturated from Et$_2$O (50 mL) and HCl (1M, 50 mL) the solid formed was dissolved in CH$_2$Cl$_2$ (30 mL) and filtered through a pad of silica washing with Et$_2$O then concentrated to give the title compound as an off white solid 13% yield, 550 mg.

$^1$H NMR (400 MHz, CDCl$_3$): δ ppm 1.36 (s, 12H), 4.87 (s, 2H), 7.89-7.95 (m, 4H).
LCMS (System 11): Rt=2.30 minutes MS m/z 282 [M−H]$^−$ Preparation 81

2-(3-Chloro-4-fluorophenyl)-2,3-dihydro-1H-1,3-diaza-2-boraphenalene

A solution of 3-chloro-4-fluorobenzene boronic acid (4 g, 22.8 mmol) and naphthalene-1,8-diamine (3.62 g, 22.9 mol) in anhydrous toluene (80 mL) was heated to reflux for 4 hours. The reaction mixture was cooled to room temperature, then concentrated in vacuo. The residue was triturated with hexane to afford the title compound as a grey solid in 88% yield, 6 g.
$^1$H NMR (400 MHz, CDCl$_3$): δ ppm 5.93 (s, 2H), 6.41 (d, 2H), 7.06 (d, 2H), 7.11-7.16 (m, 2H), 7.19 (t, 1H), 7.47-7.51 (m, 1H), 7.64-7.66 (m, 1H).

Preparation 82

5'-Chloro-4-(ethylsulfonyl)-2,2'-difluoro-1,1-biphenyl

A solution of 2-(4-(ethylsulfonyl)-2-fluorophenyl)-4,4,5,5-tetramethyl-1,3,2-dioxaborolane (Preparation 45, 1.77 g, 5.64 mmol), 4-chloro-1-fluoro-2-iodobenzene (1.28 g, 5.00 mmol), and sodium carbonate (1.59 g, 15.00 mmol) in dioxane (40 mL) and water (10 mL) was degassed. Tetrakis(triphenylphosphine)palladium(0) (577 mg, 0.50 mmol) was added and the mixture was degassed twice more, and the reaction warmed to 80° C. for 2 hours. The reaction was cooled and diluted with EtOAc (50 mL) and water (50 mL), the layers separated and the aqueous extracted with EtOAc (2×30 mL). The combined organic layers were washed with brine (30 mL), dried over MgSO$_4$ and the solvent removed in vacuo. The crude was purified by silica gel column chromatography eluting with EtOAc:heptane 1:19 to 1:1 to give the title compound as a colourless oil 28% yield, 443 mg.
$^1$H NMR (400 MHz, CDCl$_3$): δ ppm 1.34 (t, 3H), 3.18 (q, 2H), 7.16 (m, 1H), 7.38 (m, 2H), 7.60 (m, 1H), 7.73 (m, 1H), 7.78 (m, 1H).
$^{19}$F NMR (376 MHz, CDCl$_3$): δ −110.2 (m, 1F), −116.9 (m, 1F).
LCMS (System 13): Rt=3.17 minutes MS m/z no ionisation.

Preparation 83

2-(4'-(Ethylsulfonyl)-2',6-difluoro-[1,1'-biphenyl]-3-yl)-4,4,5,5-tetramethyl-1,3,2-dioxaborolane A solution of 5'-chloro-4-(ethylsulfonyl)-2,2'-difluoro-1,1'-biphenyl (Preparation 82, 100 mg, 0.32 mmol), bis(pinacolato)diboron (241 mg, 0.949 mmol), palladium(II)acetate (2.0 mg, 0.01 mmol), 2-dicyclohexylphosphino-2',4',6'-triisopropylbiphenyl (9.0 mg, 0.190 mmol) and potassium acetate (93 mg, 0.95 mmol) in dioxane (4 mL) was warmed to 110° C. in a sealed tube. After 2 hours the reaction was charged with further palladium(II)acetate (10 mg, 0.044 mmol) and 2-dicyclohexylphosphino-2',4',6'-triisopropylbiphenyl (20 mg, 0.042 mmol) and the reaction stirred for 18 hours at 110° C. The reaction was cooled, filtered through a plug of celite washing with EtOAc (20 mL). The volatiles were removed in vacuo. The crude material was used without further purification, assumed 100% conversion (128 mg).

LCMS (System 13): Rt=3.54 minutes MS m/z no ionisation.

Preparation 84

4-(3-Bromo-4-fluorophenyl)-7-cyclopropyl-7H-imidazo[4,5-c]pyridazine

This was prepared by a Method analogous to that as described above for Preparation 87 using 7-cyclopropyl-4-(4-fluorophenyl)-7H-imidazo[4,5-c]pyridazine (Preparation 93, 450 mg, 1.77 mmol) and 1,3-dibromo-5,5-dimethylhydantoin (253.3 mg, 0.885 mmol) to afford the title compound as a white solid in 25% yield, 500 mg.
$^1$H-NMR (400 MHz, DMSO-d$_6$): δ ppm 1.18-1.24 (m, 4H), 3.77-3.78 (m, 1H), 7.63 (t, 1H), 8.45-8.51 (m, 1H), 8.82-8.85 (m, 2H), 9.58 (s, 1H).
LCMS (System 7): Rt=3.10 minutes MS m/z 333 [M+H]$^+$ Preparation 85

1-Bromo-4-(ethylthio)-2-chlorobenzene

To a room temperature solution of 1-bromo-4-fluoro-2-chlorobenzene (1.9 g, 0.97 mmol) in DMSO (10 mL) was added sodium ethanethiolate (0.84 g, 1 mmol) and the resulting reaction mixture was heated to 100° C. for 18 hours. The reaction mixture was partitioned between water (20 mL) and EtOAc (50 mL). The organic layer was separated and the aqueous layer was further extracted with EtOAc (3×50 mL). The organic layers were combined and washed with saturated brine solution (20 mL) then dried over Na$_2$SO$_4$, filtered and concentrated in vacuo. The crude material was purified by silica gel column chromatography eluting with heptane to afford the title compound as a colourless liquid in 70% yield, 1.6 g.
$^1$H NMR (400 MHz, CDCl$_3$): δ ppm 1.31 (s, 3H), 2.95 (q, 2H), 7.04 (d, 1H), 7.38 (s, 1H), 7.50 (d, 1H).
LC (System 1): Rt=3.65 minutes Preparation 86

4-(4-Fluorophenyl)-7-isopropyl-7H-imidazo[4,5-c]pyridazine

A suspension of 4-chloro-7-isopropyl-7H-imidazo[4,5-c]pyridazine (Preparation 6, 575 mg, 2.92 mmol), (4-fluorophenyl)boronic acid (534 mg, 3.81 mmol), cesium carbonate (1.66 g, 5.08 mmol) in water (2 mL) and dioxane (10 mL) were degassed with nitrogen for 30 minutes.
Tetrakis(triphenylphosphine)palladium(0) (293 mg, 0.254 mmol) was added and the reaction heated to 100° C. and stirred for 5 hours. The reaction was cooled to room temperature, filtered through celite and washed with EtOAc (5 mL). The filtrate was partitioned with water (20 mL) and the product extracted with EtOAc (2×10 mL), dried over Na$_2$SO$_4$, filtered and concentrated under vacuum. Purification by silica gel column chromatography eluting with EtOAc/heptanes, 7/3 afforded the title compound as a pale yellow oil in 100% yield 751 mg.
$^1$H NMR (400 MHz, CDCl$_3$): δ ppm 1.79 (d, 6H), 5.21 (m, 1H), 7.48 (m, 1H), 7.55 (m, 1H), 8.22 (m, 2H), 8.39 (s, 1H), 9.39 (s, 1H).

LCMS (System 12): Rt=2.27 minutes MS m/z 257 [M+H]⁺

Preparation 87

4-(3-Bromo-4-fluorophenyl)-7-isopropyl-7H-imidazo[4,5-c]pyridazine

To a solution of 4-(4-fluorophenyl)-7-isopropyl-7H-imidazo[4,5-c]pyridazine (Preparation 86, 770 mg, 3.00 mmol) in concentrated sulfuric acid (7.00 mL) at 0° C. was added 1,3-dibromo-5,5-dimethyl hydantoin (687 mg, 2.40 mmol) portionwise over 1.5 hours and the reaction stirred at 0° C. for 1 hour. The reaction mixture was added dropwise into a solution of saturated aqueous sodium thiosulfate solution (20 mL) at 0° C. Following complete addition the reaction mixture was basified to pH=9 with solid potassium carbonate. The reaction mixture was filtered through celite, washed with $CH_2Cl_2$ (20 mL) and extracted into $CH_2Cl_2$ (3×40 mL), dried over $Na_2SO_4$, filtered and concentrated under vacuum to yield a pale yellow solid. Purification by silica gel column chromatography eluting with $EtOAc:CH_2Cl_2$ 1:1 afforded the title compound as a pale yellow solid (558 mg, 55%).

$^1$H NMR (400 MHz, CDCl$_3$): δ ppm 1.79 (d, 6H), 5.22 (m, 1H), 7.38 (t, 1H), 8.20 (m, 1H), 8.40 (s, 1H), 8.56 (d, 1H), 9.39 (s, 1H).
LCMS (System 12): Rt=2.65 minutes MS m/z 337 [M$^{81}$Br+H]⁺

Preparation 88

5-Bromo-4'-(ethylsulfonyl)-2'-methoxy-[1,1'-biphenyl]-2-ol

To a stirred solution of 2-(4-(ethylsulfonyl)-2-methoxyphenyl)-4,4,5,5-tetramethyl-1,3,2-dioxaborolane (Preparation 21, 600 mg, 1.84 mmol) in dioxane (30 mL) and water (10 mL) were added 4-bromo-2-iodophenol (604 mg, 2.02 mmol), sodium carbonate (488 mg, 4.6 mmol) and tetrakis(triphenylphosphine)palladium(0) (106 mg, 0.092 mmol). The reaction was stirred at reflux for 18 hours. The reaction was allowed to cool temperature and then filtered through celite. The filtrate was reduced to dryness and then purified by silica gel column chromatography eluting with cyclohexane:EtOAc 1:1 followed by a second silica gel column chromatography eluting with $CH_2Cl_2$:MeOH 98:2 to give the title compound as pale yellow solid in 44% yield, 301 mg.

$^1$H NMR (400 MHz CDCl$_3$): δ ppm 1.33 (t, 3H), 3.18 (q, 2H), 3.99 (s, 3H), 5.82 (s, 1H), 6.91 (d, 1H), 7.32 (d, 1H), 7.43 (dd, 1H), 7.51 (d, 1H), 7.55 (d, 1H), 7.64 (dd, 1H).
LCMS: (System 11): Rt=2.55 minutes MS m/z 371 [M$^{79}$Br+H]⁺

Preparation 89

4'-(Ethylsulfonyl)-2'-methoxy-5-(4,4,5,5-tetramethyl-1,3,2-dioxaborolan-2-yl)-[1,1'-biphenyl]-2-ol To a solution of 5-bromo-4'-(ethylsulfonyl)-2'-methoxy-[1,1'-biphenyl]-2-ol (Preparation 88, 150 mg, 0.40 mmol) in dioxane (15 mL) was added potassium acetate (159 mg, 1.62 mmol) and bis(pinacolato)diboron (153 mg, 0.61 mmol) (and the suspension degassed under nitrogen. 1,1'-bis(diphenylphosphino)ferrocene-palladium(II)dichloride (33 mg, 0.04 mmol) was added and the reaction mixture stirred at 90° C. for 4 hours. The reaction was allowed to cool to room temperature and then filtered through celite, the celite pad washed with EtOAc and the filtrate reduced to dryness to give the title compound which was used without further purification (235 mg).

$^1$H NMR (400 MHz CDCl$_3$): δ ppm 1.32-1.34 (m, 15H), 3.17 (q, 2H), 3.97 (s, 3H), 7.03 (d, 1H), 7.56 (d, 1H), 7.62 (d, 1H), 7.68 (d, 1H), 7.80 (dd, 1H).
LC (System 10): Rt=2.64 minutes Preparation 90

5-Chloro-N$^3$-cyclopropylpyridazine-3,4-diamine 3,5-Dichloro-4-aminopyridazine (5.12 g, 31.2 mmol) was added to cyclopropylamine (37.0 g, 650 mmol) in a stainless steel sealed container (100 mL capacity), to give a homogenous solution. The mixture was heated for 12 hours at 120° C. The reaction mixture was cooled to room temperature then evaporated in vacuo. The residue was dissolved in EtOAc (150 mL) with sonication and stirring. The EtOAc solution was washed with 10% aqueous potassium carbonate solution (2×200 mL), dried over anhydrous MgSO$_4$, then filtered and evaporated in vacuo. The mixture was redissolved in $CH_2Cl_2$ and purified using silica gel column chromatography eluting with $CH_2Cl_2$ (100 mL), then EtOAc (150 mL) to give the title compound as a light orange solid in 73% yield, 4.2 g.

$^1$H NMR (400 MHz, DMSO-d$_6$): δ ppm 0.2-0.5 (m, 2H), 0.38-0.40 (m, 2H), 2.85-2.95 (m, 1H), 5.75 (b s, 2H), 6.0-6.05 (b s, 1H), 7.80 (s, 1H).

Preparation 91

4-Chloro-7-cyclopropyl-7H-imidazo[4,5-c]pyridazine

A mixture of 5-chloro-N-3-cyclopropylpyridazine-3,4-diamine (Preparation 90, 10.0 g, 54 mmol) and triethylorthoformate (120 mL) were heated to reflux for 3 hours. The reaction mixture was concentrated in vacuo and the residue was purified by silica gel column chromatography eluting with $CH_2Cl_2$:MeOH 98:2 to afford the title compound as a brown solid in 48% yield, 5 g.

$^1$H NMR (400 MHz, DMSO-d$_6$): δ ppm 1.05-1.30 (m, 4H), 3.75-3.85 (m, 1H), 8.88 (s, 1H), 9.26 (s, 1H.
LCMS (System 7): Rt=1.69 minutes MS m/z 195 [M+H]⁺

Preparation 92

4-(3-iodo-4-fluorophenyl)-7-cyclopropyl-7H-imidazo[4,5-c]pyridazine

Prepared according to the method described for Preparation 93 using 4-chloro-7-cyclopropyl-7H-imidazo[4,5-c]-pyridazine (Preparation 91) and 3-chloro-4-fluorobenzeneboronic acid.

$^1$H-NMR (400 MHz, CDCl$_3$): δ ppm 1.25-1.36 (m, 4H), 3.69-3.73 (m, 1H), 7.34 (t, 1H), 8.08-8.12 (m, 1H), 8.27 (s, 1H), 8.31-8.34 (m, 1H), 9.33 (s, 1H).

Preparation 93

7-Cyclopropyl-4-(4-fluorophenyl)-7H-imidazo[4,5-c]pyridazine

To a room temperature solution of 4-chloro-7-cyclopropyl-7H-imidazo[4,5-c]pyridazine (Preparation 91, 1.00 g, 5.1 mmol) in dioxane (20 mL) was added 4-fluorobenzene boronic acid (1.08 g, 7.71 mmol) and solution of $Na_2CO_3$ (2.72 g, 25.7 mmol in 12.8 mL water). The reaction mixture was degassed.

Tetrakis(triphenylphosphine)palladium(0) (297 mg, 0.26 mmol) was then added and the mixture was heated to reflux for 16 hours. The solvent was removed in vacuo and the water layer was filtered. The residue was purified by silica gel column Chromatography eluting with EtOAc to afford the title compound as a red solid in 73% yield, 949 mg.

$^1$H-NMR (400 MHz, $CDCl_3$): δ ppm 1.25-1.37 (m, 4H), 3.69-3.73 (m, 1H), 7.24-7.28 (m, 2H), 8.19-8.23 (m, 2H), 8.25 (s, 1H), 9.36 (s, 1H).

LCMS (System 4): Rt=1.03 minutes MS m/z 255 [M+H]$^+$

Preparation 94

4-(3-Iodo-4-fluorophenyl)-7-cyclopropyl-7H-imidazo[4,5-c]pyridazine

Prepared by a Method analogous to that as described above for Preparation 87 using 7-cyclopropyl-4-(4-fluorophenyl)-7H-imidazo[4,5-c]pyridazine (Preparation 93) and 1,3-diiodo-5,5-dimethylhydantoin to afford the title compound in 79% yield.

$^1$H-NMR (400 MHz, $CDCl_3$): δ ppm 1.24-1.37 (m, 4H), 3.68-3.74 (m, 1H), 7.23-7.27 (m, 1H), 8.17-8.21 (m, 1H), 8.26 (s, 1H), 8.62 (dd, 1H), 9.32 (s, 1H).

LCMS (System 3): Rt=1.45 minutes MS m/z 381 [M+H]$^+$

Preparation 95

7-Ethyl-4-[4-fluoro-3-(4,4,5,5-tetramethyl-[1,3,2]dioxaborolan-2-yl)phenyl]-7H-imidazo[4,5-c]pyridazine A mixture of 4-(3-bromo-4-fluorophenyl)-7-ethyl-7H-imidazo[4,5-c]pyridazine (Preparation 11, 50 mg, 0.16 mmol), 4,4,5,5,4',4',5',5'-octamethyl-[2,2']bi[[1,3,2]dioxaborolanyl] (59 mg, 0.23 mmol), 1,1'-bis(diphenylphosphino) ferrocene palladium dichloride (13 mg, 0.016 mmol) and potassium acetate (46 mg, 0.47 mmol) in anhydrous dioxane (2.0 mL), under a nitrogen atmosphere, was heated at 100° C. for 3 hours. After cooling to room temperature, the mixture was filtered through celite and the filtrate was partitioned into $CH_2Cl_2$ (10 mL) and water (10 mL). The organic layers were extracted with $CH_2Cl_2$ (2×10 mL), dried over anhydrous $MgSO_4$, filtered and evaporated in vacuo. The crude product was purified by silica gel column chromatography eluting with EtOAc:MeOH 10:1 to afford the title compound as a gum in 74% yield, 42.5 mg.

$^1$H-NMR (400 MHz, $CDCl_3$): δ ppm 1.38 (s, 12H), 1.68 (t, 3H), 4.57 (q, 2H), 7.20-7.29 (m, 1H), 8.19-8.24 (m, 1H), 8.28 (s, 1H), 8.41-8.47 (m, 1H), 9.39 (s, 1H), LCMS (System 6): Rt=1.50 minutes MS m/z=369 [M+H]$^+$ Preparation 96

N-(3,5-Dichloropyridazin-4-yl)-N'-(1-methylcyclopropyl)imidoformamide

To an ice cooled stirred solution of 1-methylcyclopropylamine hydrochloride salt (2 g, 18.6 mmol) in anhydrous THF (15 mL) was added sodium hydride (60 wt % dispersion in oil, 1.48 g, 37.2 mmol) at 0° C., the reaction was then stirred at room temperature for 1 hour. The resulting suspension was added to a solution of ethyl (3,5-dichloropyridazin-4-yl)imidoformate (Preparation 40, 2 g, 9.3 mmol) in anhydrous THF (5 mL) in another flask at 0° C. drop-wise and stirred at room temperature for 16 hours. The reaction mixture was quenched with crushed ice and extracted with EtOAc (2×20 mL). The organic layer was washed with water (10 mL) and saturated brine solution (10 mL) then dried over $Na_2SO_4$ filtered and concentrated in vacuo. The residue was purified by silica gel column chromatography eluting with hexane:EtOAc 60:40 to afford the title compound as a white solid in 15% yield, 340 mg.

$^1$H NMR (400 MHz, $CDCl_3$): δ ppm 0.73-0.75 (m, 2H), 0.90-0.93 (m, 2H), 1.55 (s, 3H), 5.96 (br s, 1H), 7.43, 7.79 (d, 1H), 8.88 (s, 1H).

LCMS (System 7): Rt=2.74 minutes MS m/z 245 [M+H]$^+$

Preparation 97

4-Chloro-7-(1-methylcyclopropyl)-7H-imidazo[4,5-c]pyridazine

A suspension of N-(3,5-dichloropyridazin-4-yl)-AP-(1-methylcyclopropyl) imidoformamide (Preparation 96, 340 mg, 1.39 mmol) and cesium carbonate (908 mg, 2.78 mmol) in anhydrous DMF (10 mL) was degassed with argon for 10 minutes followed by the addition of 1,10-phenanthroline (25 mg, 0.14 mmol) and copper(I)bromide (10 mg, 0.07 mmol). The resulting mixture was heated at 90° C. for 16 hours and then cooled to room temperature. The mixture was filtered and filtrate was concentrated in vacuo. The crude residue was partitioned between $CH_2Cl_2$ (20 mL) and water (5 mL). The organic layer was separated and washed with water (5 mL) and saturated brine solution (5 mL) then dried over $Na_2SO_4$, filtered and concentrated in vacuo. The residue was purified by silica gel column chromatography eluting with hexane:EtOAc (60:40) to afford the title compound as off white solid in 21% yield, 60 mg.

$^1$H NMR (400 MHz, DMSO-$d_6$): δ ppm 1.08-1.11 (m, 2H), 1.32-1.35 (m, 2H), 1.67 (s, 3H), 8.94 (s, 1H), 9.26 (s, 1H).

LCMS (System 7): Rt=1.65 minutes MS m/z 209 [M+H]$^+$

Preparation 98

5-Chloro-N$^3$-cyclobutylpyridazine-3,4-diamine

A mixture of 3,5-dichloro-4-aminopyridazine (Preparation 4, 200 mg, 1.22 mmol), cyclobutyl amine (0.56 mL) and water (1.12 mL) was heated under microwave irradiation at 125° C. for 4 hours. The reaction mixture was concentrated in vacuo and the crude residue was purified by silica gel column chromatography eluting with $CH_2Cl_2$:MeOH 98:2 to afford the title compound as a brown solid in 58% yield, 140 mg.

$^1$H NMR (400 MHz, DMSO-$d_6$): δ ppm 1.68-1.75 (m, 2H), 1.84-1.92 (m, 2H), 2.30-2.37 (m, 2H), 4.40-4.46 (m, 1H), 6.15 (br s, 2H), 6.33 (br s, 1H), 8.10 (s, 1H).

LCMS (System 7): Rt=2.17 minutes MS m/z 199 [M+H]$^+$

Preparation 99

4-Chloro-7-cyclobutyl-7H-imidazo[4,5-c]pyridazine

A mixture of 5-chloro-N$^3$-cyclobutylpyridazin-3,4-diamine (Preparation 98, 140 mg, 0.70 mmol) and triethyl orthoformate (4 mL) was heated at 140° C. for 4 hours. After evaporation in vacuo, the crude residue was purified by silica gel column chromatography eluting with $CH_2Cl_2$:MeOH 99:1 to afford the title compound as an off white solid in 54% yield, 80 mg.

¹H NMR (400 MHz, DMSO-d₆): δ ppm 1.90-1.98 (m, 2H), 2.52-2.58 (m, 2H), 2.73-2.83 (m, 2H), 5.23-5.31 (m, 1H), 9.04 (s, 1H), 9.25 (s, 1H).

LCMS (System 7): Rt=2.29 minutes MS m/z 209 [M+H]⁺

Preparation 100

5-Chloro-N³-propylpyridazine-3,4-diamine

A mixture of 3,5-dichloro-4-aminopyridazine (Preparation 4, 2 g, 12.3 mmol) and 70% aqueous propylamine (8 mL) was heated at 125° C. in an autoclave vessel for 5 hours. The reaction mixture was cooled to room temperature and evaporated to dryness. The crude residue was purified by silica gel column chromatography eluting with CH₂Cl₂:MeOH 98:2 to afford the title compound as a brown solid in 35% yield, 800 mg.

¹H NMR (400 MHz, DMSO-d₆): δ ppm 0.94 (t, 3H), 1.53-1.64 (m, 2H), 3.26-3.34 (m, 2H), 6.45 (br s, 1H), 6.58 (br s, 2H), 8.23 (s, 1H).

LCMS (System 7): Rt=2.05 minutes MS m/z 187 [M+H]⁺

Preparation 101

4-Chloro-7-propyl-7H-imidazo[4,5-c]pyridazine

A mixture of 5-chloro-N³-propylpyridazine-3,4-diamine (Preparation 100, 800 mg, 4.30 mmol) and triethyl orthoformate (10 mL) was heated at 140° C. for 4 hours. After evaporation in vacuo, the crude residue was purified by silica gel column chromatography eluting with CH₂Cl₂:MeOH 98:2 to afford the title compound as a brown solid in 47% yield, 400 mg.

¹H NMR (400 MHz, DMSO-d₆): δ ppm 0.88 (t, 3H), 1.91-2.00 (m, 2H), 4.41 (t, 2H), 8.92 (s, 1H), 9.25 (s, 1H).

LCMS (System 7): Rt=2.12 minutes MS m/z 197 [M+H]⁺

Preparation 102

1-Bromo-4-(ethylsulfonyl)-2-chlorobenzene

To a room temperature solution of 1-bromo-4-ethylthio-2-chlorobenzene (Preparation 85, 1.6 g, 6.4 mmol) in DCM (30 mL) was added meta-chloroperoxybenzoic acid (3.13 g, 12.7 mmol) and the resulting reaction mixture was stirred for 18 hours. The reaction was filtered and washed with 1M aqueous Na₂CO₃ solution, dried and concentrated in vacuo. The residue was purified using silica gel column chromatography eluting with 5-15% EtOAc in heptanes to afford the title compound (1.51 g, 83%).

¹H NMR (400 MHz, CDCl₃): δ ppm 1.30 (t, 3H), 3.13 (q, 2H), 7.63 (dd, 1H), 7.84 (d, 1H), 7.98 (d, 1H).

LCMS Rt=2.85 minutes MS m/z no ionisation

Assay Methods
Cell Line Construction and Maintenance

Human Embryonic Kidney (HEK) cells were transfected with a GABRA2-GABRB2-GABRG2 construct using standard techniques. Cells stably expressing the GABRA2-GABRB2-GABRG2 constructs were identified by their resistance to Geneticin G-418 (320 μg/ml), Hygromycin (160 μg/ml) and Zeocin (40 μg/ml). Clones were screened for expression using the BD Pathway 855 imaging system (BD Biosciences, Rockville, Md., USA) and QPatch automated electrophysiology platform (Sophion, Copenhagen, Denmark).

Cell Culture

HEK cells stably transfected with GABRA2-GABRB2-GABRG2 were maintained in MEM medium with Earle's salts, 10% FBS, 1×L-Glutamax, 1% mM Non-essential Amino Acids (MEM) and 1 mM sodium pyruvate, with Geneticin G-418 (320 μg/ml), Hygromycin (160 μg/ml) and Zeocin (40 μg/ml), in an incubator at 37° C. with a humidified atmosphere of 5% CO₂. For QPatch electrophysiology testing, cells were harvested from flasks by enzymatic dissociation and resuspended in serum-free medium. Cells were typically used for electrophysiological experiments within 24 to 72 hours after splitting.

Binding Assay

The affinity of the test compounds was determined by radioligand competition binding assay, using the known compound [3H]Ro-15-1788 (Flumazenil) (Perkin Elmer, 85.4 Ci/mmol) and the human recombinant GABA A receptor containing the alpha2, beta2, and gamma3 subunits.

Membranes were prepared from HEK cells expressing hGABA A alpha2beta2-gamma3 receptor, and validated to ascertain protein concentration, receptor expression and to determine the Kd of the flumazenil as well as the Ki of a standard set of compounds before being used to test new compounds.

The assay was carried out in 96 well plates; testing compounds using a 10 point semi-log dilution range from 19 uM top concentration. 100 ul of radioligand and 100 ul of membrane in 50 mM Tris-HCl and 0.05% F127 with 1 ul of test compound was incubated for 2 hours to allow the reaction to achieve equilibrium, and then harvested onto filter plates, dried and counted on a TopCount NXT. The data was analysed, and the Ki values were presented as the geometric mean of at least two replicates.

Electrophysiological Recording

Cell suspension containing HEK cells expressing GABRA2-GABRB2-GABRG2 was placed on the QPatch instrument in serum-free medium into the instrument's cell stirrer. The instrument washed the cells once using extracellular buffer and then dispensed them into the QPlate HT measurement plate at a concentration of 3-4-e6/ml. Extracellular solution was of the following composition: 137 mM NaCl, 1.8 mM CaCl₂, 4 mM KCl, 1 mM MgCl₂, 10 mM glucose, and 10 mM HEPES, pH 7.4 with NaOH, 300-310 mOsm/kg. The internal side of the QPlate measurement plate was filled with intracellular solution of the following composition: 90 mM KCl, 50 mM KF, 1 mM MgCl₂, 10 mM HEPES, 11 mM EGTA, and 2 mM Mg-ATP, pH 7.35, with KOH, 295-305 mOsm/kg. All recordings were made at room temperature (22-24° C.).

GABRA2-GABRB2-GABRG2 chloride currents in HEK cells were measured using the whole-cell configuration of the patch-clamp technique (Hamill et al., 1981). Current records were acquired at 1 KHz and filtered at 0.3 KHz using the Bessel filter. Series resistance compensation was set to 80% in the QPatch software.

All compounds were dissolved in dimethyl sulfoxide to make 30 mM or 10 mM stock solutions, which were then diluted to 1000 times the desired final concentration in dimethyl sulfoxide. These were diluted into extracellular solution to attain the final concentrations desired. The final concentration of dimethyl sulfoxide (<0.1% dimethyl sulfoxide) was found to have no significant effect on GABRA2-GABRB2-GABRG2 chloride currents. This concentration of dimethyl sulfoxide was present in all samples.

Currents were recorded at −60 mV, using an approximately EC10 concentration of gamma-aminobutyric acid (GABA). This dose of gamma-aminobutyric acid was applied for 6 seconds and washed off using extracellular buffer as an unrecorded application using the pipetting system of the QPatch instrument. The same dose of gamma-aminobutyric acid was then applied for 9 seconds, then the test compound was co-applied with this dose of gamma-aminobutyric acid for 15 seconds, and washed off using the extracellular solution using the pipetting system of the QPatch instrument.

Compound effect (% enhancement of gamma-aminobutyric acid current) was calculated using the following formula:

[((peak modulator current amplitude-leak)−(GABA current amplitude-leak))/(GABA current amplitude-leak)]*100, where 'leak' is leak current at −60 mV, 'peak modulator current amplitude' is the current elicited by co-application of gamma-aminobutyric acid and test compound, and 'GABA current amplitude' is the current elicited by application of gamma-aminobutyric acid alone.

The ability of the compounds of the formula (I) to modulate the GABA channels expressing the α1 subunit (or GABRA1) can also be measured using an assay analogous to that described above but replacing the GABRA2-GABRB2-GABRG2 gene construct with the GABRA1-GABRB3-GABRG2 gene construct. All other conditions remain the same including the same cell line and conditions for cell growth. The % enhancement values generated in the assay using the GABRA1-GABRB3-GABRG2 construct can be compared to the results generated using the GABRA2-GABRB2-GABRG2 construct to determine the selectivity of a given compound.

Results

| Example | GABA-α2 Ki (nM) | α1 PAM (%) | α2 PAM (%) |
|---|---|---|---|
| 1 | 31.1 | 1.05 | 124 |
| 2 | 10.9 | −4.67 | 1.69 |
| 3 | 5.08 | −51.1 | 27.6 |
| 4 | <2.47 | 18.1 | 124 |
| 5 | 108 | | |
| 6 | 9.51 | | |
| 7 | 9.71 | | |
| 8 | 7.45 | −55.1 | 19.4 |
| 9 | 17.7 | −14.6 | 38.9 |
| 10 | 61.3 | | |
| 11 | 39.2 | −0.474 | 46.7 |
| 12 | 7.48 | 3.66 | 39.1 |
| 13 | 11.7 | 40.1 | 111 |
| 14 | 35.4 | 13.3 | 58.0 |
| 15 | 18.2 | −31.4 | 39.4 |
| 16 | 56.0 | | |
| 17 | 102 | | |
| 18 | 296 | | |
| 19 | 31.1 | −6.17 | 84.3 |
| 20 | 19.0 | | 36.3 |
| 21 | 43.3 | −5.78 | 31.6 |
| 22 | 67.8 | | |
| 23 | 40.5 | | |
| 24 | 37.1 | −0.441 | 55.3 |
| 25 | 170. | −5.82 | 23.9 |
| 26 | 147 | | |
| 27 | 34.8 | | |
| 28 | 74.3 | | |
| 29 | 101 | 69.4 | 173 |
| 30 | 120 | | |
| 31 | 23.9 | 21.3 | 118 |
| 32 | 5.82 | −29.5 | 77.2 |
| 33 | 16.4 | −27.0 | 79.9 |
| 34 | 34.5 | 4.99 | 94.7 |
| 35 | 38.8 | | |
| 36 | 87.4 | | |
| 37 | 19.1 | | |
| 38 | 8.56 | 14.6 | 62.5 |
| 39 | 14.4 | | |
| 40 | 14.0 | | |
| 41 | 29.1 | 14.9 | 81.3 |
| 42 | 91.4 | 112 | 199 |
| 43 | 118 | | |
| 44 | 678 | | |
| 45 | 29.7 | 20.8 | 61.1 |
| 46 | 1750 | | |
| 47 | 40.6 | 18.3 | 68.7 |
| 48 | 92.2 | −5.53 | 47.8 |
| 49 | 21.7 | −14.3 | 83.9 |
| 50 | 69.5 | 0.408 | 50.1 |

The invention claimed is:

1. A compound according to formula (I)

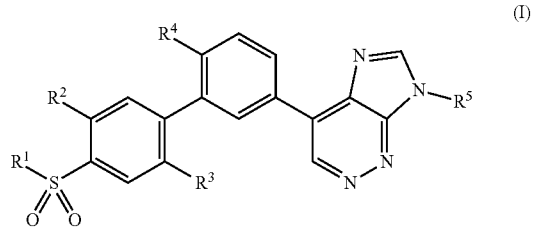

wherein
R$^1$ is selected from (C$_1$-C$_4$)alkyl, (C$_3$-C$_4$)cycloalkyl, NH$_2$, and NH(C$_1$-C$_4$)alkyl and R$^2$ is H; or
R$^1$ and R$^2$ together are —CH$_2$—CH$_2$— or —N(CH$_3$)—CH$_2$—;
R$^3$ is selected from H, F, CHF$_2$, OCH$_3$ and CN;
R$^4$ is selected from H, F, Cl, OH, OCH$_3$ and CN; and
R$^5$ is selected from (C$_2$-C$_4$)alkyl, (C$_3$-C$_5$)cycloalkyl and methyl-substituted (C$_3$-C$_5$)cycloalkyl,
or a pharmaceutically acceptable salt thereof.

2. The compound according to claim 1 wherein R$^1$ is (C$_2$-C$_4$)alkyl and R$^2$ is H, or a pharmaceutically acceptable salt thereof.

3. The compound according to claim 1 wherein R$^3$ is selected from F and OCH$_3$, or a pharmaceutically acceptable salt thereof.

4. The compound according to claim 1 wherein R$^4$ is selected from H and F, or a pharmaceutically acceptable salt thereof.

5. The compound according to claim 1 wherein R$^5$ is (C$_2$-C$_4$)alkyl, or a pharmaceutically acceptable salt thereof.

6. The compound according to claim 1 selected from:
7-ethyl-4-(6-fluoro-4'-((1-methylethyl)sulfonyl)biphenyl-3-yl)-7H-imidazo[4,5-c]pyridazine;
4-(4'-ethanesulfonyl-6-fluoro-2'-methoxybiphenyl-3-yl)-7-ethyl-7H-imidazo[4,5-c]pyridazine;
7-cyclopropyl-4-(4'-ethylsulfonyl-6-fluorobiphenyl-3-yl)-7H-imidazo[4,5-c]pyridazine; and
4-(4'-ethanesulfonyl-2',6-difluorobiphenyl-3-yl)-7-(1-methylethyl)-7H-imidazo[4,5-c]pyridazine.

7. The compound 4-(4'-ethanesulfonyl-6-fluoro-2'-methoxybiphenyl-3-yl)-7-ethyl-7H-imidazo[4,5-c]pyridazine.

8. The compound 4-(4'-ethanesulfonyl-6-fluoro-2'-methoxybiphenyl-3-yl)-7-ethyl-7H-imidazo[4,5-c]pyridazine or a pharmaceutically acceptable salt thereof.

9. A pharmaceutical composition comprising a compound according to claim 1 and a pharmaceutically acceptable excipient.

10. A combination comprising a compound according to claim 1 and a second pharmaceutically active agent.

11. A method of treating pain comprising the administration to a subject in need of such treatment of an effective amount of a compound according to claim 1.

12. A method of treating pain comprising the administration to a subject in need of such treatment of an effective amount of a compound according to claim 7.

13. A method of treating pain comprising the administration to a subject in need of such treatment of an effective amount of a compound according to claim 8.

14. A method for treating anxiety comprising the administration to a subject in need of such treatment of an effective amount of a compound according to claim 7.

15. A method for treating anxiety comprising the administration to a subject in need of such treatment of an effective amount of a compound according to claim 8.

16. A method for treating epilepsy comprising the administration to a subject in need of such treatment of an effective amount of a compound according to claim 7.

17. A method for treating epilepsy comprising the administration to a subject in need of such treatment of an effective amount of a compound according to claim 8.

18. A method of treating anxiety comprising the administration to a subject in need of such treatment of an effective amount of a compound according to claim 1.

19. A method of treating epilepsy comprising the administration to a subject in need of such treatment of an effective amount of a compound according to claim 1.

* * * * *